US012715911B2

(12) United States Patent
Voors

(10) Patent No.: US 12,715,911 B2
(45) Date of Patent: Aug. 25, 2026

(54) ANTI-ADRENOMEDULLIN (ADM) ANTIBODY OR ANTI-ADM ANTIBODY FRAGMENT OR ANTI-ADM NON-IG SCAFFOLD FOR USE IN INTERVENTION AND THERAPY OF CONGESTION IN A PATIENT IN NEED THEREOF

(71) Applicant: AdrenoMed AG, Hennigsdorf (DE)

(72) Inventor: Adriaan Voors, Nietap (NL)

(73) Assignee: ADRENOMED AG, Hennigsdorf (DE)

( * ) Notice: Subject to any disclaimer, the term of this patent is extended or adjusted under 35 U.S.C. 154(b) by 0 days.

(21) Appl. No.: 17/339,221

(22) Filed: Jun. 4, 2021

(65) Prior Publication Data

US 2022/0041703 A1 Feb. 10, 2022

Related U.S. Application Data

(63) Continuation of application No. 16/469,738, filed as application No. PCT/EP2017/083311 on Dec. 18, 2017, now abandoned.

(30) Foreign Application Priority Data

Dec. 16, 2016 (EP) .................................... 16204847
Dec. 22, 2016 (EP) .................................... 16206305
Oct. 18, 2017 (EP) .................................... 17197176

(51) Int. Cl.
*A61K 39/395* (2006.01)
*C07K 16/22* (2006.01)

(52) U.S. Cl.
CPC .......... *C07K 16/22* (2013.01); *C07K 2317/21* (2013.01); *C07K 2317/24* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 9,140,696 | B2 * | 9/2015 | Bergmann | G01N 33/6893 |
| 9,304,127 | B2 * | 4/2016 | Bergmann | C07K 16/18 |
| 9,402,900 | B2 | 8/2016 | Bergmann | |
| 10,221,238 | B2 | 3/2019 | Bergmann | |
| 10,227,405 | B2 | 3/2019 | Bergmann | |
| 2011/0301332 | A1 | 12/2011 | Wilson et al. | |
| 2013/0315912 | A1 | 11/2013 | Mabrouk | |
| 2014/0314775 | A1 | 10/2014 | Bergmann | |
| 2014/0322225 | A1 | 10/2014 | Bergmann | |
| 2014/0328853 | A1 | 11/2014 | Bergmann | |
| 2016/0159900 | A1 | 6/2016 | Bergmann | |
| 2016/0176960 | A1 | 6/2016 | Bergmann | |
| 2019/0010226 | A1 | 1/2019 | Bergmann | |
| 2019/0092857 | A1 | 3/2019 | Bergmann | |

FOREIGN PATENT DOCUMENTS

| | | | |
|---|---|---|---|
| CN | 104144948 | A | 11/2014 |
| EP | 2594587 | A1 | 5/2013 |
| JP | 2014533671 | A | 12/2014 |
| JP | 2014533672 | A | 12/2014 |
| JP | 2015501797 | A | 1/2015 |
| JP | 2015502349 | A | 1/2015 |
| KR | 20140102676 | A | 8/2014 |
| RU | 2586295 | C2 | 6/2016 |
| WO | 2010/000025 | A1 | 1/2010 |
| WO | 2013/072511 | A1 | 5/2013 |
| WO | 2013/072512 | A1 | 5/2013 |
| WO | 2013/072513 | A1 | 5/2013 |
| WO | 2013/072514 | A1 | 5/2013 |
| WO | 2013072510 | A1 | 5/2013 |

OTHER PUBLICATIONS

J.P. Hinson et al., "Adrenomedullin, a Multifunctional Regulatory Peptide", Endocrine Reviews, vol. 21, No. 2 (Apr. 1, 2000) pp. 138-167.
Chinese Office Action dated Nov. 25, 2022, issued in corresponding application No. CN 104144948A (pp. 1-6).
Mexican Office Action dated Nov. 7, 2023, issued in corresponding application No. MX 2019007107 (pp. 1-4).
Joachim Struck et al. "Epitope specificity of anti-Adrenomedullin antibodies determines efficacy of mortality reduction in a cecal ligation and puncture mouse model." Intensive Care Med Exp., Oct. 2013, vol. 1, No. 3, p. 22.
Neuberg GW, Miller AB, O'Connor CM, Belkin RN, Carson PE, Cropp AB, Frid DJ, Nye RG, Pressler ML, Wertheimer JH, Packer M; Praise Investigators. Prospective Randomized Amlodipine Survival Evaluation. Diuretic resistance predicts mortality in patients with advanced heart failure. Am Heart J. Jul. 2002;144(1):31-8. doi: 10.1067/mhj.2002.123144. PMID: 12094185.
Badri H. et al: "Optimization of radiation dosing schedules for proneural glioblastoma", Journal of Mathematical Biology, Jun. 21, 2015, vol. 72, pp. 1301-1336.
Baylot V. et al: "Chapter 13: TCTP Has a Crucial Role in the Different Stages of Prostate Cancer Malignant Progression", Telerman, A., Amson, R. (eds) TCTP/tpt1—Remodeling Signaling from Stem Cell to Disease, Results and Problems in Cell Differentiation, Nov. 18, 2017, vol. 64, pp. 255-261.
Boorsma E. M. et al: "Congestion in heart failure: a contemporary look at physiology, diagnosis and treatment", Nature Reviews Cardiology, Oct. 2020, vol. 17, pp. 641-655.

(Continued)

*Primary Examiner* — Christine J Saoud

(74) *Attorney, Agent, or Firm* — Millen, White, Zelano & Branigan P.C.; Ryan R. Pool

(57) ABSTRACT

Subject matter of the present invention is an anti-Adrenomedullin (ADM) antibody or an anti-Adrenomedullin antibody fragment or an anti-ADM non-Ig scaffold for use in intervention and therapy of congestion in a patient in need thereof.

6 Claims, 21 Drawing Sheets

Specification includes a Sequence Listing.

(56) References Cited

OTHER PUBLICATIONS

Boyle A., MD et al: "Myocellular and Interstitial Edema and Circulating Volume Expansion as a Cause of Morbidity and Mortality in Heart Failure", Journal of Cardiac Failure, 2007, vol. 13, No. 2, pp. 133-136.
Dondelinger M. et al: "Understanding the Significance and Implications of Antibody Numbering and Antigen-Binding Surface/Residue Definition", Frontiers in Immunology, Oct. 16, 2018, vol. 9, Article 2278, pp. 1-15.
Angeli, P. et al: "EASL Clinical Practice Guidelines for the management of patients with decompensated cirrhosis", Journal of Hepatology, 2018, vol. 69, Iss. 2, pp. 1-55.
Gebauer M. et al: "Engineered protein scaffolds as next-generation antibody therapeutics", Current Opinion in Chemical Biology, vol. 13, Iss. 3, Jun. 2009, pp. 245-255.
Geven C. et al: "Adrenomedullin and Adrenomedullin-Targeted Therapy as Treatment Strategies Relevant for Sepsis", Frontiers in Immunology, Feb. 19, 2018, vol. 9, Article 292, pp. 1-14.
Kellum J. A. et al: "Diagnosis, evaluation, and management of acute kidney injury: a KDIGO summary (Part 1)", Critical Care, Feb. 4, 2013, vol. 17, Article 204, pp. 1-15.
Molvin J. et al: "Bioactive adrenomedullin, proenkephalin A and clinical outcomes in an acute heart failure setting", Open Heart, Jul. 3, 2019, vol. 6, No. 2, pp. 1-9.
Pandhi P. et al: "Clinical value of pre-discharge bio-adrenomedullin as a marker of residual congestion and high risk of heart failure hospital readmission", European Journal of Heart Failure, Dec. 3, 2019, vol. 22, Iss. 4, pp. 1-9.
Ponikowski P. et al: "2016 ESC Guidelines for the diagnosis and treatment of acute and chronic heart failure: The Task Force for the diagnosis and treatment of acute and chronic heart failure of the European Society of Cardiology (ESC). Developed with the special contribution of the Heart Failure Association (HFA) of the ESC", European Heart Journal, May 20, 2016, vol. 18, Iss. 8, pp. 891-975.
Van Regenmortel M.H.V. et al: "Specificity, polyspecificity, and heterospecificity of antibody-antigen recognition", Journal of Molecular Recognition, Sep. 8, 2014, vol. 27, Iss. 11, pp. 627-639.
Shah N. et al: "A perspective on diuretic resistance in chronic congestive heart failure", Therapeutic Advances in Cardiovascular Disease, Jul. 20, 2017, vol. 11, No. 10, pp. 271-278.
Uhl P. et al: "Current Status in the Therapy of Liver Diseases", International Journal of Molecular Sciences, Apr. 30, 2014, vol. 15, No. 5, pp. 7500-7512.
Voors A. A. et al: "Adrenomedullin in heart failure: pathophysiology and therapeutic application", European Journal of Heart Failure, Feb. 2019, vol. 21, Iss. 2, pp. 163-171.
Wagner K. et al: "Adrenomedullin binding improves catecholamine responsiveness and kidney function in resuscitated murine septic shock", Journal of Software Engineering Research and Development, Oct. 29, 2013, vol. 1, Article 2, pp. 1-15.
Wang R. et al: "GARP regulates the bioavailability and activation of TGFβ", Molecular Biology of the Cell, Mar. 15, 2012, vol. 23, No. 6, pp. 1129-1139.
Wilcox C. S. et al: "Pathophysiology of Diuretic Resistance and Its Implications for the Management of Chronic Heart Failure", Hypertension, Oct. 2020, pp. 1045-1054.
Wurch T. et al: "Novel protein scaffolds as emerging therapeutic proteins: from discovery to clinical proof-of-concept", Trends in Biotechnology, Nov. 2012, vol. 30, No. 11, pp. 575-582.

* cited by examiner

Fig 5:

**IGHV1-69*11 (SEQ ID No.:36):**

QVQLVQSGAEVKKPGSSVKVSCKASGGTFSSYAISWVRQAPGQGLEWMGRIIPILGT
ANYAQKFQGRVTITADESTSTAYMELSSLRSEDTAVYYCARYYYYYGMDVWGQGT
TVTVSS

HB3:

QVQLQQSGAELMKPGASVKISCKATGYTFSRYWIEWVKQRPGHGLEWIGEILPGSGS
TNYNEKFKGKATITADTSSNTAYMQLSSLTSEDSAVYYCTEGYEYDGFDYWGQGTT
LTVSS

Alignment (ClustalW2): Identical amino acids are illustrated by stars; points indicate conservative changes.

```
IGHV1:
        QVQLVQSGAEVKKPGSSVKVSCKASGGTFSSYAISWVRQAPGQGLEWMGRIIPILGTANYAQKFQGR
        VTITADESTSTAYMELSSLRSEDTAVYYCARYYYYYGMDVWGQGTTVTVSS
HB3:
        QVQLQQSGAELMKPGASVKISCKATGYTFSRYWIEWVKQRPGHGLEWIGEILPGSGSTNYNEKFKGK
        ATITADTSSNTAYMQLSSLTSEDSAVYYCTEGYEYDGFDYWGQGTTLTVSS
        **** *****: ***:***:****:* *** * *.**:* **:****:*.*:*  *::** :**:*:
        .***** *:.****:**** ***:*****:. * * *:* ******:****
```

Fig. 19
A
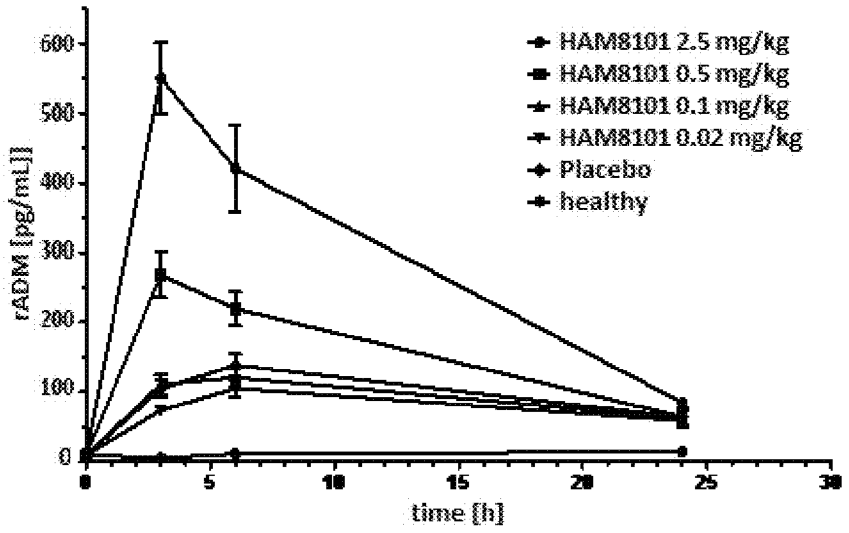
B
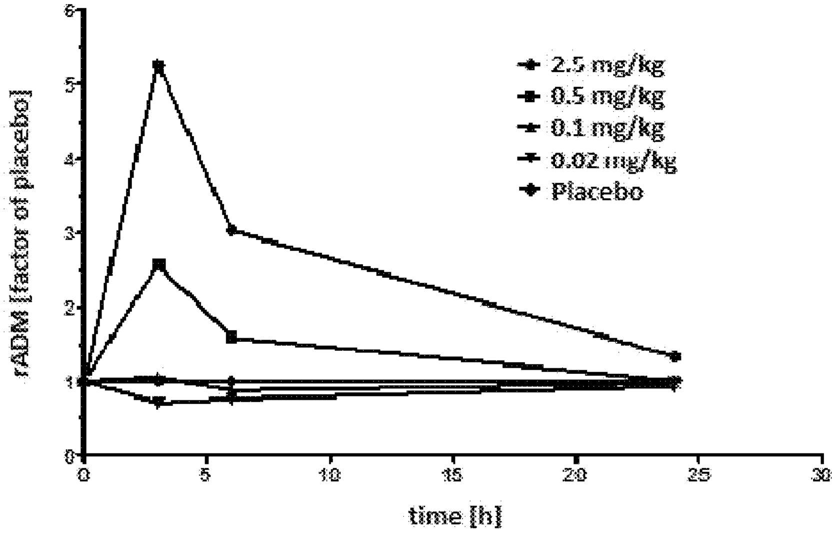

Fig. 20
A – Kidney
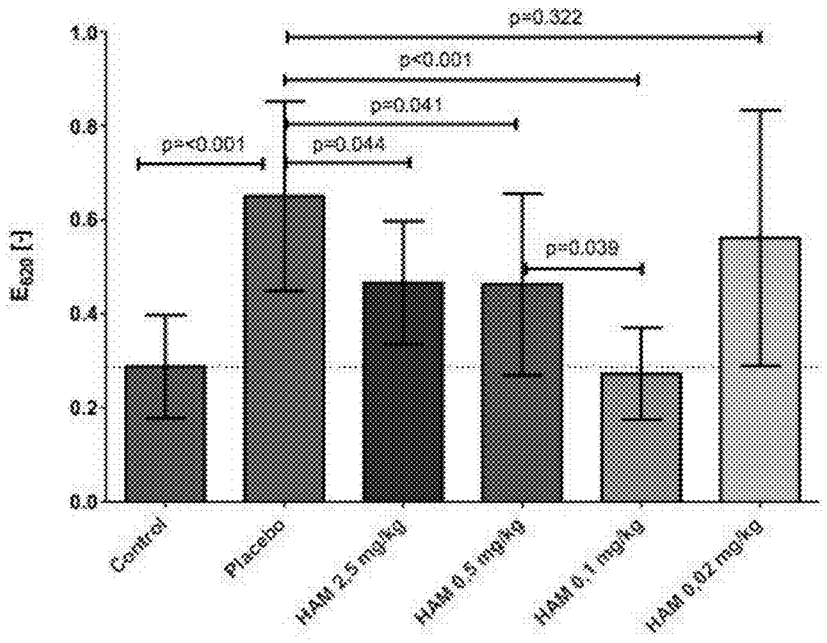
B - Liver
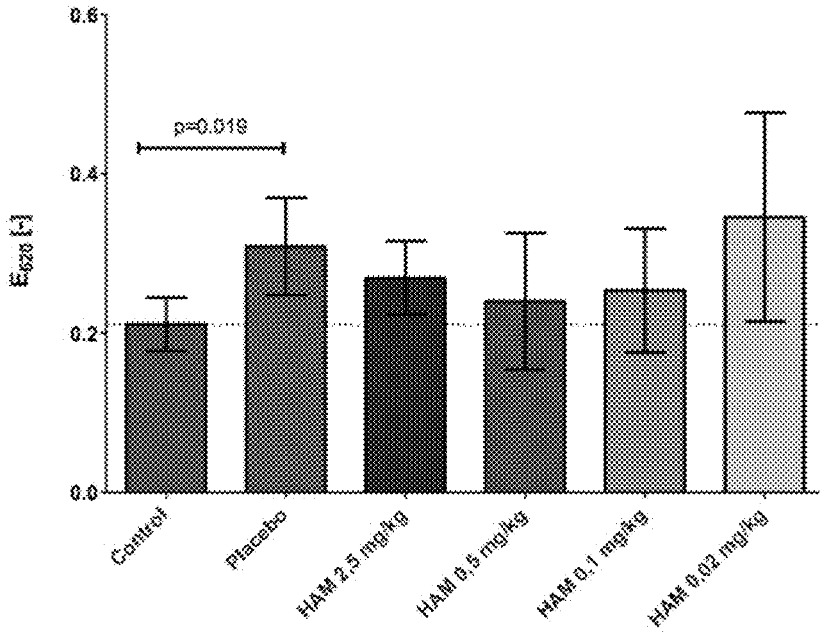

ANTI-ADRENOMEDULLIN (ADM) ANTIBODY OR ANTI-ADM ANTIBODY FRAGMENT OR ANTI-ADM NON-IG SCAFFOLD FOR USE IN INTERVENTION AND THERAPY OF CONGESTION IN A PATIENT IN NEED THEREOF

FIELD OF THE INVENTION

Subject matter of the present invention is an anti-Adrenomedullin (ADM) antibody or an anti-Adrenomedullin antibody fragment or an anti-ADM non-Ig scaffold for use in intervention and therapy of congestion in a patient in need thereof.

BACKGROUND

The peptide adrenomedullin (ADM) was described for the first time in 1993 (Kitamura et al., 1993. *Biochem Biophys Res Comm* 192 (2): 553-560) as a novel hypotensive peptide comprising 52 amino acids, which had been isolated from a human pheochromocytoma cell line (SEQ ID No.: 20). In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "pre-proadrenomedullin" (pre-proADM). In the present description, all amino acid positions specified usually relate to the pre-proADM, which comprises the 185 amino acids. The peptide adrenomedullin (ADM) is a peptide which comprises 52 amino acids (SEQ ID No: 20) and which comprises the amino acids 95 to 146 of pre-proADM, from which it is formed by proteolytic cleavage. To date, substantially only a few fragments of the peptide fragments formed in the cleavage of the pre-proADM have been more exactly investigated, in particular the physiologically active peptides ADM and "PAMP", a peptide comprising 20 amino acids (22-41), which follows the 21 amino acids of the signal peptide in pre-proADM. The discovery and characterization of ADM in 1993 triggered intensive research activity, the results of which have been summarized in various review articles, in the context of the present description, reference being made in particular to the articles to be found in an issue of "Peptides" devoted to ADM in particular (Takahashi 2001. *Peptides* 22: 1691: *Eto* 2001. *Peptides* 22: 1693-1711). A further review is Hinson et al. 2000 (Hinson et al. 2000. *Endocrine Reviews* 21(2:138-167). In the scientific investigations to date, it has been found, inter alia, that ADM may be regarded as a polyfunctional regulatory peptide. It is released into the circulation in an inactive form extended by glycine (Kitamura et al. 1998. *Biochem Biophys Res Commun* 244(2): 551-555). There is also a binding protein (Pio et al. 2001. *The Journal of Biological Chemistry* 276(15). 12292-12300), which is specific for ADM and probably likewise modulates the effect of ADM. Those physiological effects of ADM as well as of PAMP, which are of primary importance in the investigations to date, were the effects influencing blood pressure.

Hence, ADM is an effective vasodilator, and thus it is possible to associate the hypotensive effect with the particular peptide segments in the C-terminal part of ADM. It has furthermore been found that the above-mentioned physiologically active peptide PAMP formed from pre-proADM likewise exhibits a hypotensive effect, even if it appears to have an action mechanism differing from that of ADM (in addition to the above mentioned review articles Eto et al. 2001 and Hinson et al. 2000 see also Kuwasaki et al. 1997. *FEBS Lett* 414(1): 105-110: Kuwasaki et al. 1999. *Ann. Clin. Biochem.* 36: 622-628: Tsuruda et al. 2001 *Life Sci.* 69(2): 239-245 and EP-A20 622458). It has furthermore been found, that the concentrations of ADM, which can be measured in the circulation and other biological liquids, are in a number of pathological states, significantly above the concentrations found in healthy control subjects. Thus, the ADM level in patients with congestive heart failure, myocardial infarction, kidney diseases, hypertensive disorders, diabetes mellitus, in the acute phase of shock and in sepsis and septic shock are significantly increased, although to different extents. The PAMP concentrations are also increased in some of said pathological states, but the plasma levels are lower relative to ADM (Eto 2001. *Peptides* 22: 1693-1711). It was reported that unusually high concentrations of ADM are observed in sepsis, and the highest concentrations in septic shock (Eto 2001. *Peptides* 22: 1693-1711: Hirata et al. *Journal of Clinical Endocrinology and Metabolism* 81(4): 1449-1453: Ehlenz et al. 1997. *Exp Clin Endocrinol Diabetes* 105: 156-162; Tomoda et al. 2001. *Peptides* 22: 1783-1794: Ueda et al. 1999. *Am. J. Respir. Crit. Care Med.* 160: 132-136 and Wang et al. 2001. *Peptides* 22: 1835-1840).

Plasma concentrations of ADM are elevated in patients with heart failure and correlate with disease severity (Hirayanna et al. 1999. *J Endocrinol* 160: 297-303: Yu et al. 2001. *Heart* 86: 155-160). High plasma ADM is an independent negative prognostic indicator in these subjects (Povner et al. 2002. *Pharmacol Rev* 54: 233-246).

The role of MR-proADM (SEQ ID No.: 33) in heart failure was explored in several studies. In the BACH study (Maisel et al. 2010. *J. Am. Coll. Cardiol.* 55: 2062-2076), MR-proADM was powerfully prognostic for death at 90 days, adding prognostic value beyond natriuretic peptides.

Subsequent data from the PRIDE study (Shah et al. 2012. *Eur. Heart J.* 33: 2197-2205) solidified a potential prognostic role for MR-proADM; among patients MR-proADM had the best area under the curve (AUC) for mortality at 1 year. Similarly, levels of MR-proADM in patients with chronic heart failure (CHF) were strongly correlated with disease severity and elevated levels of the peptide were strongly associated with an increased risk of death at 12 months of follow-up (van Haehling et al. 2010. *European Journal of Heart Failure* 12: 484-491: Adlbrecht et al. 2009. *European Journal of Heart Failure* 11: 361-366).

MR-proADM was investigated during treatment in patients with acute decompensated heart failure (Boyer et al. 2012. *Congest Heart Fail* 18 (2): 91-97): patients whose MR-proADM levels tended to increase during acute therapy had findings associated with persistent congestion. In the 12-24 hour time-period after therapy, patients with elevations of MR-proADM had increased peripheral edema. Kaiser et al. measured MR-proADM in patients with univentricular hearts (Kaiser et al. 2014. *Europ J Heart Failure* 16: 1082-1088). Levels in patients with a failed Fontan circuit (exhibiting ascites and peripheral edema) were significantly higher as compared to patients without Fontan failure. Moreover, Eisenhut speculated, whether treatments leading to a reduction of adrenomedullin levels can reduce the severity and extent of alveolar edema in pneumonia and septicemia (Eisenhut 2006. *Crit Care* 10: 418)

Known in the art is further a method for identifying adrenomedullin immunoreactivity in biological liquids for diagnostic purposes and, in particular within the scope of sepsis diagnosis, cardiac diagnosis and cancer diagnosis. According to the invention, the midregional partial peptide of the proadrenomedullin (SEQ ID No. 33), which contains amino acids (45-92) of the entire preproadrenomedullin, is measured in particular with an immunoassay, that works with at least one labeled antibody that specifically recognizes a sequence of the mid-proADM (WO2004/090546).

WO2004/097423 describes the use of an antibody against adrenomedullin for diagnosis, prognosis, and treatment of cardiovascular disorders. Treatment of diseases by blocking the ADM receptor are also described in the art, (e.g. WO2006/027147, PCT/EP2005/012844) said diseases may be sepsis, septic shock, cardiovascular diseases, infections, dermatological diseases, endocrinological diseases, metabolic diseases, gastroenterological diseases, cancer, inflammation, hematological diseases, respiratory diseases, muscle skeleton diseases, neurological diseases, urological diseases.

It is reported for the early phase of sepsis that ADM improves heart function and the blood supply in liver, spleen, kidney and small intestine. Anti-ADM-neutralizing antibodies neutralize the before mentioned effects during the early phase of sepsis (Wang et al. 2001. *Peptides* 22: 1835-1840).

For other diseases blocking of ADM may be beneficial to a certain extent. However, it might also be detrimental if ADM is totally neutralized, as a certain amount of ADM may be required for several physiological functions. In many reports it was emphasized, that the administration of ADM may be beneficial in certain diseases. In contrast thereto, in other reports ADM was reported as being life threatening when administered in certain conditions.

WO2013/072510 describes a non-neutralizing anti-ADM antibody for use in therapy of a severe chronical or acute disease or acute condition of a patient for the reduction of the mortality risk for said patient.

WO2013/072511 describes a non-neutralizing anti-ADM antibody for use in therapy of a chronical or acute disease or acute condition of a patient for prevention or reduction of organ dysfunction or organ failure.

WO2013/072512 describes a non-neutralizing anti-ADM antibody that is an ADM stabilizing antibody that enhances the half-life (tin half retention time) of adrenomedullin in serum, blood, plasma. This ADM stabilizing antibody blocks the bioactivity of ADM to less than 80%.

WO2013/072513 describes a non-neutralizing anti-ADM antibody for use in therapy of an acute disease or condition of a patient for stabilizing the circulation.

WO2013/072514 describes a non-neutralizing anti-ADM antibody for regulating the fluid balance in a patient having a chronic or acute disease or acute condition.

Figure 1A:
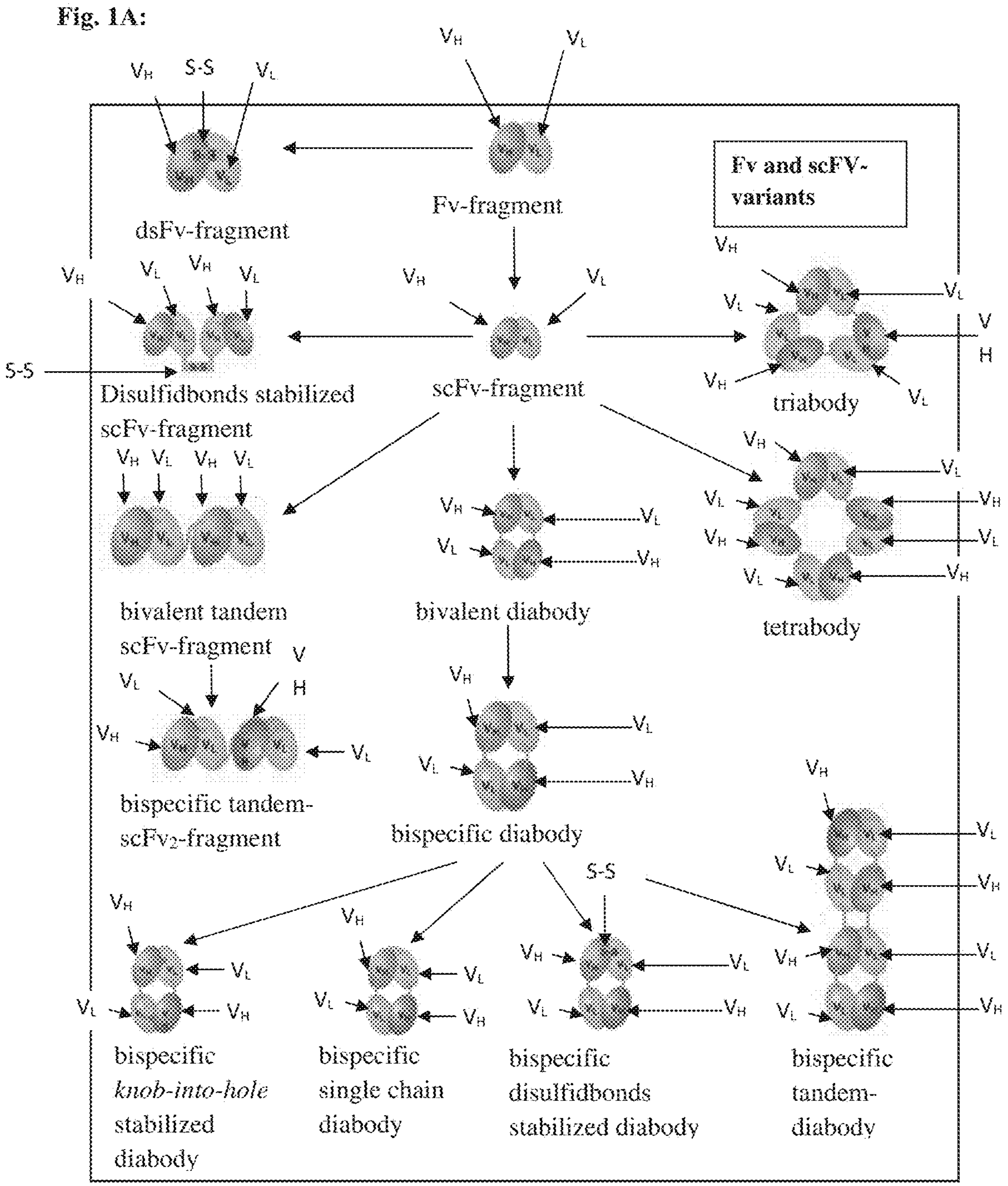
FIG. 1A.

Illustration of antibody formats—Fv and scFv-Variants.

FIG. 1B:

Illustration of antibody formats—heterologous fusions and bifunctional antibodies.

FIG. 1C:

Illustration of antibody formats—bivalental antibodies and bispecific antibodies.

FIG. 2A:

Dose response curve of human ADM. Maximal cAMP stimulation was adjusted to 100% activation.

FIG. 2B:

Dose/inhibition curve of human ADM 22-52 (ADM-receptor antagonist) in the presence of 5.63 nM hADM.

FIG. 2C:

Dose/inhibition curve of CT-H in the presence of 5.63 nM hADM.

FIG. 2D:

Dose/inhibition curve of MR-H in the presence of 5.63 nM hADM.

FIG. 2E:

Dose/inhibition curve of NT-H in the presence of 5.63 nM hADM.

FIG. 2F:

Dose response curve of mouse ADM. Maximal cAMP stimulation was adjusted to 100% activation.

FIG. 2G:

Dose/inhibition curve of human ADM 22-52 (ADM-receptor antagonist) in the presence of 0.67 nM mADM.

FIG. 2H:

Dose/inhibition curve of CT-M in the presence of 0.67 nM mADM.

FIG. 2I:

Dose/inhibition curve of MR-M in the presence of 0.67 nM mADM.

FIG. 2J:

Dose/inhibition curve of NT-M in the presence of 0.67 nM mADM.

FIG. 2K:

Shows the inhibition of ADM by F(ab)2 NT-M and by Fab NT-M.

FIG. 2L:

shows the inhibition of ADM by F(ab)2 NT-M and by Fab NT-M.

FIG. 3:

This figure shows a typical hADM dose/signal curve. And an hADM dose signal curve in the presence of 100 μg/mL antibody NT-H.

FIG. 4:

This figure shows the stability of hADM in human plasma (citrate) in absence and in the presence of NT-H antibody.

FIG. 5:

Alignment of the Fab with homologous human framework sequences.

FIG. 6:

Extravascular Albumin accumulation 18 h after CLP and NT-M application on different doses.

FIG. 7:

VEGF expression 18 h after CLP and NT-M application at different doses.

FIG. 8:

Angiopoetin-1 expression 18 hours after CLP and NT-M application at different doses.

FIG. 9:

ADM-concentration in healthy human subjects after NT-H application at different doses up to 60 days.

FIG. 10:

Time schedule for treatment and drawing of blood samples in the two-hit pig model.

FIG. 11:

ADM concentrations of vehicle (squares) and treatment (dots) group (mean values with SEM) ($p=0.003$ for interaction; t=7 h till 19 h, multivariate, Time*Group).

FIG. 12:

Heart rate of vehicle (squares) and treatment (dots) group (mean values with SEM), $p=0.097$ for interaction (from t=7 h till t=19 h, multivariate, Time*Group).

FIG. 13:

Cardiac output of vehicle (squares) and treatment (dots) group (mean values with SEM) (t-Test: $p<0.05$ for t=9, 10, 11 h).

FIG. 14:

Volume demand/application of vehicle (squares) and treatment (dots) group (mean values with SEM) (t-Test at 17 h: p=0.034; t-Test at 19 h: p=0.045).

FIG. 15:

Cumulated volume demand/application of vehicle (squares) and treatment (dots) group (mean values with SEM) (p=0.039 for t-Test at 19 h; p=0.036 for Mann-Whitney at 19 h).

FIG. 16:

Noradrenalin demand/application of vehicle (squares) and treatment (dots) group (mean values with SEM).

FIG. 17:

Requirement for vasopressor support of vehicle (squares) and treatment (dots) group (Chi$^2$ test at t=19 h: p=0.014 for Interaction (t=7 h-19 h, multivariate, Time*Group: 0.019).

FIG. 18:

Systemic vascular resistance of vehicle (squares) and treatment (dots) group (mean values with SEM) (t-Test: 15 h: p=0.069; 17 h: p=0.037; 19 h: p=0.066).

FIG. 19A:

rADM Concentrations in LPS-Induced Endotoxemia Rat Model

FIG. 19B:

rADM Concentrations in LPS-Induced Endotoxemia Rat Model

FIG. 20A:

Vascular Permeability in an Endotoxemia Rat Model—Kidney

FIG. 20B:

Vascular Permeability in an Endotoxemia Rat Model—Liver

DESCRIPTION OF THE INVENTION

According to the present invention it has been found that the administration of an anti-ADM antibody or anti-ADM antibody fragment binding to ADM or anti-ADM non-Ig scaffold binding to ADM may be used for the intervention and therapy of congestion of patients in need thereof.

Throughout the specification the "antibodies", or "antibody fragments" or "non-Ig scaffolds" in accordance with the invention are capable to bind ADM, and thus are directed against ADM, and thus can be referred to as "anti-ADM antibodies", "anti-ADM antibody fragments", or "anti-ADM non-Ig scaffolds".

The advantage of the administration of an anti-ADM antibody or anti-ADM antibody fragment binding to ADM or anti-ADM non-Ig scaffold binding to ADM in contrast to the administration of e.g. diuretics is the kidney protecting effect. Said anti-ADM antibody or anti-ADM antibody fragment binding to ADM or anti-ADM non-Ig scaffold binding to ADM is not harming the kidney and therefore, no side effects are expected in this regard.

In accordance with the invention the administration of an anti-ADM antibody or anti-ADM antibody fragment binding to ADM or anti-ADM non-Ig scaffold binding to ADM is preferably a systemic application.

In a specific embodiment said anti-ADM antibody or anti-ADM antibody fragment binding to ADM or anti-ADM non-Ig scaffold binding to ADM may be administered to a patient with vascular barrier dysfunction or endothelial dysfunction that may result in congestion.

Vascular barrier dysfunction or endothelial dysfunction is a systemic pathological state of the endothelium (the inner lining of blood vessels) and can be broadly defined as an imbalance between vasodilating and vasoconstricting substances produced by (or acting on) the endothelium (Deanfield et al. 2005. *J Hypertens.* 23(1): 7-17). Normal functions of endothelial cells include mediation of coagulation, platelet adhesion, immune function and control of volume and electrolyte content of the intravascular and extravascular spaces. The endothelium is a cellular monolayer that lines the entire cardiovascular system and regulates many processes including vascular tone, thrombosis, angiogenesis, and inflammation. Endothelial cells have been shown to be phenotypically dynamic and, in response to a variety of local and systemic stimuli, are able to transition between quiescent and activated states (Colombo et al. 2015. *Curr Heart Fail Rep.* 12(3): 215-222). In recent years, emerging research has demonstrated that endothelial dysfunction is a major contributor to cardiovascular disease, including hypertension, atherosclerosis, and congestive heart failure (Gutierrez et al. 2013. *European Heart Journal* 34: 3175-3181). The endothelium tightly controls the exchange of fluid from the circulation to the surrounding tissues and dysfunction of this barrier leads to uncontrolled fluid extravasation that may result in congestion and/or edema. A common feature of edema (e.g. pulmonary edema) is increased permeability to water low molecular weight solutes (Rocker et al. 1987. *Thorax* 42: 620-23).

Endothelial dysfunction can result from and/or contribute to several disease processes, as occurs in hypertension, hypercholesterolaemia, diabetes or septic shock. Endothelial dysfunction is a major pathophysiological mechanism that leads towards coronary artery disease, and other atherosclerotic diseases.

From preclinical experiments in models of sepsis/septic shock it is known that administration of the anti-ADM antibody induces an increase of the plasma bio-ADM concentration (Example 8, FIG. 9), and that this coincides with an increased survival rate (Struck et al. 2013. *Intensive Care Med Exp* 1(1):22). The mechanism underlying this effect is thought as follows: The antibody, when administered i.v., due to its size cannot cross the endothelial barrier into the interstitium, but remains in the blood circulation. In contrast, ADM, as a small peptide, can freely diffuse across the endothelial barrier. Thus, the antibody, when administered in a vast molar excess over the endogenous ADM, binds virtually all ADM in the plasma and, as a simple consequence of reaching binding equilibrium, leads to a translocation of ADM from the interstitium to the blood circulation. Interstitially located ADM can bind to vascular smooth muscle cells and induces relaxation resulting in vasodilation. This is reduced by administration of the antibody. On the other hand, ADM in plasma binds to endothelial cells and thereby stabilizes or even restores vascular integrity. Thus, this function is strengthened, when plasma ADM levels increase as a consequence of administration of the antibody, which is a non-neutralizing antibody. Finally, binding of the antibody to ADM reduces the proteolytic decay of ADM.

Surprisingly, we have observed in the PROTECT study (Example 6) and the BIOSTAT study (Example 7), that in subjects with heart failure bio-ADM concentrations increase with the presence and severity of congestion, despite their treatment with diuretics. Thus, bio-ADM increase in these patients is the body's counter regulation of the tissue congestion. However, the natural increase is insufficient to effectively achieve this counter regulation. Tissue congestion also occurs in sepsis. Examples 5, 9 and 10 demonstrates that administration of the anti-ADM antibody in septic animal models leads to restoration of impaired vascular integrity. Due to the parallel mechanism of tissue congestion in both sepsis and heart failure, it is credible for the expert in the field, that administration of the anti-ADM antibody must be beneficial in the treatment of congestion in heart failure, similar as in sepsis/septic shock.

In a specific embodiment said anti-ADM antibody or anti-ADM antibody fragment binding to ADM or anti-ADM non-Ig scaffold binding to ADM may be administered to a patient for use in intervention and therapy of congestion with help of a companion diagnostic method. Said companion diagnostic method is described below.

Pro-Adrenomedullin or fragments thereof of at least 5 amino acids may be used as an early surrogate marker for congestion and thereby guiding therapy or intervention of congestion comprising:

Determining the level of Pro-Adrenomedullin or fragments thereof of at least 5 amino acids in a bodily fluid obtained from said subject; and a) Correlating said level of Pro-Adrenomedullin or fragments thereof with the extent of congestion in said subject or diagnosing congestion, wherein an elevated level above a certain threshold is indicative of congestion or the extent of congestion or, b) Correlating said level of Pro-Adrenomedullin or fragments thereof with the need or success of a therapy or intervention and therapy of congestion in said subject, wherein a level below a certain threshold is predictive for a success of therapy or intervention and therapy of congestion, and wherein a level above a certain threshold is indicative for the need of therapy or intervention and therapy of congestion, or c) Correlating said level of Pro-Adrenomedullin or fragments thereof with a prediction of decongestion or residual congestion after therapy or intervention and therapy of congestion, wherein an elevated level above a certain threshold predicts residual congestion after therapy or intervention and therapy of congestion, whereas a level below a certain threshold predicts decongestion after therapy or intervention and therapy of congestion, or d) Correlating said level of Pro-Adrenomedullin or fragments thereof with decongestion or residual congestion after therapy or intervention and therapy of congestion wherein an elevated level above a certain threshold indicates residual congestion after therapy or intervention and therapy of congestion whereas a level below a certain threshold indicates decongestion after therapy or intervention and therapy of congestion, or e) Correlating said level of Pro-Adrenomedullin or fragments thereof with the assessment of the decision on hospital discharge wherein an elevated level above a certain threshold means that the subject shall not be discharged and wherein a level below a certain threshold means that the subject may be discharged, wherein said Pro-Adrenomedullin or fragment is selected from the group comprising Pro-Adrenomedullin according to SEQ ID No. 31 or PAMP according to SEQ ID No.: 32 or MR-proADM according to SEQ ID No.: 33 or ADM-$NH_2$ according to SEQ ID No.: 20 or ADM-Gly according to SEQ ID No.: 34 or CT-proADM according to SEQ ID No.: 35.

Such a method is described in detail in European Patent Application EP16199092 and EP16178725 and incorporated herein by reference. The therapy and intervention as mentioned in the diagnostic method above is the administration of said anti-ADM antibody or anti-ADM antibody fragment binding to ADM or anti-ADM non-Ig scaffold binding to ADM.

Severity of congestion, extent of congestion, degree of congestion, grade of congestion and the like are used synonymously throughout this application.

Mature ADM, bio-ADM and ADM —$NH_2$ is used synonymously throughout this application and is a molecule according to SEQ ID No.: 20.

Pro-Adrenomedullin or fragments thereof are an early, quantitative and accurate surrogate for congestion in the setting of acute heart failure and heart failure, in particular in a subject having acute heart failure and/or a subject having heart failure presenting with worsening signs and/or a subject with symptoms of heart failure or acute heart failure. Early and accurate surrogate for congestion in the setting of acute heart failure or heart failure means that their concentration and/or level of immune reactivity reflects the extent of congestion.

If said level of Pro-Adrenomedullin or fragments thereof is above a certain threshold level the anti-ADM antibody or anti-ADM antibody fragment binding to ADM or anti-ADM non-Ig scaffold binding to ADM is administered as therapy or intervention of congestion.

This means in a specific embodiment subject matter of the present invention said anti-ADM antibody or anti-ADM antibody fragment binding to ADM or anti-ADM non-Ig scaffold binding to ADM is for use in intervention and therapy of congestion in a patient, wherein a sample of bodily fluid taken from said patients exhibits an elevated level of proADM and/or fragments thereof having at least 5 amino acids above a certain threshold. Thus, the diagnostic method using said proADM and/or fragments serves as companion diagnostic method.

In a specific embodiment of the diagnostic method said proADM and/or fragments thereof having at least 5 amino acids is/are selected from the group comprising:

```
(proADM): 164 amino acids (22-185 of preproADM)
                                          SEQ ID No.: 31
ARLDVASEF RKKWNKWALS RGKRELRMSS SYPTGLADVK

AGPAQTLIRP QDMKGASRSP EDSSPDAARI RVKRYRQSMN

NFQGLRSFGC RFGTCTVQKL AHQIYQFTDK DKDNVAPRSK

ISPQGYGRRR RRSLPEAGPG RTLVSSKPQA HGAPAPPSGS APHFL

(Proadrenomedullin N-20 terminal peptide, PAMP):
amino acids 22-41 of preproADM
                                          SEQ ID No.: 32
ARLDVASEF RKKWNKWALS R

(Midregional proAdrenomedullin, MR-proADM):
amino acids 45-92 of preproADM
                                          SEQ ID No.: 33
ELRMSS SYPTGLADVK AGPAQTLIRP QDMKGASRSP EDSSPDAARI

RV

(mature Adrenomedullin (mature ADM); amidated ADM;
bio-ADM): amino acids 95-146-CONH2
                                          SEQ ID No.: 20
YRQSMN NFQGLRSFGC RFGTCTVQKL AHQIYQFTDK DKDNVAPRSK

ISPQGY-CONH2

(Adrenomedullin 1-52-Gly (ADM 1-52-Gly)): amino
acids 95-147 of preproADM
                                          SEQ ID No.: 34
YRQSMN NFQGLRSFGC RFGTCTVQKL AHQIYQFTDK DKDNVAPRSK

ISPQGYG
```

-continued (C-terminal proAdrenomedullin, CT-proADM): amino acids 148-185 of preproADM SEQ ID No.: 35

RRR RRSLPEAGPG RTLVSSKPQA HGAPAPPSGS APHFL

In a specific embodiment of the diagnostic method said proADM and/or fragments thereof having at least 5 amino acids is/are selected from the group comprising mature ADM-$NH_2$ (SEQ ID No. 20), ADM 1-52-Gly (SEQ ID No. 34), MR-proADM (SEQ ID No. 33) and CT-proADM (SEQ ID No. 35).

In a specific embodiment of the diagnostic method either the level of mature ADM-$NH_2$ (SEQ ID No. 20) and/or ADM 1-52-Gly (SEQ ID No. 34)—immunoreactivity or the level of MR-proADM (SEQ ID No. 33) immunoreactivity or the level of CT-proADM (SEQ ID No. 35) immunoreactivity is determined and correlated with the need of said patient for therapy or intervention, wherein said patient is identified as having such a need if the level of mature ADM-$NH_2$ (SEQ ID No. 20) and/or ADM 1-52-Gly (SEQ ID No. 34)-immunoreactivity or the level of MR-proADM (SEQ ID No. 33) immunoreactivity or the level of CT-proADM (SEQ ID No. 35) immunoreactivity in the bodily fluid of said subject is above a threshold.

In a specific embodiment of the diagnostic method the level of proADM and/or fragments thereof is determined by using at least one binder selected from the group: a binder that binds to a region comprised within the following sequence of mature ADM-$NH_2$ (SEQ ID No. 20) and/or ADM1-52-Gly (SEQ ID No. 34) and a second binder that binds to a region comprised within the sequence of mature ADM-$NH_2$ (SEQ ID NO. 20) and/or ADM 1-52-Gly (SEQ ID No. 34).

In a specific embodiment of the diagnostic method the level of proADM and/or fragments thereof is determined by using at least one binder selected from the group: a binder that binds to a region comprised within the sequence of MR-proADM (SEQ ID No. 33) and a second binder that binds to a region comprised within the sequence of MR-proADM (SEQ ID No. 33).

In a specific embodiment of the diagnostic method the level of pro-ADM and/or fragments thereof is determined by using at least one binder selected from the group: a binder that binds to a region comprised within the sequence of CT-proADM (SEQ ID No. 35) and a second binder that binds to a region comprised within the sequence of CT-proADM (SEQ ID No. 35).

Subject matter in a particular embodiment of the present diagnostic method is a method, according to the present invention wherein said fragment may be selected from MR-proADM according to SEQ ID No.: 33 or mature ADM-$NH_2$ according to SEQ ID No.: 20.

Subject matter of the present diagnostic method is a method according to the diagnostic method invention, wherein the level of Pro-Adrenomedullin or fragments thereof of at least 5 amino acids is determined by using a binder to Pro-Adrenomedullin or fragments thereof of at least 5 amino acids.

Subject matter of the present diagnostic method is method, according to the diagnostic method wherein the binder is selected from the group comprising an antibody, an antibody fragment or a non-Ig-Scaffold binding to Pro-Adrenomedullin or fragments thereof of at least 5 amino acids.

A bodily fluid according to the present invention is in one particular embodiment a blood sample. A blood sample may be selected from the group comprising whole blood, serum and plasma. In a specific embodiment of the diagnostic method said sample is selected from the group comprising human citrate plasma, heparin plasma and EDTA plasma.

In a specific embodiment of the invention said anti-ADM antibody or anti-ADM antibody fragment binding to ADM or anti-ADM non-Ig scaffold binding to ADM is for use in intervention and therapy of congestion in a patient according to any embodiment of the invention, wherein said patient is resistant against diuretics or is a non-responder to diuretics therapy.

Another specific embodiment of the invention relates to said anti-adrenomedullin antibody or anti-adrenomedullin antibody fragment or anti-ADM non-Ig scaffold for use in intervention and therapy of congestion in a patient in need thereof, wherein said anti-ADM antibody or anti-ADM fragment or anti-ADM non-Ig scaffold binds to the N-terminal part (aa 1-21) of adrenomedullin:

(SEQ ID No.: 22)

YRQSMNNFQGLRSFGCRFGTC, and wherein said patient is resistant against diuretics or is a non-responder to diuretics therapy.

The term “diuretic resistance” is defined in general as failure to decrease the extracellular fluid volume despite liberal use of diuretics (Ravnan et al. 2002. *CHF* 8.80-85). Epstein et al. defined diuretic resistance as a failure to excrete at least 90 mmol of sodium within 72 hours of a 160-mg oral furosemide dose given twice daily (Epstein et al. 1977. *Curr Ther Res.* 21:656-667).

Adaptation to diuretic drugs and diuretic resistance may be caused by similar mechanisms. Diuretic adaptations can be classified as those that occur during diuretic action, those that cause sodium retention in the short term (causing ‘post-diuretic NaCl retention’), and those that increase sodium retention chronically (the ‘braking phenomenon’). Ways in which kidneys adapt to chronic diuretic treatment are: First, nephron segments downstream from the site of diuretic action increase NaCl reabsorption during diuretic administration because delivered NaCl load is increased. Second, when diuretic concentrations in the tubule decline, the kidney tubules act to retain Na until the next dose of diuretic is administered. Third, the ability of the diuretic to increase renal NaCl excretion declines over time, an effect that results both from depletion of the extracellular fluid volume and from structural and functional changes of kidney tubules themselves. These adaptations all increase the rate of NaCl reabsorption and blunt the effectiveness of diuretic therapy. For rerview see Ellison 1999. *Semin Nephrol.* 19(6):581-97 and De Bruvne 2003. *Postgrad Med J* 79.268-271.

Although difficult to quantify, diuretic resistance is thought to occur in one of three patients with congestive HF. Heart failure represents the most common clinical situation in which diuretic resistance is observed. In mild congestive HF, diuretic resistance is not commonly encountered, as long as renal function is preserved. However, in moderate and severe congestive HF patients, diuretic resistance occurs more frequently and often becomes a clinical problem (Brater 1985. *Drugs* 30:427-443: Taylor 2000 *Cardiol Rev.* 8:104-114).

In a specific embodiment of the diagnostic method, an assay is used for determining the level of proADM and/or fragments thereof having at least 5 amino acids, wherein the assay sensitivity of said assay is able to quantify the mature $ADM-NH_2$ of healthy subjects and is <70 pg/ml, preferably <40 pg/ml and more preferably <10 pg/ml. The before-mentioned concentrations may be used as thresholds for the methods according to the present invention.

In a specific embodiment of the diagnostic method, an assay is used for determining the level of proADM and/or fragments thereof having at least 5 amino acids, wherein the assay sensitivity of said assay is able to quantify MR-proADM of healthy subjects and is <0.5 nmol/L, preferably <0.4 nmol/L and more preferably <0.2 nmol/L. The before-mentioned concentrations may be used as thresholds for the methods according to the present invention.

In a specific embodiment of the diagnostic method, an assay is used for determining the level of proADM and/or fragments thereof having at least 5 amino acids, wherein the assay sensitivity of said assay is able to quantify CT-proADM of healthy subjects and is <100 pmol/L, preferably <75 pmol/L and more preferably <50 pmol/L. The before-mentioned concentrations may be used as thresholds for the methods according to the present invention.

In a specific embodiment of the diagnostic method, said binder exhibits a binding affinity to proADM and/or fragments thereof of at least $10^7$ $M^{-1}$, preferred $10^8$ $M^{-1}$, preferred affinity is greater than $10^9$ $M^{-1}$, most preferred greater than $10^{10}$ $M^{-1}$. A person skilled in the art knows that it may be considered to compensate lower affinity by applying a higher dose of compounds and this measure would not lead out-of-the-scope of the invention.

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare), (Lorenz et al. 2011. *Antimicrob Azents Chemother.* 55 (1.): 165-173).

In a specific embodiment of the diagnostic method, said binder is selected from the group comprising an antibody or an antibody fragment or a non-Ig scaffold binding to proADM and/or fragments thereof.

In a specific embodiment of the diagnostic method, an assay is used for determining the level of proADM and/or fragments thereof having at least 5 amino acids, wherein such assay is a sandwich assay, preferably a fully automated assay.

In one embodiment of the invention it may be a so-called POC-test (point-of-care) that is a test technology, which allows performing the test within less than 1 hour near the patient without the requirement of a fully automated assay system. One example for this technology is the immunochromatographic test technology.

In one embodiment of the diagnostic method such an assay is a sandwich immunoassay using any kind of detection technology including but not restricted to enzyme label, chemiluminescence label, electrochemiluminescence label, preferably a fully automated assay. In one embodiment of the diagnostic method such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, BiomerieuxVidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immuno-chromotography assays.

In a specific embodiment of the diagnostic method, at least one of said two binders is labeled in order to be detected.

Subject matter of the present invention is an anti-adrenomedullin (ADM) antibody or an anti-adrenomedullin antibody fragment or anti-ADM non-Ig scaffold for use in intervention and therapy of congestion in a patient wherein said patient has a disease or condition selected from the group comprising: congestive high blood pressure, swelling or water retention (edema), heart failure in particular acute heart failure, kidney or liver disease.

Subject matter of the present invention is an anti-adrenomedullin (ADM) antibody or an anti-adrenomedullin antibody fragment or anti-ADM non-Ig scaffold for use in intervention and therapy of congestion in a patient wherein said patient has a disease or condition selected from the group comprising: congestive high blood pressure, swelling or water retention (edema), and heart failure, in particular acute heart failure.

Heart failure (HF) is a cardiac condition that occurs, when a problem with the structure or function of the heart impairs its ability to supply sufficient blood flow to meet the body's needs. It can cause a large variety of symptoms, particularly shortness of breath (SOB) at rest or during exercise, signs of fluid retention such as pulmonary congestion or ankle swelling and objective evidence of an abnormality of the structure or function of the heart at rest.

Heart failure is a clinical syndrome characterized by a constellation of symptoms and signs caused by cardiac dysfunction. It is one of the major causes of morbidity and mortality in the developed countries, with a prevalence of 1-2%. Heart failure can be grouped into chronic HF and acute HF. Patients with chronic HF can be grouped into stable chronic HF, worsening signs and symptoms of chronic HF and acute decompensation of chronic HF. Acute heart failure (AHF) is defined as a rapid onset of signs and symptoms of heart failure resulting in the need for urgent therapy or hospitalization. AHF can present as acute de novo HF (new onset of AHF in a patient without previous cardiac dysfunction) or acute decompensation of chronic HF. AHF is the leading cause of hospitalization in adults older than 65 years of age. Despite marked improvements in the prognosis of chronic heart failure patients primarily related to therapeutic advances over the past few decades, both short- and long-term outcomes remain very poor once patients are hospitalized for decompensated heart failure. Nearly 25% of patients hospitalized for AHF need readmission within 30 days of hospital discharge while <50% survive beyond 5 years after hospitalization. In addition to significantly reducing survival and quality of life of affected patients, the monetary burden of AHF on health care systems is enormous. The total cost of heart failure care was estimated to be $31 billion in the US alone in 2012 and majority of this cost is associated with in-hospital care. This cost is projected to increase to an unprecedented $70 billion in 2030 due to ageing of populations.

Heart failure comprises a wide range of patients, from those with normal left ventricular ejection fraction (LVEF) typically considered as ≥50%, also known as HF with preserved EF (HFpEF) to those with reduced LVEF, typically considered as <40%, also known as HF with reduced EF (HFrEF). Patients with an LVEF in the range of 40-49% represent a 'grey area', which is defined as HF with mid-range EF (HFmrEF) (Ponikowski et al. 2016. *European Heart Journal* 18(8): 891-975).

The main goal of AHF treatment in the in-hospital setting is decongestion (removal of excessive intra- and extracellular fluid simply put) and relief of symptoms and signs of congestion. Diuretics remain the main stay decongestive therapy in AHF and almost all hospitalized patients receive this class of drugs. Other classes of medications that increase cardiac output and reduce filling pressure; like inotropes and vasodilators are given in selected groups of patients. Ultrafiltration might also be considered in some patients, particularly in those who do not adequately respond to diuretic therapy.

Although patients (generally) respond well to diuretic therapy, a significant proportion of patients are discharged from hospital without attaining adequate level of decongestion and euvolemic status (i.e. residual congestion). This is primarily related to the fact that current approaches for the clinical assessment of congestion are inadequate. There is consistent evidence indicating that the presence of residual congestion during hospital discharge is associated with worse outcomes post-discharge, particularly hospital readmissions. Hence, there is a huge unmet need for a more accurate and reliable surrogate for congestion which can facilitate objective and optimal decision making regarding the adequacy of level of decongestion attained and timing of hospital discharge.

In a particular aspect of the invention the subject is a subject having heart failure. In another particular aspect of the invention the subject is a subject having acute heart failure and/or a subject having heart failure presenting with worsening signs and/or a subject with symptoms of heart failure or acute heart failure. In one particular aspect of the invention said subject has acute heart failure, that is either new-onset AHF or acute decompensated HF. In another particular aspect of the invention said subject has acute decompensated chronic HF or worsening signs/symptoms of chronic heart failure. In one particular aspect of the invention said subject has acute heart failure in particular new-onset AHF.

The term "acute" is used to mean rapid onset and to describe exacerbated or decompensated heart failure, referring to episodes in which a patient can be characterized as having a change in heart failure signs and symptoms resulting in a need for urgent therapy or hospitalization.

The term "chronic" refers to long duration. Chronic heart failure is a long-term condition, usually kept stable by the treatment of symptoms (stable chronic HF).

Stable chronic HF is characterized by:

1. the presence of structural or functional failure of the heart that impairs its ability to supply sufficient blood flow to meet body's needs,
2. the absence of volume overload (manifested by pulmonary and/or systemic congestion) and/or profound depression of cardiac output (manifested by hypotension, renal insufficiency and/or a shock syndrome), and whereas the patient is not in need of urgent therapy or therapy adjustment and does not require hospitalization.

Chronic HF with worsening signs and symptoms is characterized by:

1. the presence of structural or functional failure of the heart that impairs its ability to supply sufficient blood flow to meet body's needs,
2. volume overload (manifested by pulmonary and/or systemic congestion) and/or profound depression of cardiac output (manifested by hypotension, renal insufficiency and/or a shock syndrome), and whereas the patient is not in need of urgent therapy and does not require hospitalization, but is in need of therapy adjustment.

Chronic heart failure may also decompensate (termed acute decompensated heart failure or acute decompensated chronic heart failure), which is most commonly the result from an intercurrent illness (such as pneumonia), myocardial infarction, arrhythmias, uncontrolled hypertension or a patient's failure to maintain fluid restriction, diet or medication. After treatment, patients with acute decompensated chronic HF may return to a stable chronic compensated status (stable chronic HF).

New onset acute HF and acute decompensated chronic HF are characterized by:

1. the presence of structural or functional failure of the heart that impairs its ability to supply sufficient blood flow to meet body's needs,
2. volume overload (manifested by pulmonary and/or systemic congestion) and/or profound depression of cardiac output (manifested by hypotension, renal insufficiency and/or a shock syndrome), and whereas the patient is in need of urgent therapy or therapy adjustment and does require hospitalization.

| Acute HF | | Chronic HF | |
|---|---|---|---|
| New-onset AHF | Acute decompensated HF = acute decompensated chronic HF | Worsening signs/ symptoms of chronic HF | Stable chronic HF |

The above definitions of acute heart failure that either new-onset AHF or acute decompensated HF or acute decompensated chronic HF or worsening signs/symptoms of chronic heart failure are in line with Voors et al., *European Journal of Heart Failure* (2016). 18, 716-726.

Deterioration of renal function is common in both acute and chronic heart failure (HF) settings lately described as 'cardiorenal syndromes'. Renal congestion (RC) has become increasingly recognized as a potential contributor to cardiorenal syndromes, and adequate control of congestion with simultaneous improvement/preservation of renal function has been proposed as a central goal of patient management in HF (Aronson 2012. *Expert Rev Cardiovasc Ther* 10: 177-189).

Congestion in HF is defined as a high left ventricular diastolic pressure associated with signs and symptoms of HF such as dyspnea, rales, and/or edema. These signs and symptoms related to congestion are the main reasons for HF-related hospitalizations.

Although relief of congestion (and associated signs/symptoms) and attainment of euvolemic status remain the main goal of inhospital AHF therapy, there is no standard algorithm or clinical tool for the assessment of congestion. Current practices regarding the clinical evaluation of congestion revolve around signs and symptoms. Physical examination findings such as elevated jugular venous pressure (JVP), peripheral edema, orthopnea, S3 heart sound and hepatomegaly or chest X-ray findings like cardiomegaly and interstitial/alveolar edema are used as surrogates for congestion. It must be noted that, besides a carefully performed JVP assessment, the predictive value of these parameters for detecting congestion is modest to moderate. There is a high unmet need to have a reliable and accurate surrogate marker for congestion. There is a high and unmet medical need to determining, predicting, assessing and/or monitoring congestion and decongestion in a quantitative and qualitative manner. There is the need to determining, predicting, assessing and/or monitoring the extent of congestion, i.e. the grade of congestion.

For the present invention the extent of congestion may be also expressed as grade severity of congestion and has been determined as described below. However, the person skilled in the art knows that the extent of congestion may be expressed by other scores or surrogates, such as for instance the score utilized by Ambrosy et al. (Ambrosv et al. 2013. *European Heart Journal* 34 (11.): 835-843).

As above explained, congestion can be classified in many different ways. The person skilled in the art knows that the extent of congestion may be expressed by other scores or surrogates. Clinical classification can be based on bedside physical examination in order to detect the presence of clinical symptoms/signs of congestion ('wet' vs. 'dry' if present vs. absent) and/or peripheral hypoperfusion ('cold' vs. 'warm' if present vs. absent) (for review see Ponikowski et al. 2016. *Eur Heart J.* ehw128). The combination of these options identifies four groups: warm and wet (well perfused and congested)—most commonly present; cold and wet (hypoperfused and congested); cold and dry (hypoperfused without congestion); and warm and dry (compensated, well perfused without congestion). This classification may be helpful to guide therapy in the initial phase and carries prognostic information.

Typically, symptoms and signs of AHF reflect fluid overload (pulmonary congestion and/or peripheral edema) or, less often, reduced cardiac output with peripheral hypoperfusion. Chest X-ray can be a useful test for the diagnosis of AHF. Pulmonary venous congestion, pleural effusion, interstitial or alveolar edema and cardiomegaly are the most specific findings for AHF, although in up to 20% of patients with AHF, chest X-ray is nearly normal.

Symptoms/signs of congestion (left-sided) are defined as orthopnoea, paroxysmal nocturnal dyspnoea, pulmonary rales (bilateral), peripheral edema (bilateral). Symptoms/signs of congestion (right-sided) are defined as jugular venous dilatation, peripheral edema (bilateral), congested hepatomegaly, hepatojugular reflux, ascites, symptoms of gut congestion (for review see table 12.2 in Ponikowski et al. 2016 *Eur Heart J.* ehw128).

Edema is an accumulation of fluid in the intercellular tissue that results from an abnormal expansion in interstitial fluid volume. The fluid between the interstitial and intravascular spaces is regulated by the capillary hydrostatic pressure gradient and the oncotic pressure gradient across the capillary (Traves et al. 2013. *Am Fam Physician* 88(2): 102-110). The accumulation of fluid occurs when local or systemic conditions disrupt this equilibrium, leading to increased capillary hydrostatic pressure, increased plasma volume, decreased plasma oncotic pressure (hypoalbuminemia), increased capillary permeability, or lymphatic obstruction.

Clinically, edema manifests as swelling: the amount of interstitial fluid is determined by the balance of fluid homeostasis, and the increased secretion of fluid into the interstitium, or the impaired removal of the fluid can cause edema. A rise in hydrostatic pressure occurs in cardiac failure. Causes of edema which are generalized to the whole body can cause edema in multiple organs and peripherally. For example, severe heart failure can cause pulmonary edema, pleural effusions, ascites and peripheral edema.

Pulmonary edema is fluid accumulation in the air spaces and parenchyma of the lungs. It leads to impaired gas exchange and may cause respiratory failure. It is due to either failure of the left ventricle of the heart to adequately remove blood from the pulmonary circulation ("cardiogenic pulmonary edema"), or an injury to the lung parenchyma or vasculature of the lung ("noncardiogenic pulmonary edema") (Ware and Matthay 2005. *N. Engl. J. Med.* 353 (26): 2788-96). Treatment is focused on three aspects: firstly improving respiratory function, secondly, treating the underlying cause, and thirdly avoiding further damage to the lung. Pulmonary edema, especially acute, can lead to fatal respiratory distress or cardiac arrest due to hypoxia. It is a cardinal feature of congestive heart failure.

The overwhelming symptom of pulmonary edema is difficulty breathing, but may also include coughing up blood (classically seen as pink, frothy sputum), excessive sweating, anxiety, and pale skin. Shortness of breath can manifest as orthopnea (inability to lie down flat due to breathlessness) and/or paroxysmal nocturnal dyspnea (episodes of severe sudden breathlessness at night). These are common presenting symptoms of chronic pulmonary edema due to left ventricular failure. The development of pulmonary edema may be associated with symptoms and signs of "fluid overload"; this is a non-specific term to describe the manifestations of left ventricular failure on the rest of the body and includes peripheral edema (swelling of the legs, in general, of the "pitting" variety, wherein the skin is slow to return to normal when pressed upon), raised jugular venous pressure and hepatomegaly, where the liver is enlarged and may be tender or even pulsatile. Other signs include end-inspiratory crackles (sounds heard at the end of a deep breath) on auscultation and the presence of a third heart sound.

As highlighted previously, clinical surrogates have less than optimal predictive value for the detection of congestion. In the so-called protect study (O'Connor et al. 2012 *European Journal of Heart Failure* 14: 605-612) three of the strongest clinical surrogates of congestion (i.e. JVP, peripheral edema and orthopnea) were combined to enhance accuracy and developed a composite clinical congestion score (CCS) using the scheme presented below:

| Parameter | 0 | 1 | 2 | 3 |
|---|---|---|---|---|
| Peripheral edema | 0 | Ankle | Below knee | Above knee |
| Orthopnea | 0 pillow | 1 pillow | 2 pillows | 3 pillows |
| JVP | <6 cm | 6-10 cm | >10 cm | — |

The score on each of these three parameters were then added to obtain a composite congestion score, which ranged from 0 to 8.

The following algorithm was then utilized to grade severity of congestion:

CCS=0, No clinical congestion

CCS 1-3, Mild clinical congestion

CCS 4-5, Moderate clinical congestion

CCS≥6, Severe clinical congestion

Conditions affecting kidney structure and function can be considered acute or chronic, depending on their duration (chronic kidney disease (CKD), acute kidney disease (AKD) or acute kidney injury (AKI)).

AKD is characterized by structural kidney damage for <3 months and by functional criteria that are also found in AKI, or a GFR of <60 ml/min per 1.73 $m^2$ for <3 months, or a decrease in GFR by ≥35%, or an increase in serum creatinine (SCr) by >50% for <3 months (*Kidney International Supplements. Vol.* 2. *Issue* 1. March 2012. pp. 19-36).

AKI is one of a number of acute kidney diseases and disorders (AKD), and can occur with or without other acute or chronic kidney diseases and disorders.

AKI is defined as reduction in kidney function, including decreased GFR and kidney failure. The criteria for the diagnosis of AKI and the stage of severity of AKI are based on changes in SCr and urine output. In AKI no structural criteria are required (but may exist), but an increase in serum creatinine (SCr) by 50% within 7 days, or an increase by 0.3 mg/dl (26.5 μmol/1), or oliguria is found. AKD may occur in patients with trauma, stroke, sepsis, SIRS, septic shock, acute myocardial infarction (MI), post-MI, local and systemic bacterial and viral infections, autoimmune diseases, burned patients, surgery patients, cancer, liver diseases, lung diseases, as well as in patients receiving nephrotoxins such as cyclosporine, antibiotics including aminoglycosides and anticancer drugs such as cisplatin.

Kidney failure is a stage of AKI and is defined as a GFR<15 ml/min per 1.73 $m^2$ body surface area, or requirement for renal replacement therapy (RRT).

CKD is characterized by a glomerular filtration rate (GFR) of <60 ml/min per 1.73 $m^2$ for >3 months and by kidney damage for >3 months (*Kidney International Supplements,* 2013: Vol 3: 19-62).

Chronic expansion of the extracellular volume is one of the most common and time-honored derangements, which compose the syndromic set of end-stage renal disease (ESRD). Mild-to-moderate degrees of volume expansion may go undetected or are overlooked in ESRD, but marked fluid overload in these patients is eventually a medical emergency demanding hospitalization and extradialyses in these patients. Both, pulmonary congestion and congestive heart failure are common in ESRD (Zoccali et al. 2013 *Blood Purif* 36:184-191).

Liver disease (also called hepatic disease) is a type of damage to or disease of the liver. Liver disease can occur through several mechanisms. A common form of liver disease is viral infection caused by e.g. hepatitis virus. Liver cirrhosis is the formation of fibrous tissue in the place of liver cells that have died due to a variety of causes, including viral hepatitis, alcohol overconsumption, and other forms of liver toxicity that causes chronic liver failure.

Congestive hepatopathy refers to the spectrum of chronic liver injury attributed to passive hepatic congestion arising in the setting of right-sided heart failure or any cause of increased central venous pressure, including severe pulmonary hypertension (Shah and Sass 2015. *Liver Res Open J.* 1(1): 1-10). Cardiohepatic dysfunction is frequent in patients presenting with acute decompensated HF and cardiohepatic syndromes share some common pathophysiological mechanisms with cardiorenal syndromes, such as the increase in venous congestion (Nikolaou et al. 2013. *European Heart Journal* 34: 742-749). End-stage liver disease results in profound salt and water retention. Although most of this fluid retention manifests in the peritoneal cavity as ascites, peripheral edema may become prominent in later stages, particularly when there is severe hypoalbuminemia (Cho and Atwood 2002. *Am J Med.* 113:580-586).

The intervention or therapy of congestion in a patient according to the present invention may be combined with state of the art treatments. Therapy or intervention of congestion according to the state of the art may be selected from the group comprising administration of diuretics, administration of inotropes, administration of vasodilators, ultrafiltration, in particular diuretics.

Furthermore, in one embodiment of the invention an anti-Adrenomedullin (ADM) antibody or an anti-adrenomedullin antibody fragment or an anti-ADM non-Ig scaffold is monospecific.

Monospecific anti-adrenomedullin (ADM) antibody or monospecific anti-adrenomedullin antibody fragment or monospecific anti-ADM non-Ig scaffold means that said antibody or antibody fragment or non-Ig scaffold binds to one specific region encompassing at least 5 amino acids within the target ADM. Monospecific anti-Adrenomedullin (ADM) antibody or monospecific anti-adrenomedullin antibody fragment or monospecific anti-ADM non-Ig scaffold are anti-adrenomedullin (ADM) antibodies or anti-adrenomedullin antibody fragments or anti-ADM non-Ig scaffolds that all have affinity for the same antigen.

In another specific and preferred embodiment the anti-ADM antibody or the anti-ADM antibody fragment or anti-ADM non-Ig scaffold binding to ADM is a monospecific antibody, antibody fragment or non-Ig scaffold, respectively, whereby monospecific means that said antibody or antibody fragment or non-Ig scaffold binds to one specific region encompassing at least 4 amino acids within the target ADM. Monospecific antibodies or fragments or non-Ig scaffolds according to the invention are antibodies or fragments or non-Ig scaffolds that all have affinity for the same antigen. Monoclonal antibodies are monospecific, but monospecific antibodies may also be produced by other means than producing them from a common germ cell.

Said anti-ADM antibody or antibody fragment binding to ADM or non-Ig scaffold binding to ADM may be a non-neutralizing anti-ADM antibody or antibody fragment binding to ADM or non-Ig scaffold binding to ADM.

In a specific embodiment said anti-ADM antibody, anti-ADM antibody fragment or anti-ADM non-Ig scaffold is a non-neutralizing antibody, fragment or non-Ig scaffold. A neutralizing anti-ADM antibody, anti-ADM antibody fragment or anti-ADM non-Ig scaffold would block the bioactivity of ADM to nearly 100%, to at least more than 90%, preferably to at least more than 95%.

In contrast, a non-neutralizing anti-ADM antibody, or anti-ADM antibody fragment or anti-ADM non-Ig scaffold blocks the bioactivity of ADM less than 100%, preferably to less than 95%, preferably to less than 90%, more preferred to less than 80% and even more preferred to less than 50%. This means that bioactivity of ADM is reduced to less than 100%, to 95% or less but not more, to 90% or less but not more, to 80% or less but not more, to 50% or less but not more This means that the residual bioactivity of ADM bound to the non-neutralizing anti-ADM antibody, or anti-ADM antibody fragment or anti-ADM non-Ig scaffold would be more than 0%, preferably more than 5%, preferably more than 10%, more preferred more than 20%, more preferred more than 50%.

In this context (a) molecule(s), being it an antibody, or an antibody fragment or a non-Ig scaffold with "non-neutralizing anti-ADM activity", collectively termed here for simplicity as "non-neutralizing" anti-ADM antibody, antibody fragment, or non-Ig scaffold, that e.g. blocks the bioactivity of ADM to less than 80%, is defined as

- a molecule or molecules binding to ADM, which upon addition to a culture of an eukaryotic cell line, which expresses functional human recombinant ADM receptor composed of CRLR (calcitonin receptor like receptor) and RAMP3 (receptor-activity modifying protein 3), reduces the amount of cAMP produced by the cell line through the action of parallel added human synthetic ADM peptide, wherein said added human synthetic ADM is added in an amount that in the absence of the non-neutralizing antibody to be analyzed, leads to half-maximal stimulation of cAMP synthesis, wherein the reduction of cAMP by said molecule(s) binding to ADM takes place to an extent, which is not more than 80%, even when the non-neutralizing molecule(s) binding to ADM to be analyzed is added in an amount, which is 10-fold more than the amount, which is needed to obtain the maximal reduction of cAMP synthesis obtainable with the non-neutralizing antibody to be analyzed.

The same definition applies to the other ranges; 95%, 90%, 50% etc.

An antibody or fragment according to the present invention is a protein including one or more polypeptides substantially encoded by immunoglobulin genes that specifically binds an antigen. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 Kd or 214 amino acids in length.

Full-length immunoglobulin heavy chains are generally about 50 Kd or 446 amino acid in length. Light chains are encoded by a variable region gene at the $NH_2$-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and $(Fab')_2$, as well as bifunctional hybrid antibodies and single chains (e.g., Lanzavecchia et al. 1987. *Eur. J. Immunol.* 17:105: Huston et al. 1988. *Proc. Nat. Acad. Sci. U.S.A.,* 85:5879-5883: Bird et al. 1988. Science 242:423-426: Hood et al. 1984. *Immunology*, Benjamin. N. Y., 2nd ed.: Hunkapiller and Hood 1986. *Nature* 323:15-16). An immunoglobulin light or heavy chain variable region includes a framework region interrupted by three hypervariable regions, also called complementarity determining regions (CDR's) (see, *Sequences of Proteins of Immunological Interest*, E. Kabat et al. 1983, U.S. Department of Health and Human Services). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g. WO91/17271: WO92/001047: WO92/20791), or selected from a human combinatorial monoclonal antibody library (see the Morphosys website). Human antibodies can also be prepared by using transgenic animals carrying a human immunoglobulin gene (for example, see WO93/12227: WO 91/10741).

Thus, the anti-ADM antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; $F(ab')_2$-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines and numerous others.

Figure 1B:
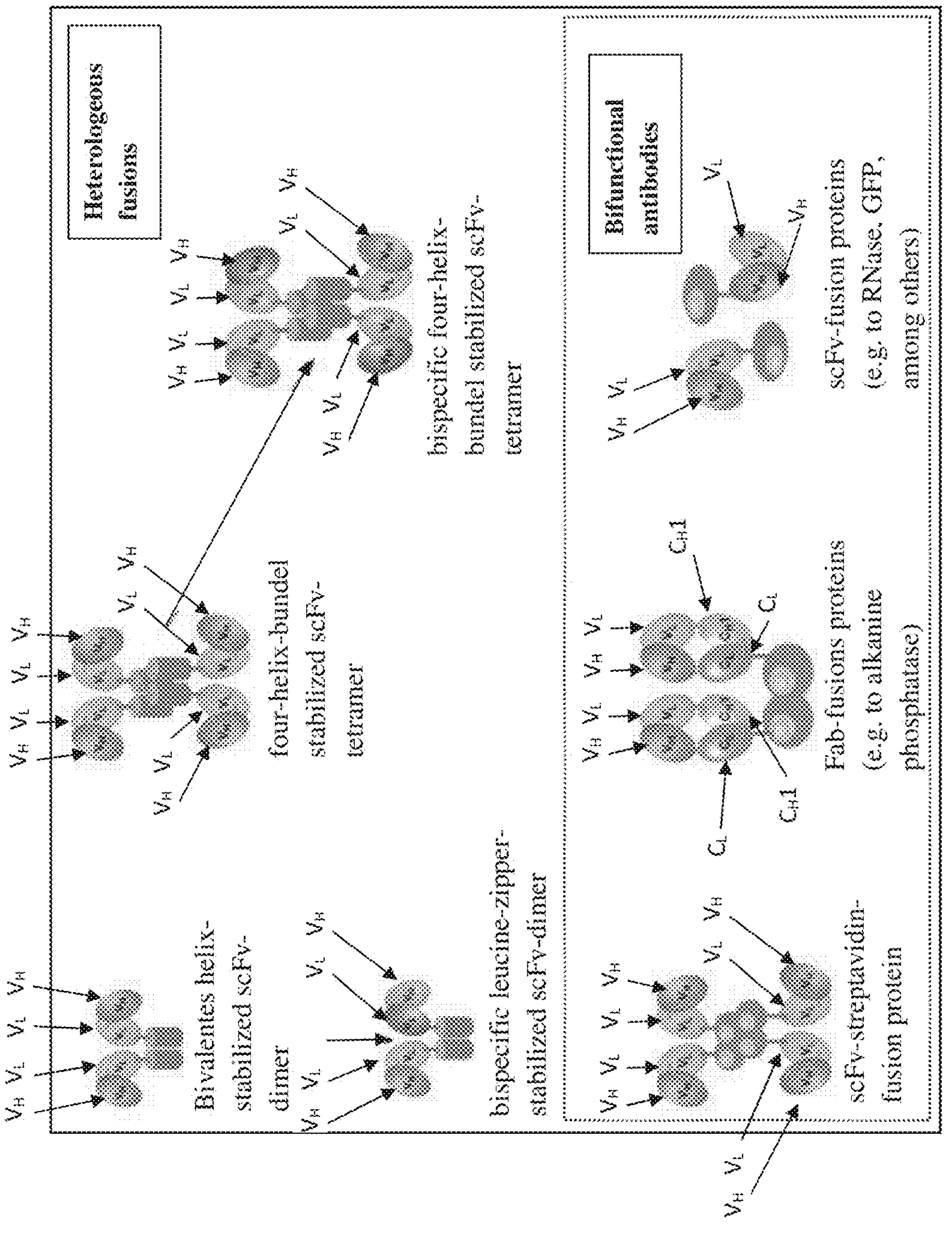
Figure 1C:
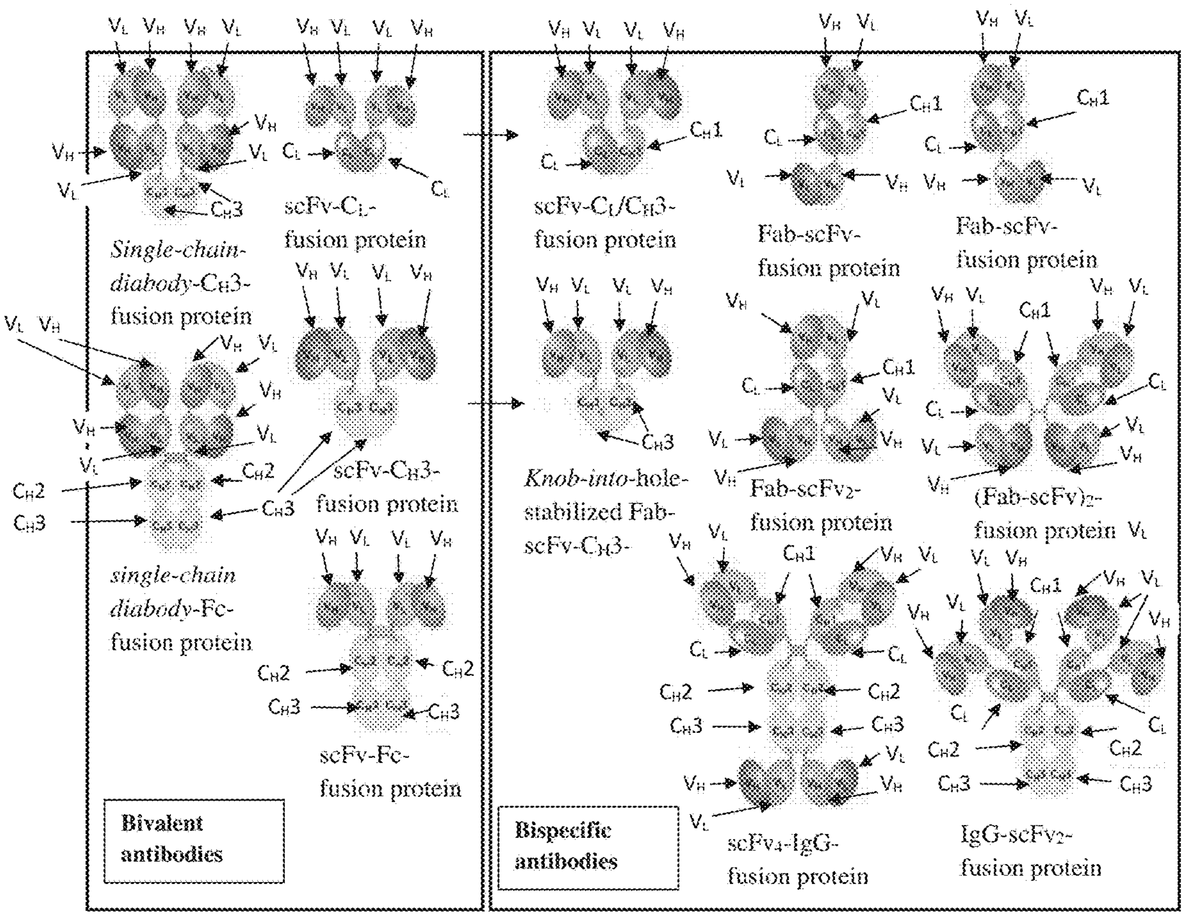
Figure 2A:
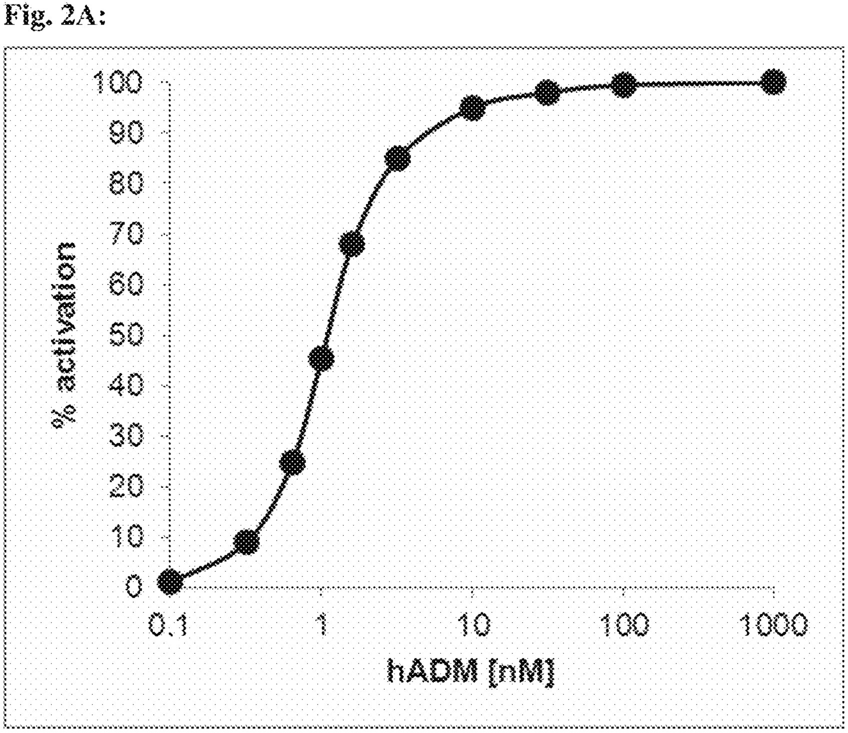
Figure 2B:
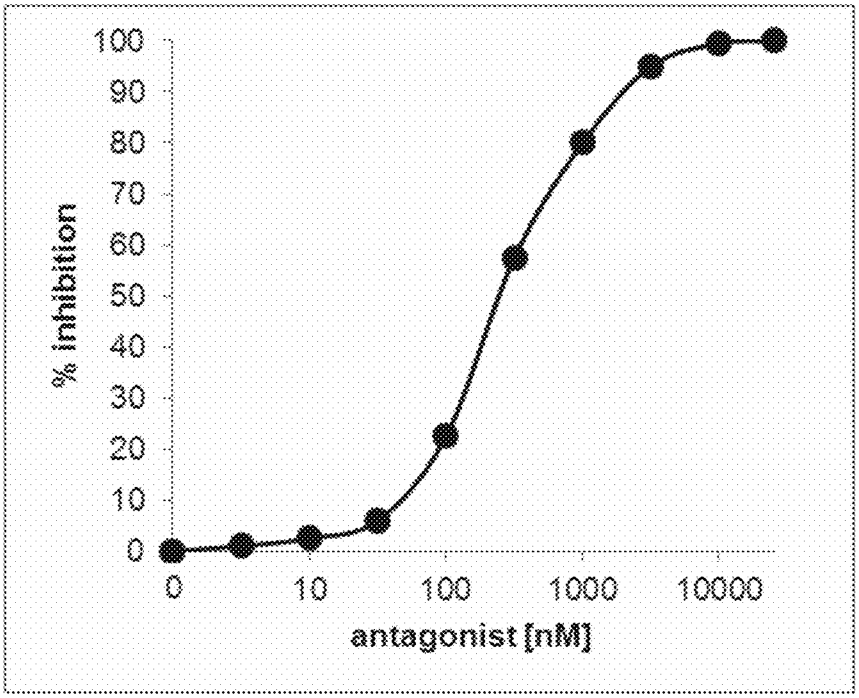
Figure 2C:
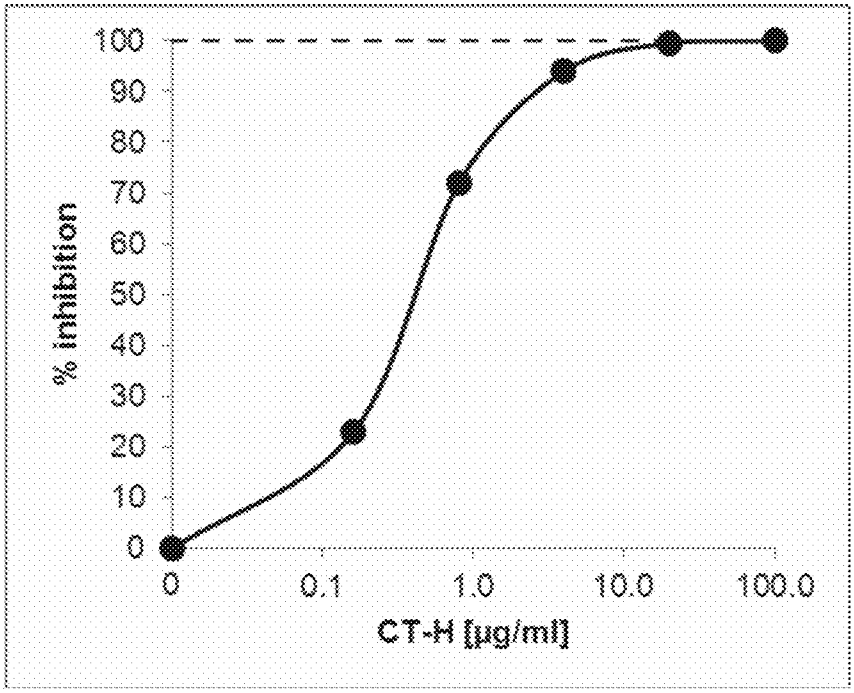
Figure 2D:
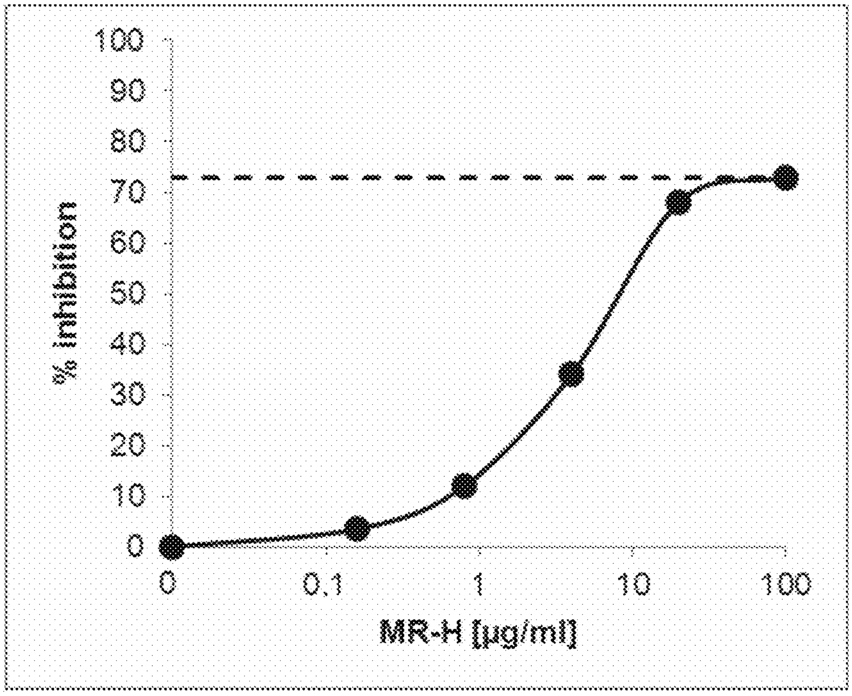
Figure 2E:
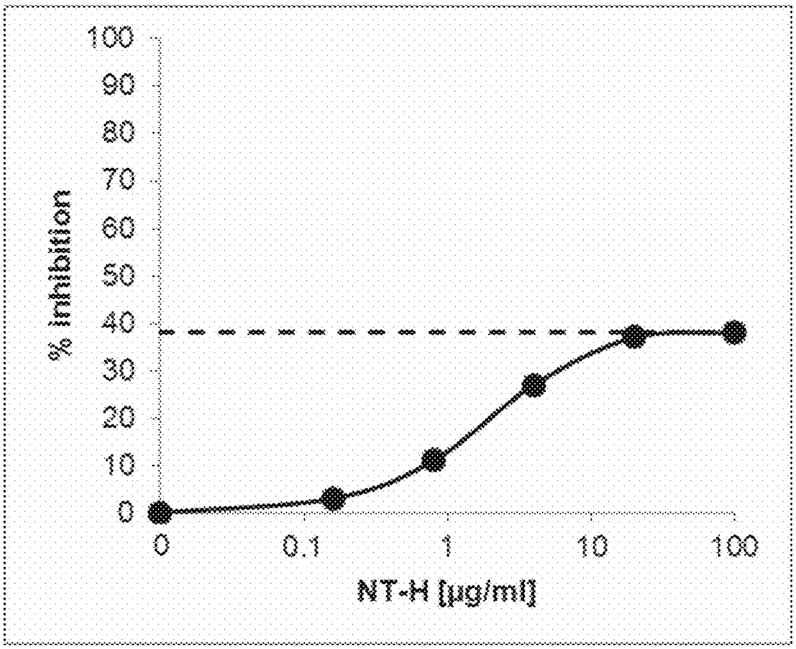
Figure 2F:
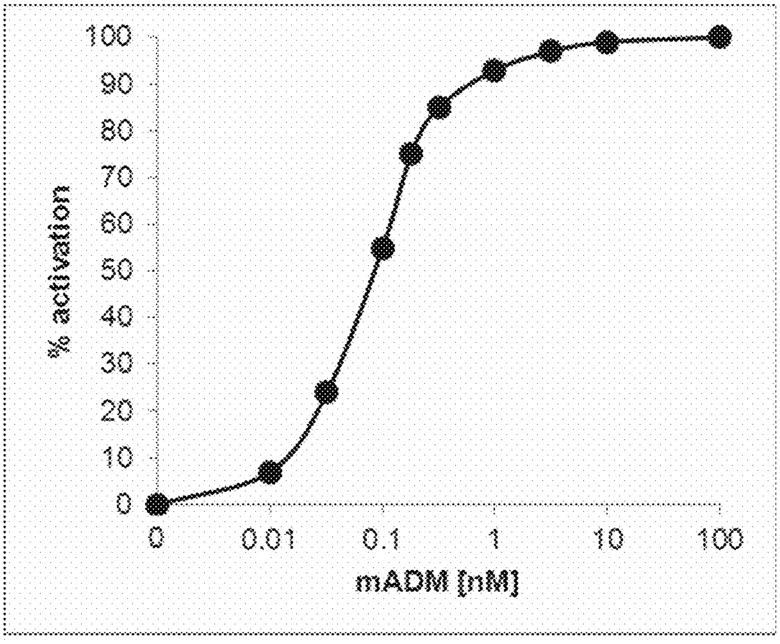
Figure 2G:
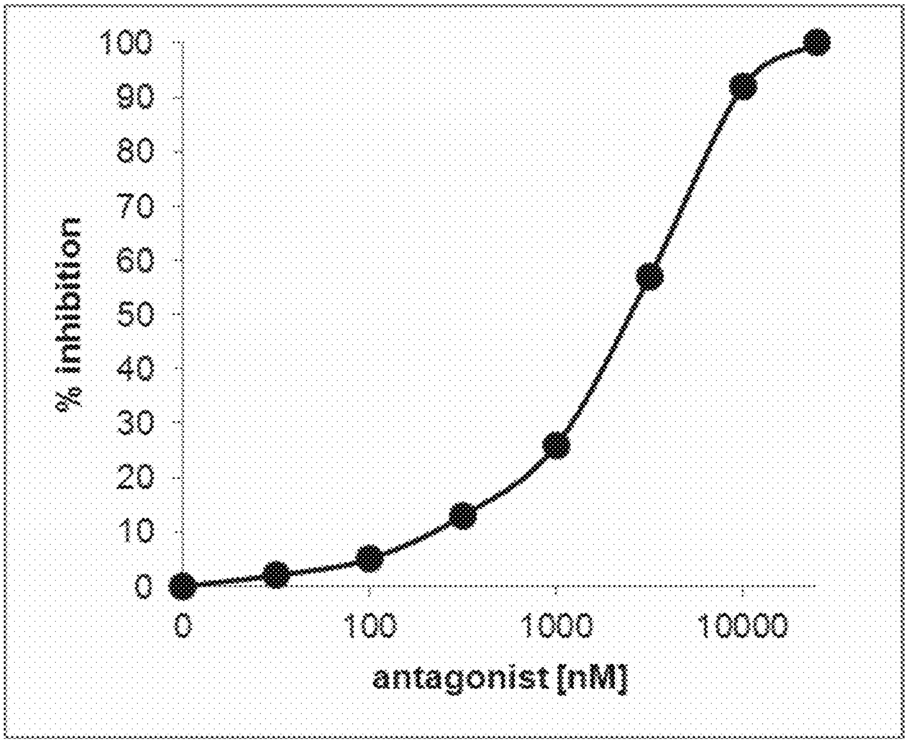
Figure 2H:
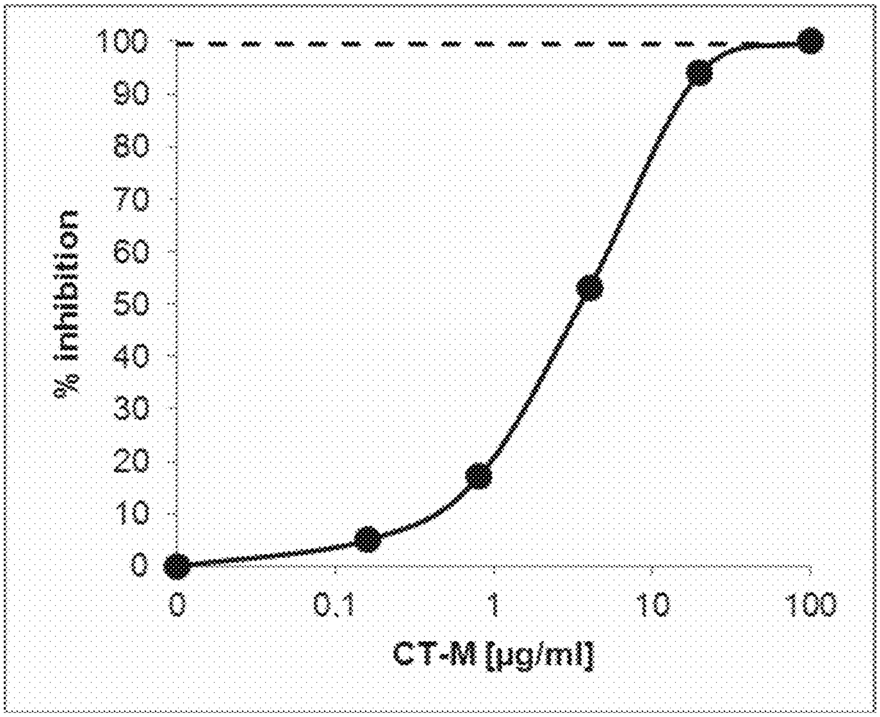
Figure 2I:
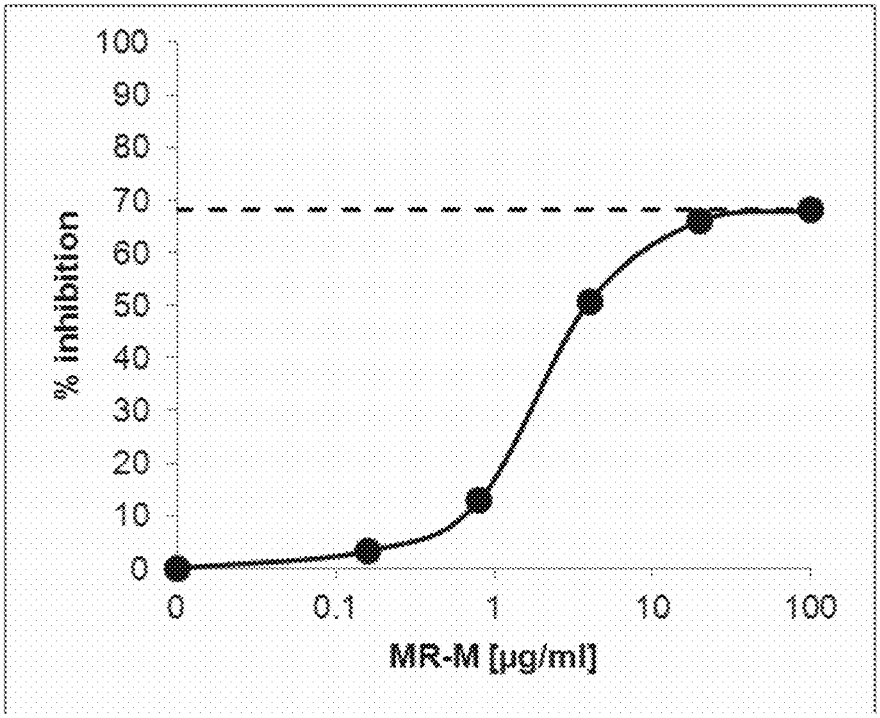
Figure 2J:
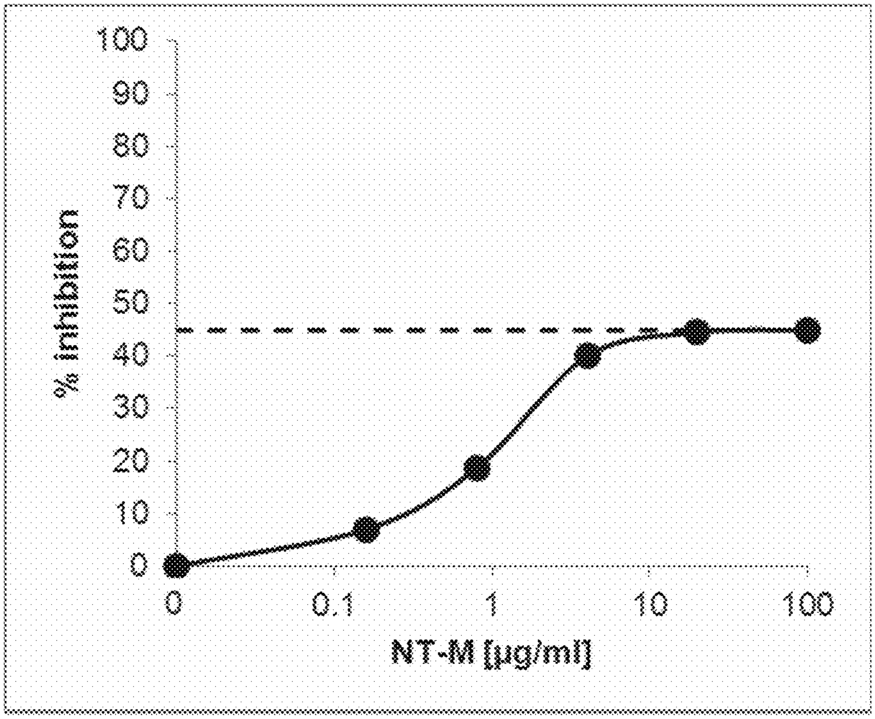
Figure 2K:
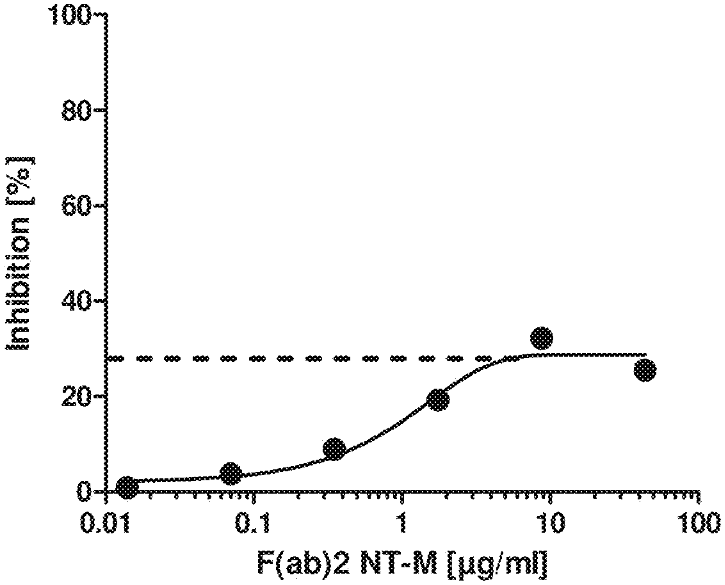
Figure 2L:
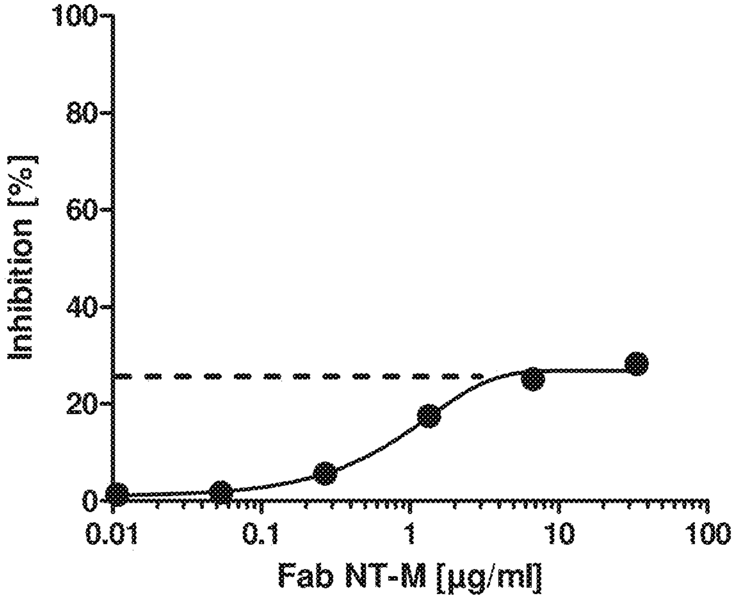

In addition to anti-ADM antibodies other biopolymer scaffolds are well known in the art to complex a target molecule and have been used for the generation of highly target specific biopolymers. Examples are aptamers, spiegelmers, anticalins and conotoxins. For illustration of antibody formats please see FIGS. 1*a*, 1*b* and 1*c*.

In a preferred embodiment the anti-ADM antibody format is selected from the group comprising Fv fragment, scFv fragment, Fab fragment, scFab fragment, F(ab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Non-Ig scaffolds may be protein scaffolds and may be used as antibody mimics as they are capable to bind to ligands or antigens. Non-Ig scaffolds may be selected from the group comprising tetranectin-based non-Ig scaffolds (e.g. described in US2010/0028995), fibronectin scaffolds (e.g. described in EP 1 266 025; lipocalin-based scaffolds (e.g. described in WO 2011/154420); ubiquitin scaffolds (e.g. described in WO 2011/073214), transferrin scaffolds (e.g. described in US 2004/0023334), protein A scaffolds (e.g. described in EP 2 231 860), ankyrin repeat based scaffolds (e.g. described in WO 2010/060748), microproteins preferably microproteins forming a cysteine knot) scaffolds (e.g. described in EP 2314308), Fyn SH3 domain based scaffolds (e.g. described in WO 2011/123685) EGFR-A-domain based scaffolds (e.g. described in WO 2005/040229) and Kunitz domain based scaffolds (e.g. described in EP 1 941 867).

In one embodiment of the invention anti-ADM antibodies according to the present invention may be produced as outlined in Example 1 by synthesizing fragments of ADM as antigens. Thereafter, binder to said fragments are identified using the below described methods or other methods as known in the art.

Humanization of murine antibodies may be conducted according to the following procedure: For humanization of an antibody of murine origin the antibody sequence is analyzed for the structural interaction of framework regions (FR) with the complementary determining regions (CDR) and the antigen. Based on structural modeling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling (Almagro and Fransson 2008. *Humanization of antibodies. Front Biosci.* 2008 Jan. 1; 13:1619-33).

In a preferred embodiment the ADM antibody format is selected from the group comprising Fv fragment, scFv fragment, Fab fragment, scFab fragment, F(ab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is scFab format.

In another preferred embodiment, the anti-ADM antibody, anti-ADM antibody fragment, or anti-ADM non-Ig scaffold is a full length antibody, antibody fragment, or non-Ig scaffold.

In a preferred embodiment the anti-adrenomedullin antibody or an anti-adrenomedullin antibody fragment or anti-ADM non-Ig scaffold is directed to and can bind to an epitope of at least 5 amino acids in length contained in ADM.

In a more preferred embodiment the anti-adrenomedullin antibody or an anti-adrenomedullin antibody fragment or anti-ADM non-Ig scaffold is directed to and can bind to an epitope of at least 4 amino acids in length contained in ADM.

In one specific embodiment of the invention the anti-adrenomedullin (ADM) antibody or anti-ADM antibody fragment binding to adrenomedullin or anti-ADM non-Ig scaffold binding to adrenomedullin is provided for use in therapy or prevention of an acute disease or acute condition of a patient wherein said antibody or fragment or scaffold is not ADM-binding-Protein-1 (complement factor H).

In one specific embodiment of the invention the anti-Adrenomedullin (ADM) antibody or anti-ADM antibody fragment binding to adrenomedullin or anti-ADM non-Ig scaffold binding to adrenomedullin is provided for use in therapy or prevention of an acute disease or acute condition of a patient wherein said antibody or antibody fragment or non-Ig scaffold binds to a region of preferably at least 4, or at least 5 amino acids within the sequence of aa 1-42 of mature human ADM:

```
                                          SEQ ID No.: 23
YRQSMNNFQGLRSFGCRFGTCTVQKLAHQIYQFTDKDKDNVA.
```

In one specific embodiment of the invention the anti-Adrenomedullin (ADM) antibody or anti-ADM antibody fragment binding to adrenomedullin or anti-ADM non-Ig scaffold binding to adrenomedullin is provided for use in therapy or prevention of an acute disease or acute condition of a patient wherein said antibody or fragment or scaffold binds to a region of preferably at least 4, or at least 5 amino acids within the sequence of aa 1-21 of mature human ADM:

```
                                          SEQ ID No.: 22
YRQSMNNFQGLRSFGCRFGTC.
```

In a preferred embodiment of the present invention said anti-ADM antibody or an anti-adrenomedullin antibody fragment or anti-ADM non-Ig scaffold binds to a region or epitope of ADM that is located in the N-terminal part (aa 1-21) of adrenomedullin.

In another preferred embodiment said anti-ADM-antibody or an anti-adrenomedullin antibody fragment or anti-ADM non-Ig scaffold recognizes and binds to a region or epitope within amino acids 1-14 (SEQ ID No.: 25) of adrenomedullin; that means to the N-terminal part (aa 1-14) of adrenomedullin. In another preferred embodiment said anti-ADM-antibody or an anti-adrenomedullin antibody fragment or anti-ADM non-Ig scaffold recognizes and binds to a region or epitope within amino acids 1-10 of adrenomedullin (SEQ ID No.: 26); that means to the N-terminal part (aa 1-10) of adrenomedullin.

```
aa 1-14 of ADM
                         (SEQ ID No.: 25)
YRQSMNNFQGLRSF

aa 1-10 of ADM
                         (SEQ ID No.: 26)
YRQSMNNFQG
```

In another preferred embodiment said anti-ADM antibody or an anti-adrenomedullin antibody fragment or anti-ADM non-Ig scaffold recognizes and binds to a region or epitope within amino acids 1-6 of adrenomedullin (SEQ ID No.: 27); that means to the N-terminal part (aa 1-6) of adrenomedullin. As above stated said region or epitope comprises preferably at least 4 or at least 5 amino acids in length.

```
aa 1-6 of ADM
                                (SEQ ID No.: 27)
YRQSMN
```

In another preferred embodiment said anti-ADM antibody or an anti-adrenomedullin antibody fragment or anti-ADM non-Ig scaffold recognizes and binds to the N-terminal end (aal) of adrenomedullin. N-terminal end means that the amino acid 1, that is “Y” of SEQ ID No. 20, 22 or 23; is mandatory for antibody binding. The antibody or fragment or scaffold would neither bind N-terminal extended nor N-terminal modified Adrenomedullin nor N-terminal degraded adrenomedullin. This means in another preferred embodiment said anti-ADM-antibody or an anti-adrenomedullin antibody fragment or anti-ADM non-Ig scaffold binds only to a region within the sequence of mature ADM if the N-terminal end of ADM is free. In said embodiment the anti-ADM antibody or anti-adrenomedullin antibody fragment or non-Ig scaffold would not bind to a region within the sequence of mature ADM if said sequence is e.g. comprised within pro-ADM.

For the sake of clarity the numbers in brackets for specific regions of ADM like “N-terminal part (aa 1-21)” is understood by a person skilled in the art that the N-terminal part of ADM consists of amino acids 1-21 of the mature ADM sequence.

In another specific embodiment pursuant to the invention the herein provided anti-ADM antibody or anti-ADM antibody fragment or anti-ADM non-Ig scaffold does not bind to the C-terminal portion of ADM, i.e. the aa 43-52 of ADM

```
                                (SEQ ID No.: 24)
PRSKISPQGY-NH2
```

In one specific embodiment it is preferred to use an anti-ADM antibody or an anti-adrenomedullin antibody fragment or anti-ADM non-Ig scaffold according to the present invention, wherein said anti-adrenomedullin antibody or said anti-adrenomedullin antibody fragment or non-Ig scaffold leads to an increase of the ADM level or ADM immunoreactivity in serum, blood, plasma of at least 10%, preferably at least 50%, more preferably >50%, most preferably >100%.

In one specific embodiment it is preferred to use an anti-ADM antibody or an anti-adrenomedullin antibody fragment or anti-ADM non-Ig scaffold according to the present invention, wherein said anti-adrenomedullin antibody or said anti-adrenomedullin antibody fragment or non-Ig scaffold is an ADM stabilizing antibody or an adrenomedullin stabilizing antibody fragment or an adrenomedullin stabilizing non-Ig scaffold that enhances the half-life (tin; half retention time) of adrenomedullin in serum, blood, plasma at least 10%, preferably at least 50%, more preferably >50%, most preferably >100%.

The half-life (half retention time) of ADM may be determined in human semm, blood or plasma in absence and presence of an ADM stabilizing antibody or an adrenomedullin stabilizing antibody fragment or an adrenomedullin stabilizing non-Ig scaffold, respectively, using an immunoassay for the quantification of ADM.

The following steps may be conducted:

ADM may be diluted in human citrate plasma in absence and presence of an ADM stabilizing antibody or an adrenomedullin stabilizing antibody fragment or an adrenomedullin stabilizing non-Ig scaffold, respectively, and may be incubated at 24° C.

Aliquots are taken at selected time points (e.g. within 24 hours) and degradation of ADM may be stopped in said aliquots by freezing at −20° C.

The quantity of ADM may be determined by a hADM immunoassay directly, if the selected assay is not influenced by the stabilizing antibody. Alternatively, the aliquot may be treated with denaturing agents (like HCl) and, after clearing the sample (e.g. by centrifugation) the pH can be neutralized and the ADM-quantified by an ADM immunoassay. Alternatively, non-immunoassay technologies (e.g. RP-HPLC) can be used for ADM-quantification.

The half-life of ADM is calculated for ADM incubated in absence and presence of an ADM stabilizing antibody or an adrenomedullin stabilizing antibody fragment or an adrenomedullin stabilizing non-Ig scaffold, respectively.

The enhancement of half-life is calculated for the stabilized ADM in comparison to ADM that has been incubated in absence of an ADM stabilizing antibody or an adrenomedullin stabilizing antibody fragment or an adrenomedullin stabilizing non-Ig scaffold.

A two-fold increase of the half-life of ADM is an enhancement of half-life of 100%.

Half-life (half retention time) is defined as the period over which the concentration of a specified chemical or drug takes to fall to half its baseline concentration in the specified fluid or blood.

An assay that may be used for the determination of the half-life (half retention time) of adrenomedullin in serum, blood, plasma is described in Example 3.

In a preferred embodiment said anti-ADM antibody, anti-ADM antibody fragment or anti-ADM non-Ig scaffold is a non-neutralizing antibody, fragment or scaffold. A neutralizing anti-ADM antibody, anti-ADM antibody fragment or anti-ADM non-Ig scaffold would block the bioactivity of ADM to nearly 100%, to at least more than 90%, preferably to at least more than 95%. In other words this means that said non-neutralizing anti-ADM antibody, anti-ADM antibody fragment or anti-ADM non-Ig scaffold blocks the bioactivity of ADM to less than 100%, preferably less than 95% preferably less than 90%. In an embodiment wherein said non-neutralizing anti-ADM antibody, anti-ADM antibody fragment or anti-ADM non-Ig scaffold blocks the bioactivity of ADM to less than 95% an anti-ADM antibody, anti-ADM antibody fragment or anti-ADM non-Ig scaffold that would block the bioactivity of ADM to more than 95% would be outside of the scope of said embodiment. This means in one embodiment that the bioactivity is reduced to 95% or less but not more, preferably to 90% or less, more preferably to 80% or less, more preferably to 50% or less but not more.

In one embodiment of the invention the non-neutralizing antibody is an antibody binding to a region of at least 5 amino acids within the sequence of aa 1-42 of mature human ADM (SEQ ID No.: 23), preferably within the sequence aa 1-32 of mature human ADM (SEQ ID No.: 28), or an antibody binding to a region of at least 5 amino acids within the sequence of aa 1-40 of mature murine ADM (SEQ ID No.: 29), preferably within the sequence aa 1-31 of mature murine ADM (SEQ ID No.: 30).

In another preferred embodiment of the invention the non-neutralizing antibody is an antibody binding to a region of at least 4 amino acids within the sequence of aa 1-42 of mature human ADM (SEQ ID No.: 23), preferably within the sequence aa 1-32 of mature human ADM (SEQ ID No.: 28), or an antibody binding to a region of at least 4 amino acids within the sequence of aa 1-40 of mature murine ADM (SEQ ID No.: 29), preferably within the sequence aa 1-31 of mature murine ADM (SEQ ID No.: 30).

```
aa 1-32 human mature human ADM
                                       (SEQ ID No.: 28)
YRQSMNNFQGLRSFGCRFGTCTVQKLAHQIYQ

aa 1-40 mature murine ADM
                                       (SEQ ID No.: 29)
YRQSMNQGSRSNGCRFGTCTFQKLAHQIYQLTDKDKDGMA

aa 1-31 mature murine ADM
                                       (SEQ ID No.: 30)
YRQSMNQGSRSNGCRFGTCTFQKLAHQIYQL
```

In a specific embodiment according to the present invention an non-neutralizing anti-ADM antibody or an anti-adrenomedullin antibody fragment or ADM non-Ig scaffold is used, wherein said anti-ADM antibody or an anti-adrenomedullin antibody fragment blocks the bioactivity of ADM to less than 80%, preferably less than 50% (of baseline values). It has to be understood that said limited blocking of the bioactivity (meaning reduction of the bioactivity) of ADM occurs even at excess concentration of the antibody, fragment or scaffold, meaning an excess of the antibody, fragment or scaffold in relation to ADM. Said limited blocking is an intrinsic property of the ADM binder itself in said specific embodiment. This means that said antibody, fragment or scaffold has a maximal inhibition of 80% or 50% respectively. In a preferred embodiment said anti-ADM antibody, anti-ADM antibody fragment or anti-ADM non-Ig scaffold would block the bioactivity/reduce the bioactivity of anti-ADM to at least 5%. The stated above means that approximately 20% or 50% or even 95% residual ADM bioactivity remains present, respectively.

Thus, in accordance with the present invention the provided anti-ADM antibodies, anti-ADM antibody fragments, and anti-ADM non-Ig scaffolds do not neutralize the respective ADM bioactivity.

The bioactivity is defined as the effect that a substance takes on a living organism or tissue or organ or functional unit in vivo or in vitro (e.g. in an assay) after its interaction. In case of ADM bioactivity this may be the effect of ADM in a human recombinant Adrenomedullin receptor cAMP functional assay. Thus, according to the present invention bioactivity is defined via an Adrenomedullin receptor cAMP functional assay. The following steps may be performed in order to determine the bioactivity of ADM in such an assay:

- Dose response curves are performed with ADM in said human recombinant Adrenomedullin receptor cAMP functional assay.
- The ADM-concentration of half-maximal cAMP stimulation may be calculated.
- At constant half-maximal cAMP-stimulating ADM-concentrations dose response curves (up to 100 μg/ml final concentration) are performed by an ADM stabilizing antibody or an adrenomedullin stabilizing antibody fragment or an adrenomedullin stabilizing non-Ig scaffold, respectively.

A maximal inhibition in said ADM bioassay of 50% means that said anti-ADM antibody or said anti-adrenomedullin antibody fragment or said anti-adrenomedullin non-Ig scaffold, respectively, blocks the bioactivity of ADM to 50% of baseline values. A maximal inhibition in said ADM bioassay of 80% means that said anti-ADM antibody or said anti-adrenomedullin antibody fragment or said anti-adrenomedullin non-Ig scaffold, respectively, blocks the bioactivity of ADM to 80%. This is in the sense of blocking the ADM bioactivity to not more than 80%. This means approximately 20% residual ADM bioactivity remains present.

However, by the present specification and in the above context the expression "blocks the bioactivity of ADM" in relation to the herein disclosed anti-ADM antibodies, anti-ADM antibody fragments, and anti-ADM non-Ig scaffolds should be understood as mere decreasing the bioactivity of ADM from 100% to 20% remaining ADM bioactivity at maximum, preferably decreasing the ADM bioactivity from 100% to 50% remaining ADM bioactivity; but in any case there is ADM bioactivity remaining that can be determined as detailed above.

The bioactivity of ADM may be determined in a human recombinant Adrenomedullin receptor cAMP functional assay (Adrenomedullin Bioassay) according to Example 2.

In a preferred embodiment a modulating antibody or a modulating anti-adrenomedullin antibody fragment or a modulating anti-adrenomedullin non-Ig scaffold is used in therapy or prevention of a chronic or acute disease or acute condition of a patient for stabilizing the circulation, in particular stabilizing the systemic circulation.

A "modulating" anti-ADM antibody or a modulating anti-adrenomedullin antibody fragment or a modulating anti-adrenomedullin non-Ig scaffold is an antibody or an anti-adrenomedullin antibody fragment or non-Ig scaffold that enhances the half-life (tin half retention time) of adrenomedullin in serum, blood, plasma at least 10%, preferably at least, 50%, more preferably >50%, most preferably >100% and blocks the bioactivity of ADM to less than 80%, preferably less than 50% and said anti-ADM antibody, anti-ADM antibody fragment or anti-ADM non-Ig scaffold would block the bioactivity of ADM to at least 5%. These values related to half-life and blocking of bioactivity have to be understood in relation to the before-mentioned assays in order to determine these values. This is in the sense of blocking the ADM bioactivity of not more than 80% or not more than 50%, respectively.

Such a modulating anti-ADM antibody or a modulating anti-adrenomedullin antibody fragment or a modulating anti-adrenomedullin non-Ig scaffold offers the advantage that the dosing of the administration is facilitated. The combination of partially blocking or partially reducing Adrenomedullin bioactivity and increase of the in vivo half-life (increasing the Adrenomedullin bioactivity) leads to beneficial simplicity of anti-adrenomedullin antibody or an anti-adrenomedullin antibody fragment or anti-adrenomedullin non-Ig scaffold dosing. In a situation of excess of endogenous Adrenomedullin (maximal stimulation, late sepsis phase, shock, hypodynamic phase) the activity lowering effect is the major impact of the antibody or fragment or scaffold, limiting the (negative) effect of Adrenomedullin. In case of low or normal endogenous Adrenomedullin concentrations, the biological effect of anti-adrenomedullin antibody or an anti-adrenomedullin antibody fragment or anti-ADM non-Ig scaffold is a combination of lowering (by partially blocking) and increase by increasing the Adrenomedullin half-life. Thus, the non-neutralizing and modulating anti-adrenomedullin antibody or anti-adrenomedullin antibody fragment or anti-adrenomedullin non-Ig scaffold acts like an ADM bioactivity buffer in order to keep the bioactivity of ADM within a certain physiological range.

In a specific embodiment of the invention the antibody is a monoclonal antibody or a fragment thereof. In one embodiment of the invention the anti-ADM antibody or the anti-ADM antibody fragment is a human or humanized antibody or derived therefrom. In one specific embodiment one or more (murine) CDR's are grafted into a human antibody or antibody fragment.

Subject matter of the present invention in one aspect is a human CDR-grafted antibody or antibody fragment thereof that binds to ADM, wherein the human CDR-grafted antibody or antibody fragment thereof comprises an antibody heavy chain (H chain) comprising:

```
                                 SEQ ID No.: 1
GYTFSRYW

                                 SEQ ID No.: 2
ILPGSGST
and/or

                                 SEQ ID No.: 3
TEGYEYDGFDY
```

and/or further comprises an antibody light chain (L chain) comprising:

```
                                 SEQ ID No.: 4
QSIVYSNGNTY
```

SEQUENCE "RVS" (not part of the Sequencing listing):

```
RVS
and/or

                                 SEQ ID No.: 5
FQGSHIPYT.
```

In one specific embodiment of the invention subject matter of the present invention is a human monoclonal antibody that binds to ADM or an antibody fragment thereof that binds to ADM wherein the heavy chain comprises at least one CDR selected from the group comprising:

```
                                 SEQ ID No.: 1
GYTFSRYW

                                 SEQ ID No.: 2
ILPGSGST

                                 SEQ ID No.: 3
TEGYEYDGFDY
```

and wherein the light chain comprises at least one CDR selected from the group comprising:

```
                                 SEQ ID No.: 4
QSIVYSNGNTY
```

SEQUENCE "RVS" (not part of the Sequencing Listing):

```
RVS

                                 SEQ ID No.: 5
FQGSHIPYT.
```

In a more specific embodiment of the invention subject matter of the invention is a human monoclonal antibody that binds to ADM or an antibody fragment thereof that binds to ADM wherein the heavy chain comprises the sequences:

```
                                 SEQ ID No.: 1
GYTFSRYW

                                 SEQ ID No.: 2
ILPGSGST

                                 SEQ ID No.: 3
TEGYEYDGFDY
```

and wherein the light chain comprises the sequences:

```
                                 SEQ ID No.: 4
QSIVYSNGNTY
```

SEQUENCE "RVS" (not part of the Sequencing listing):

```
RVS

                                 SEQ ID No.: 5
FQGSHIPYT.
```

In a very specific embodiment the anti-ADM antibody has a sequence selected from the group comprising: SEQ ID No. 6, 7, 8, 9, 10, 11, 12, and 13.

The anti-ADM antibody or anti-adrenomedullin antibody fragment or anti-ADM non-Ig scaffold according to the present invention exhibits an affinity towards human ADM in such that affinity constant is greater than $10^{-7}$ M, preferred $10^{-8}$M, preferred affinity is greater than $10^{-9}$ M, most preferred higher than $10^{-10}$ M. A person skilled in the art knows that it may be considered to compensate lower affinity by applying a higher dose of compounds and this measure would not lead out-of-the-scope of the invention. The affinity constants may be determined according to the method as described in Example 1.

Subject matter of the present invention is a human monoclonal antibody or fragment that binds to ADM or an antibody fragment thereof for use in intervention and therapy of congestion in a patient according to the present invention, wherein said antibody or fragment comprises a sequence selected from the group comprising:

```
(AM-VH-C)
                                 SEQ ID NO: 6
QVQLQQSGAELMKPGASVKISCKATGYTFSRYWIE

WVKQRPGHGLEWIGEILPGSGSTNYNEKFKGKATI

TADTSSNTAYMQLSSLTSEDSAVYYCTEGYEYDGF

DYWGQGTTLTVSSASTKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKRVEPKHHHHHH

(AM-VH1)
                                 SEQ ID NO: 7
QVQLVQSGAEVKKPGSSVKVSCKASGYTFSRYWIS

WVRQAPGQGLEWMGRILPGSGSTNYAQKFQGRVTI

TADESTSTAYMELSSLRSEDTAVYYCTEGYEYDGF

DYWGQGTTVTVSSASTKGPSVFPLAPSSKSTSGGT
```

-continued

AALGCLVKDYFPEPVTVSWNSGALTSGVHTFPAVL

QSSGLYSLSSVVTVPSSSLGTQTYICNVNHKPSNT

KVDKRVEPKHHHHHH (AM-VH2-E40)
SEQ ID NO: 8
QVQLVQSGAEVKKPGSSVKVSCKASGYTFSRYWIE

WVRQAPGQGLEWMGRILPGSGSTNYAQKFQGRVTI

TADESTSTAYMELSSLRSEDTAVYYCTEGYEYDGF

DYWGQGTTVTVSSASTKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKRVEPKHHHHHH (AM-VH3-T26-E55)
SEQ ID NO: 9
QVQLVQSGAEVKKPGSSVKVSCKATGYTFSRYWIS

WVRQAPGQGLEWMGEILPGSGSTNYAQKFQGRVTI

TADESTSTAYMELSSLRSEDTAVYYCTEGYEYDGF

DYWGQGTTVTVSSASTKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKRVEPKHHHHHH (AM-VH4-T26-E40-E55)
SEQ ID NO: 10
QVQLVQSGAEVKKPGSSVKVSCKATGYTFSRYWIE

WVRQAPGQGLEWMGEILPGSGSTNYAQKFQGRVTI

TADESTSTAYMELSSLRSEDTAVYYCTEGYEYDGF

DYWGQGTTVTVSSASTKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKRVEPKHHHHHH (AM-VL-C)
SEQ ID NO: 11
DVLLSQTPLSLPVSLGDQATISCRSSQSIVYSNGN

TYLEWYLQKPGQSPKLLIYRVSNRFSGVPDRFSGS

GSGTDFTLKISRVEAEDLGVYYCFQGSHIPYTFGG

GTKLEIKRTVAAPSVFIFPPSDEQLKSGTASVVCL

LNNFYPREAKVQWKVDNALQSGNSQESVTEQDSKD

STYSLSSTLTLSKADYEKHKVYACEVTHQGLSSPV

TKSFNRGEC (AM-VL1)
SEQ ID NO: 12
DVVMTQSPLSLPVTLGQPASISCRSSQSIVYSNGN

TYLNWFQQRPGQSPRRLIYRVSNRDSGVPDRFSGS

GSGTDFTLKISRVEAEDVGVYYCFQGSHIPYTFGQ

GTKLEIKRTVAAPSVFIFPPSDEQLKSGTASVVCL

LNNFYPREAKVQWKVDNALQSGNSQESVTEQDSKD

-continued

STYSLSSTLTLSKADYEKHKVYACEVTHQGLSSPV

TKSFNRGEC (AM-VL2-E40)
SEQ ID NO: 13
DVVMTQSPLSLPVTLGQPASISCRSSQSIVYSNGN

TYLEWFQQRPGQSPRRLIYRVSNRDSGVPDRFSGS

GSGTDFTLKISRVEAEDVGVYYCFQGSHIPYTFGQ

GTKLEIKRTVAAPSVFIFPPSDEQLKSGTASVVCL

LNNFYPREAKVQWKVDNALQSGNSQESVTEQDSKD

STYSLSSTLTLSKADYEKHKVYACEVTHQGLSSPV

TKSFNRGEC

Subject matter of the present invention is a pharmaceutical formulation for use in intervention and therapy of congestion in a patient comprising an antibody or fragment or scaffold according to the present invention.

Subject matter of the present invention is a pharmaceutical formulation for use in intervention and therapy of congestion in a patient comprising an antibody or fragment or scaffold according to the present invention wherein said patient has a disease or condition selected from the group comprising: congestive high blood pressure, swelling or water retention (edema), heart failure in particular acute heart failure, kidney or liver disease.

Subject matter of the present invention is a pharmaceutical formulation for use in intervention and therapy of congestion in a patient according to the present invention wherein said pharmaceutical formulation is a solution, preferably a ready-to-use solution.

Subject matter of the present invention is a pharmaceutical formulation for use in intervention and therapy of congestion in a patient according to the present invention wherein said pharmaceutical formulation is in a freeze-dried state.

Subject matter of the present invention is a pharmaceutical formulation for use in intervention and therapy of congestion in a patient according to the present invention, wherein said pharmaceutical formulation is administered intra-muscular.

Subject matter of the present invention is a pharmaceutical formulation for use in intervention and therapy of congestion in a patient according to the present invention, wherein said pharmaceutical formulation is administered intra-vascular.

Subject matter of the present invention is a pharmaceutical formulation for use in intervention and therapy of congestion in a patient according to the present invention, wherein said pharmaceutical formulation is administered via infusion.

Subject matter of the present invention is a pharmaceutical formulation for use in intervention and therapy of congestion in a patient according to the present invention, wherein said pharmaceutical formulation is to be administered systemically.

The following embodiments are subject of the present invention:

1. Anti-adrenomedullin (ADM) antibody or an anti-adrenomedullin antibody fragment or anti-ADM non-Ig scaffold for use in intervention and therapy of congestion in a patient in need thereof.

2. Anti-adrenomedullin (ADM) antibody or an anti-adrenomedullin antibody fragment or anti-ADM non-Ig scaffold for use in intervention and therapy of congestion in a patient according to item 1 wherein said patient has a disease or condition selected from the group comprising: congestive high blood pressure, swelling or water retention (edema), heart failure in particular acute heart failure, kidney or liver disease.
3. Anti-adrenomedullin (ADM) antibody or an anti-adrenomedullin antibody fragment or anti-ADM non-Ig scaffold for use in intervention and therapy of congestion in a patient according to items 1 or 2 wherein said patient has a disease or condition selected from the group comprising: congestive high blood pressure, swelling or water retention (edema), and heart failure, in particular acute heart failure.
4. Anti-Adrenomedullin (ADM) antibody or an anti-ADM antibody fragment binding to adrenomedullin or anti-ADM non-Ig scaffold binding to adrenomedullin for use in intervention and therapy of congestion in a patient according to any of items 1 to 3, wherein said antibody or antibody fragment or non-Ig scaffold is monospecific.
5. Anti-Adrenomedullin (ADM) antibody or an anti-ADM antibody fragment binding to adrenomedullin or anti-ADM non-Ig scaffold binding to adrenomedullin for use in intervention and therapy of congestion in a patient according to any of items 1 to 4, wherein said antibody or fragment or scaffold exhibits a binding affinity to ADM of at least $10^{-7}$ M.
6. Anti-Adrenomedullin (ADM) antibody or an anti-ADM antibody fragment binding to adrenomedullin or anti-ADM non-Ig scaffold binding to adrenomedullin for use in intervention and therapy of congestion in a patient according to any of items 1 to 5, wherein said antibody or antibody fragment or non-Ig scaffold binds to a region of preferably at least 4, or at least 5 amino acids within the sequence of aa 1-42 of mature human ADM:

(SEQ ID No.: 23)
YRQSMNNFQGLRSFGCRFGTCTVQKLAHQIYQFTD

KDKDNVA.

7. Anti-ADM antibody or an anti-adrenomedullin antibody fragment or an anti-ADM non-Ig scaffold for use in intervention and therapy of congestion in a patient to according any of items 1 to 6 wherein said antibody or fragment or scaffold binds to the N-terminal part (aa 1-21) of adrenomedullin:

(SEQ ID No.: 22)
YRQSMNNFQGLRSFGCRFGTC.

8. Anti-ADM antibody or an anti-adrenomedullin antibody fragment or an anti-ADM non-Ig scaffold for use in intervention and therapy of congestion in a patient according to any of items 1 to 7, wherein said antibody or fragment or scaffold recognizes and binds to the N-terminal end (aa 1) of adrenomedullin.
9. Anti-Adrenomedullin (ADM) antibody or an anti-ADM antibody fragment binding to adrenomedullin or anti-ADM non-Ig scaffold binding to adrenomedullin for use in intervention and therapy of congestion in a patient according to any of items 1 to 8, characterized in that said antibody, antibody fragment or non-Ig scaffold does not bind to the C-terminal portion of ADM, having the sequence aa 43-52 of ADM (SEQ ID NO: 24)
PRSKISPQGY-$NH_2$.

10. Anti-ADM antibody or an anti-adrenomedullin antibody fragment or an anti-ADM non-Ig scaffold for use in intervention and therapy of congestion in a patient according to any of items 1 to 9, wherein said antibody or fragment or scaffold blocks the bioactivity of ADM not more than 80%, preferably not more than 50%,
11. Anti-ADM antibody or an anti-adrenomedullin antibody fragment or an anti-ADM non-Ig scaffold for use in intervention and therapy of congestion in a patient according to any of items 1 to 10, wherein said patient is an ICU patient.
12. Anti-ADM antibody or an anti-adrenomedullin antibody fragment for use in intervention and therapy of congestion in a patient according to any of items 1 to 11, wherein said antibody or fragment is a human monoclonal antibody or fragment that binds to ADM or an antibody fragment thereof wherein the heavy chain comprises the sequences:

SEQ ID NO: 1
GYTFSRYW

SEQ ID NO: 2
ILPGSGST

SEQ ID NO: 3
TEGYEYDGFDY and wherein the light chain comprises the sequences:

SEQ ID NO: 4
QSIVYSNGNTY

SEQUENCE "RVS" (not part of the Sequencing Listing):

RVS

SEQ ID NO: 5
FQGSHIPYT.

13. A human monoclonal antibody or fragment that binds to ADM or an antibody fragment thereof for use in intervention and therapy of congestion in a patient according to item 12, wherein said antibody or fragment comprises a sequence selected from the group comprising:

(AM-VH-C)
SEQ ID NO: 6
QVQLQQSGAELMKPGASVKISCKATGYTFSRYWIEWVKQRPGHGLEWIGEI

LPGSGSTNYNEKFKGKATITADTSSNTAYMQLSSLTSEDSAVYYCTEGYEY

DGFDYWGQGTTLTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRVEPKHHHHHH

-continued (AM-VH1)

SEQ ID NO: 7

QVQLVQSGAEVKKPGSSVKVSCKASGYTFSRYWISWVRQAPGQGLEWMGRI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VH2-E40)

SEQ ID NO: 8

QVQLVQSGAEVKKPGSSVKVSCKASGYTFSRYWIEWVRQAPGQGLEWMGRI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VH3-T26-E55)

SEQ ID NO: 9

QVQLVQSGAEVKKPGSSVKVSCKATGYTFSRYWISWVRQAPGQGLEWMGEI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VH4-T26-E40-E55)

SEQ ID NO: 10

QVQLVQSGAEVKKPGSSVKVSCKATGYTFSRYWIEWVRQAPGQGLEWMGEI
LPGSGSTNYAQKFQGRVTITADESTSTAYMELSSLRSEDTAVYYCTEGYEY
DGFDYWGQGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKRVEPKHHHHHH (AM-VL-C)

SEQ ID NO: 11

DVLLSQTPLSLPVSLGDQATISCRSSQSIVYSNGNTYLEWYLQKPGQSPKL
LIYRVSNRFSGVPDRFSGSGSGTDFTLKISRVEAEDLGVYYCFQGSHIPYT
FGGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQ
GLSSPVTKSFNRGEC (AM-VL1)

SEQ ID NO: 12

DVVMTQSPLSLPVTLGQPASISCRSSQSIVYSNGNTYLNWFQQRPGQSPRR
LIYRVSNRDSGVPDRFSGSGSGTDFTLKISRVEAEDVGVYYCFQGSHIPYT
FGQGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQ
GLSSPVTKSFNRGEC (AM-VL2-E40)

SEQ ID NO: 13

DVVMTQSPLSLPVTLGQPASISCRSSQSIVYSNGNTYLEWFQQRPGQSPRR
LIYRVSNRDSGVPDRFSGSGSGTDFTLKISRVEAEDVGVYYCFQGSHIPYT
FGQGTKLEIKRTVAAPSVFIFPPSDEQLKSGTASVVCLLNNFYPREAKVQW

-continued

KVDNALQSGNSQESVTEQDSKDSTYSLSSTLTLSKADYEKHKVYACEVTHQ
GLSSPVTKSFNRGEC

14. Anti-ADM antibody or anti-ADM antibody fragment binding to ADM or anti-ADM non-Ig scaffold binding to ADM for use in intervention and therapy of congestion in a patient according to any of items 1-13 wherein a sample of bodily fluid taken from said patients exhibits an elevated level of proADM and/or fragments thereof having at least 5 amino acids above a certain threshold.
15. Anti-ADM antibody or anti-ADM antibody fragment binding to ADM or anti-ADM non-Ig scaffold binding to ADM for use in intervention and therapy of congestion in a patient according to any of items 1-14 wherein said patient is resistant again diuretics or is a non-responder to diuretics therapy.
16. Pharmaceutical formulation for use in intervention and therapy of congestion in a patient comprising an antibody or fragment or scaffold according to any of items 1 to 15.
17. Pharmaceutical formulation for use in intervention and therapy of congestion in a patient comprising an antibody or fragment or scaffold according to any of items 1 to 16 wherein said patient has a disease or condition selected from the group comprising: congestive high blood pressure, swelling or water retention (edema), heart failure in particular acute heart failure, kidney or liver disease.
18. Pharmaceutical formulation for use in intervention and therapy of congestion in a patient according to item 16 or 17 wherein said pharmaceutical formulation is a solution, preferably a ready-to-use solution.
19. Pharmaceutical formulation for use in intervention and therapy of congestion in a patient according to item 18 wherein said pharmaceutical formulation is in a freeze-dried state.
20. Pharmaceutical formulation for use in intervention and therapy of congestion in a patient according to any of items 18 to 19, wherein said pharmaceutical formulation is administered intra-muscular.
21. Pharmaceutical formulation for use in intervention and therapy of congestion in a patient according to any of items 18 to 19, wherein said pharmaceutical formulation is administered intra-vascular.
22. Pharmaceutical formulation for use in intervention and therapy of congestion in a patient according to item 21, wherein said pharmaceutical formulation is administered via infusion.
23. Pharmaceutical formulation for use in intervention and therapy of congestion in a patient according to any of the items 18 to 22, wherein said pharmaceutical formulation is to be administered systemically.

EXAMPLES

It should be emphasized that the antibodies, antibody fragments and non-Ig scaffolds of the example portion in accordance with the invention are binding to ADM, and thus should be considered as anti-ADM antibodies/antibody fragments/non-Ig scaffolds.

Example 1

Generation of Antibodies and Determination of their Affinity Constants

Several human and murine antibodies were produced and their affinity constants were determined (see tables 1 and 2).

Peptides/Conjugates for Immunization:

Peptides for immunization were synthesized, see Table 1, (JPT Technologies, Berlin, Germany) with an additional N-terminal Cystein (if no Cystein is present within the selected ADM-sequence) residue for conjugation of the peptides to Bovine Serum Albumin (BSA). The peptides were covalently linked to BSA by using Sulfolink-coupling gel (Perbio-science, Bonn, Germany). The coupling procedure was performed according to the manual of Perbio.

The murine antibodies were generated according to the following method:

A Balb/c mouse was immunized with 100 μg Peptide-BSA-Conjugate at day 0 and 14 (emulsified in 100 μl complete Freund's adjuvant) and 50 g at day 21 and 28 (in 100 μl incomplete Freund's adjuvant). Three days before the fusion experiment was performed, the animal received 50 μg of the conjugate dissolved in 100 μl saline, given as one intraperitoneal and one intra-venous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting, the selected cultures were cloned and recloned using the limiting-dilution technique and the isotypes were determined (see also Lane, R. D. 1985. *J. Immunol. Meth.* 81: 223-228: Ziegler et al. 1996. Honm. *Metab. Res.* 28: 11-15).

Mouse Monoclonal Antibody Production:

Antibodies were produced via standard antibody production methods (Marx et al. 1997. *Monoclonal Antibody Production*, ATLA 25, 121) and purified via Protein A. The antibody purities were >95% based on SDS gel electrophoresis analysis.

Human Antibodies:

Human Antibodies were produced by means of phage display according to the following procedure:

The human naive antibody gene libraries HAL7/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see also Hust et al. 2011. *Journal of Biotechnology* 152, 159-170: Schüitte et al. 2009. *PLoS One* 4. e6625).

Positive clones have been selected based on positive ELISA signal for antigen and negative for streptavidin coated micro titer plates. For further characterizations the scFv open reading frame has been cloned into the expression plasmid pOPE107 (Hust et al. *J. Biotechn.* 2011), captured from the culture supernatant via immobilised metal ion affinity chromatography and purified by a size exclusion chromatography.

Affinity Constants:

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare). (Lorenz et al. 2011. *Antimicrob Agents Chemother.* 55(1): 165-173).

The monoclonal antibodies were raised against the below depicted ADM regions of human and murine ADM, respectively. The following table represents a selection of obtained antibodies used in further experiments. Selection was based on target region:

TABLE 1

| Sequence Number | Antigen/Immunogen | ADM Region | Designation | Affinity constants Kd (M) |
|---|---|---|---|---|
| SEQ ID: 14 | YRQSMNNFQGLRSFGCRFGTC | 1-21 | NT-H | $5.9 \times 10^{-9}$ |
| SEQ ID: 15 | CTVQKLAHQIYQ | 21-32 | MR-H | $2 \times 10^{-9}$ |
| SEQ ID: 16 | CAPRSKISPQGY-NH2 | C-42-52 | CT-H | $1.1 \times 10^{-9}$ |
| SEQ ID: 17 | YRQSMNQGSRSNGCRFGTC | 1-19 | NT-M | $3.9 \times 10^{-9}$ |
| SEQ ID: 18 | CTFQKLAHQIYQ | 19-31 | MR-M | $4.5 \times 10^{-10}$ |
| SEQ ID: 19 | CAPRNKISPQGY-NH2 | C-40-50 | CT-M | $9 \times 10^{-9}$ |

The following is a list of further obtained monoclonal antibodies:

TABLE 2

| Target | Source | Clone number | Affinity (M) | max inhibition bioassay (%) (see example 2) |
|---|---|---|---|---|
| NT-M | Mouse | ADM/63 | $5.8 \times 10^{-9}$ | 45 |
| | Mouse | ADM/364 | $2.2 \times 10^{-8}$ | 48 |
| | Mouse | ADM/365 | $3.0 \times 10^{-8}$ | |
| | Mouse | ADM/366 | $1.7 \times 10^{-8}$ | |
| | Mouse | ADM/367 | $1.3 \times 10^{-8}$ | |
| | Mouse | ADM/368 | $1.9 \times 10^{-8}$ | |
| | Mouse | ADM/369 | $2.0 \times 10^{-8}$ | |
| | Mouse | ADM/370 | $1.6 \times 10^{-8}$ | |
| | Mouse | ADM/371 | $2.0 \times 10^{-8}$ | |
| | Mouse | ADM/372 | $2.5 \times 10^{-8}$ | |
| | Mouse | ADM/373 | $1.8 \times 10^{-8}$ | |
| | Mouse | ADM/377 | $1.5 \times 10^{-8}$ | |
| | Mouse | ADM/378 | $2.2 \times 10^{-8}$ | |
| | Mouse | ADM/379 | $1.6 \times 10^{-8}$ | |
| | Mouse | ADM/380 | $1.8 \times 10^{-8}$ | |
| | Mouse | ADM/381 | $2.4 \times 10^{-8}$ | |
| | Mouse | ADM/382 | $1.6 \times 10^{-8}$ | |
| | Mouse | ADM/383 | $1.8 \times 10^{-8}$ | |
| | Mouse | ADM/384 | $1.7 \times 10^{-8}$ | |
| | Mouse | ADM/385 | $1.7 \times 10^{-8}$ | |
| | Mouse | ADM/403 | $1.2 \times 10^{-8}$ | |
| | Mouse | ADM/395 | $1.2 \times 10^{-8}$ | |
| | Mouse | ADM/396 | $3.0 \times 10^{-8}$ | |
| | Mouse | ADM/397 | $1.5 \times 10^{-8}$ | |
| MR-M | Mouse | ADM/38 | $4.5 \times 10^{-10}$ | 68 |
| MR-M | Mouse | ADM/39 | $5.9 \times 10^{-9}$ | 72 |
| CT-M | Mouse | ADM/65 | $9.0 \times 10^{-9}$ | 100 |
| CT-M | Mouse | ADM/66 | $1.6 \times 10^{-8}$ | 100 |
| NT-H | Mouse | ADM/33 | $5.9 \times 10^{-8}$ | 38 |
| NT-H | Mouse | ADM/34 | $1.6 \times 10^{-8}$ | 22 |
| MR-H | Mouse | ADM/41 | $1.2 \times 10^{-8}$ | 67 |
| MR-H | Mouse | ADM/42 | $<1 \times 10^{-8}$ | |
| MR-H | Mouse | ADM/43 | $2.0 \times 10^{-9}$ | 73 |
| MR-H | Mouse | ADM/44 | $<1 \times 10^{-8}$ | |
| CT-H | Mouse | ADM/15 | $<1 \times 10^{-8}$ | |
| CT-H | Mouse | ADM/16 | $1.1 \times 10^{-9}$ | 100 |
| CT-H | Mouse | ADM/17 | $3.7 \times 10^{-9}$ | 100 |
| CT-H | Mouse | ADM/18 | $<1 \times 10^{-8}$ | |
| hADM | Phage display | ADM/A7 | $<1 \times 10^{-8}$ | |
| | Phage display | ADM/B7 | $<1 \times 10^{-8}$ | |
| | Phage display | ADM/C7 | $<1 \times 10^{-8}$ | |
| | Phage display | ADM/G3 | $<1 \times 10^{-8}$ | |
| | Phage display | ADM/B6 | $<1 \times 10^{-8}$ | |
| | Phage display | ADM/B11 | $<1 \times 10^{-8}$ | |
| | Phage display | ADM/D8 | $<1 \times 10^{-8}$ | |
| | Phage display | ADM/D11 | $<1 \times 10^{-8}$ | |
| | Phage display | ADM/G12 | $<1 \times 10^{-8}$ | |

Generation of Antibody Fragments by Enzymatic Digestion:

The generation of Fab and F(ab)2 fragments was done by enzymatic digestion of the murine full length antibody NT-M. Antibody NT-M was digested using a) the pepsin-based $F(ab)_2$ Preparation Kit (Pierce 44988) and b) the papain-based Fab Preparation Kit (Pierce 44985). The fragmentation procedures were performed according to the instructions provided by the supplier. Digestion was carried out in case of F(ab)2-fragmentation for 8 h at 37° C. The Fab-fragmentation digestion was carried out for 16 h, respectively.

Procedure for Fab Generation and Purification:

The immobilized papain was equilibrated by washing the resin with 0.5 ml of Digestion Buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes.

0.5 ml of the prepared IgG sample where added to the spin column tube containing the equilibrated Immobilized Papain. Incubation time of the digestion reaction was done for 16 h on a tabletop rocker at 37° C. The column was centrifuged at 5000×g for 1 minute to separate digest from the Immobilized Papain. Afterwards the resin was washed with 0.5 ml PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 ml of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments. (References: Coulter and Harris 1983. *J. Immunol. Meth.* 59, 199-203.: Lindner et al. 2010. *Cancer Res.* 70, 277-87: Kaufmann et al. 2010. *PNAS.* 107, 18950-5.; Chen et al. 2010. *PNAS.* 107, 14727-32; Uysal et al. 2009 *J. Exp. Med.* 206, 449-62: Thomas et al. 2009. *J. Exp. Med.* 206, 1913-27: Kong et al. 2009 *J. Cell Biol.* 185, 1275-840).

Procedure for Generation and Purification of $F(Ab')_2$ Fragments:

The immobilized Pepsin was equilibrated by washing the resin with 0.5 ml of Digestion Buffer and centrifuging the column at 5000×g for 1 minute. The buffer was discarded afterwards. The desalting column was prepared by removing the storage solution and washing it with digestion buffer, centrifuging it each time afterwards at 1000×g for 2 minutes. 0.5 ml of the prepared IgG sample where added to the spin column tube containing the equilibrated Immobilized Pepsin. Incubation time of the digestion reaction was done for 16 h on a tabletop rocker at 37° C. The column was centrifuged at 5000×g for 1 minute to separate digest from the Immobilized Papain. Afterwards the resin was washed with 0.5 mL PBS and centrifuged at 5000×g for 1 minute. The wash fraction was added to the digested antibody that the total sample volume was 1.0 ml. The NAb Protein A Column was equilibrated with PBS and IgG Elution Buffer at room temperature. The column was centrifuged for 1 minute to remove storage solution (contains 0.02% sodium azide) and equilibrated by adding 2 mL of PBS, centrifuge again for 1 minute and the flow-through discarded. The sample was applied to the column and resuspended by inversion. Incubation was done at room temperature with end-over-end mixing for 10 minutes. The column was centrifuged for 1 minute, saving the flow-through with the Fab fragments. (References: Mariani et al. 1991. *Mol. Immunol.* 28, 69-77: Beak 1987. *Exp Comp Immunol* 11:287-96: Ellerson et al. 1972. *FEBS Letters* 24(3):318-22: Kerbel and Elliot 1983. *Meth Enzymol* 93:113-147: Kulkarni et al. 1985. *Cancer Immunol Immunotherapy* 19.211-4: Lannoyi 1986. *Meth Enzymol* 121:652-663: Parham et al. 1982. *J Immunol Meth* 53:133-73: Raychaudhuri et al. 1985. *Mol Immunol* 22(9):1009-19: Rousseaux et al. 1980. *Mol Immunol* 17.469-82: Rousseaux et al. 1983. *J Immunol Meth* 64:141-6: Wilson et al. 1991. *J Immunol Meth* 138:111-9).

NT-H-Antibody Fragment Humanization:

The antibody fragment was humanized by the CDR-grafting method (Jones et al. 1986. *Nature* 321, 522-525). The Following Steps where Done to Achieve the Humanized Sequence:

Total RNA extraction: Total RNA was extracted from NT-H hybridomas using the Qiagen kit.

First-round RT-PCR: QIAGEN® OneStep RT-PCR Kit (Cat No. 210210) was used. RT-PCR was performed with primer sets specific for the heavy and light chains. For each RNA sample, 12 individual heavy chain and 11 light chain RT-PCR reactions were set up using degenerate forward primer mixtures covering the leader sequences of variable regions. Reverse primers are located in the constant regions of heavy and light chains. No restriction sites were engineered into the primers.

Reaction Setup: 5×QIAGEN® OneStep RT-PCR Buffer 5.0 μl, dNTP Mix (containing 10 mM of each dNTP) 0.8 μl, Primer set 0.5 μl, QIAGEN® OneStep RT-PCR Enzyme Mix 0.8 μl, Template RNA 2.0 μl, RNase-free water to 20.0 μl, Total volume 20.0 μl PCR condition: Reverse transcription: 50° C., 30 min; Initial PCR activation: 95° C., 15 min Cycling: 20 cycles of 94° C., 25 sec; 54° C., 30 sec; 72° C., 30 sec; Final extension: 72° C., 10 min Second-round semi-nested PCR: The RT-PCR products from the first-round reactions were further amplified in the second-round PCR. 12 individual heavy chain and 11 light chain RT-PCR reactions were set up using semi-nested primer sets specific for antibody variable regions.

Reaction Setup: 2×PCR mix 10 μl; Primer set 2 μl; First-round PCR product 8 μl; Total volume 20 μl; Hybridoma Antibody Cloning Report PCR condition: Initial denaturing of 5 min at 95° C.; 25 cycles of 95° C. for 25 sec, 57° C. for 30 sec, 68° C. for 30 sec; Final extension is 10 min 68° C.

After PCR is finished, run PCR reaction samples onto agarose gel to visualize DNA fragments amplified. After sequencing more than 15 cloned DNA fragments amplified by nested RT-PCR, several mouse antibody heavy and light chains have been cloned and appear correct. Protein sequence alignment and CDR analysis identifies one heavy chain and one light chain. After alignment with homologous human framework sequences the resulting humanized sequence for the variable heavy chain is the following: see FIG. 5. As the amino acids on positions 26, 40 and 55 in the variable heavy chain and amino acid on position 40 in the variable light are critical to the binding properties, they may be reverted to the murine original. The resulting candidates are depicted below. (Padlan 1991. *Mol. Immunol.* 28, 489-498: Harris and Bajorath.1995. *Protein Sci.* 4, 306-310).

Annotation for the antibody fragment sequences (SEQ ID No.: 7-14): bold and underline are the CDR 1, 2, 3 in chronologically arranged; italic are constant regions; hinge regions are highlighted with bold letters and the histidine tag with bold and italic letters; framework point mutation have a grey letter-background.

(AM-VH-C)

SEQ ID No.: 6

QVQLQQSGAELMKPGASVKISCKATGYTFSRYWIEWVKQRPGHGLEWIGEILPGSG
STNYNEKFKGKATITADTSSNTAYMQLSSLTSEDSAVYYCTEGYEYDGFDYWGQGTTLT
VSSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKHHHHHH

(AM-VH1)

SEQ ID No.: 7

QVQLVQSGAEVKKPGSSVKVSCKASGYTFSRYWISWVRQAPGQGLEWMGRILPGS
GSTNYAQKFQGRVTITADESTSTAYMELSSLRSEDTAVYYCTEGYEYDGFDYWGQGTTV
TVSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKHHHHHH

(AM-VH2-E40)

SEQ ID No.: 8

QVQLVQSGAEVKKPGSSVKVSCKASGYTFSRYWIEWVRQAPGQGLEWMGRILPGS
GSTNYAQKFQGRVTITADESTSTAYMELSSLRSEDTAVYYCTEGYEYDGFDYWGQGTTV
TVSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKHHHHHH

(AM-VH3-T26-E55)

SEQ ID No.: 9

QVQLVQSGAEVKKPGSSVKVSCKATGYTFSRYWISWVRQAPGQGLEWMGEILPGS
GSTNYAQKFQGRVTITADESTSTAYMELSSLRSEDTAVYYCTEGYEYDGFDYWGQGTTV
TVSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKHHHHHH

(AM-VH4-T26-E40-E55)

SEQ ID No.: 10

QVQLVQSGAEVKKPGSSVKVSCKATGYTFSRYWIEWVRQAPGQGLEWMGEILPGS
GSTNYAQKFQGRVTITADESTSTAYMELSSLRSEDTAVYYCTEGYEYDGFDYWGQGTTV
TVSSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKHHHHHH

-continued (AM-VL-C)

SEQ ID No.: 11

DVLLSQTPLSLPVSLGDQATISCRSSQSIVYSNGNTYLEWYLQKPGQSPKLLIYRVSN

RFSGVPDRFSGSGSGTDFTLKISRVEAEDLGVYYCFQGSHIPYTFGGGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC (AM-VL1)

SEQ ID No.: 12

DVVMTQSPLSLPVTLGQPASISCRSSQSIVYSNGNTYLNWFQQRPGQSPRRLIYRVSN

RDSGVPDRFSGSGSGTDFTLKISRVEAEDVGVYYCFQGSHIPYTFGQGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC (AM-VL2-E40)

SEQ ID No.: 13

DVVMTQSPLSLPVTLGQPASISCRSSQSIVYSNGNTYLEWFQQRPGQSPRRLIYRVSN

RDSGVPDRFSGSGSGTDFTLKISRVEAEDVGVYYCFQGSHIPYTFGQGTKLEIKRTVA

APSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

Example 2

Effect of Selected Anti-ADM-Antibodies on Anti-ADM-Bioactivity

The effect of selected ADM-antibodies on ADM-bioactivity was tested in a human recombinant Adrenomedullin receptor cAMP functional assay (Adrenomedullin Bioassay).

Testing of Antibodies Targeting Human or Mouse Adrenomedullin in Human Recombinant Adrenomedullin Receptor cAMP Functional Assay (Adrenomedullin Bioassay)

Materials:

Cell line: CHO-K1

Receptor. Adrenomedullin (CRLR+RAMP3)

Receptor Accession Number Cell line: CRLR: U17473; RAMP3: AJ001016

CHO-K1 cells expressing human recombinant adrenomedullin receptor (FAST-027C) grown prior to the test in media without antibiotic were detached by gentle flushing with PBS-EDTA (5 mM EDTA), recovered by centrifugation and resuspended in assay buffer (KRH: 5 mM KCl, 1.25 mM $MgSO_4$, 124 mM NaCl, 25 mM HEPES, 13.3 mM Glucose, 1.25 mM $KH_2PO_4$, 1.45 mM $CaCl_2$), 0.5 g/l BSA).

Dose response curves were performed in parallel with the reference agonists (hADM or mADM).

Antagonist Test (96Well):

For antagonist testing, 6 µl of the reference agonist (human (5.63 nM) or mouse (0.67 nM) adrenomedullin) was mixed with 6 µl of the test samples at different antagonist dilutions; or with 6 µl buffer. After incubation for 60 min at room temperature, 12 µl of cells (2,500 cells/well) were added. The plates were incubated for 30 min at room temperature. After addition of the lysis buffer, percentage of DeltaF will be estimated, according to the manufacturer specification, with the HTRF kit from Cis-Bio International (cat n° 62AM2 PEB) hADM 22-52 was used as reference antagonist.

Antibodies Testing cAMP-HTRF Assay

The anti-h-ADM antibodies (NT-H, MR-H, CT-H) were tested for antagonist activity in human recombinant adrenomedullin receptor (FAST-027C) cAMP functional assay in the presence of 5.63 nM Human ADM 1-52, at the following final antibody concentrations: 100 µg/ml, 20 µg/ml, 4 µg/ml, 0.8 µg/ml, 0.16 µg/ml.

The anti-m-ADM antibodies (NT-M, MR-M, CT-M) were tested for antagonist activity in human recombinant adrenomedullin receptor (FAST-027C) cAMP functional assay in the presence of 0.67 nM Mouse ADM 1-50, at the following final antibody concentrations: 100 µg/ml, 20 µg/ml, 4 µg/ml, 0.8 µg/ml, 0.16 µg/ml. Data were plotted relative inhibition vs. antagonist concentration (see FIGS. 2*a* to 2*l*). The maximal inhibition by the individual antibody is given in table 3.

TABLE 3

| Antibody | Maximal inhibition of ADM bioactivity (ADM-Bioassay) (%) |
|---|---|
| NT-H | 38 |
| MR-H | 73 |
| CT-H | 100 |
| NT-M FAB | 26 |
| NT-M FAB2 | 28 |
| NT-M | 45 |
| MR-M | 66 |
| CT-M | 100 |
| Non specific mouse IgG | 0 |

Example 3

Data for Stabilization of hADM by the Anti-ADM Antibody

The stabilizing effect of human ADM by human ADM antibodies was tested using a hADM immunoassay.

Immunoassay for the Quantification of Human Adrenomedullin

The technology used was a sandwich coated tube luminescence immunoassay, based on Acridinium ester labelling.

Labelled Compound (Tracer):

100 µg (100 µl) CT-H (1 mg/ml in PBS, pH 7.4, AdrenoMed AG Germany) was mixed with 10 µl Acridinium NHS-ester (1 mg/ml in acetonitrile, InVent GmbH, Germany) (EP 0353971) and incubated for 20 min at room temperature. Labelled CT-H was purified by Gel-filtration HPLC on Bio-Sil® SEC 400-5 (Bio-Rad Laboratories, Inc., USA) The purified CT-H was diluted in (300 mmol/L potassium phosphate, 100 mmol/L NaCl, 10 mmol/L Na-EDTA, 5 g/L Bovine Serum Albumin, pH 7.0). The final concentration was approx. 800.000 relative light units (RLU) of labelled compound (approx. 20 ng labeled antibody) per 200 μL. Acridiniumester chemiluminescence was measured by using an AutoLumat LB 953 (Berthold Technologies GmbH & Co. KG).

Solid Phase:

Polystyrene tubes (Greiner Bio-One International AG, Austria) were coated (18 h at room temperature) with MR-H (AdrenoMed AG, Germany) (1.5 μg MR-H/0.3 mL 100 mmol/L NaCl, 50 mmol/L TRIS/HCl, pH 7.8). After blocking with 5% bovine serum albumine, the tubes were washed with PBS, pH 7.4 and vacuum dried.

Calibration:

The assay was calibrated, using dilutions of hADM (BACHEM AG, Switzerland) in 250 mmol/L NaCl, 2 g/L Triton X-100, 50 g/L Bovine Serum Albumin, 20 tabs/L Protease Inhibitor Cocktail (Roche Diagnostics AG, Switzerland).

hADM Immunoassay:

50 μl of sample (or calibrator) was pipetted into coated tubes, after adding labeled CT-H (200 μl), the tubes were incubated for 4 h at 4° C. Unbound tracer was removed by washing 5 times (each 1 ml) with washing solution (20 mM PBS, pH 7.4, 0.1% Triton X-100).

Figure 3:
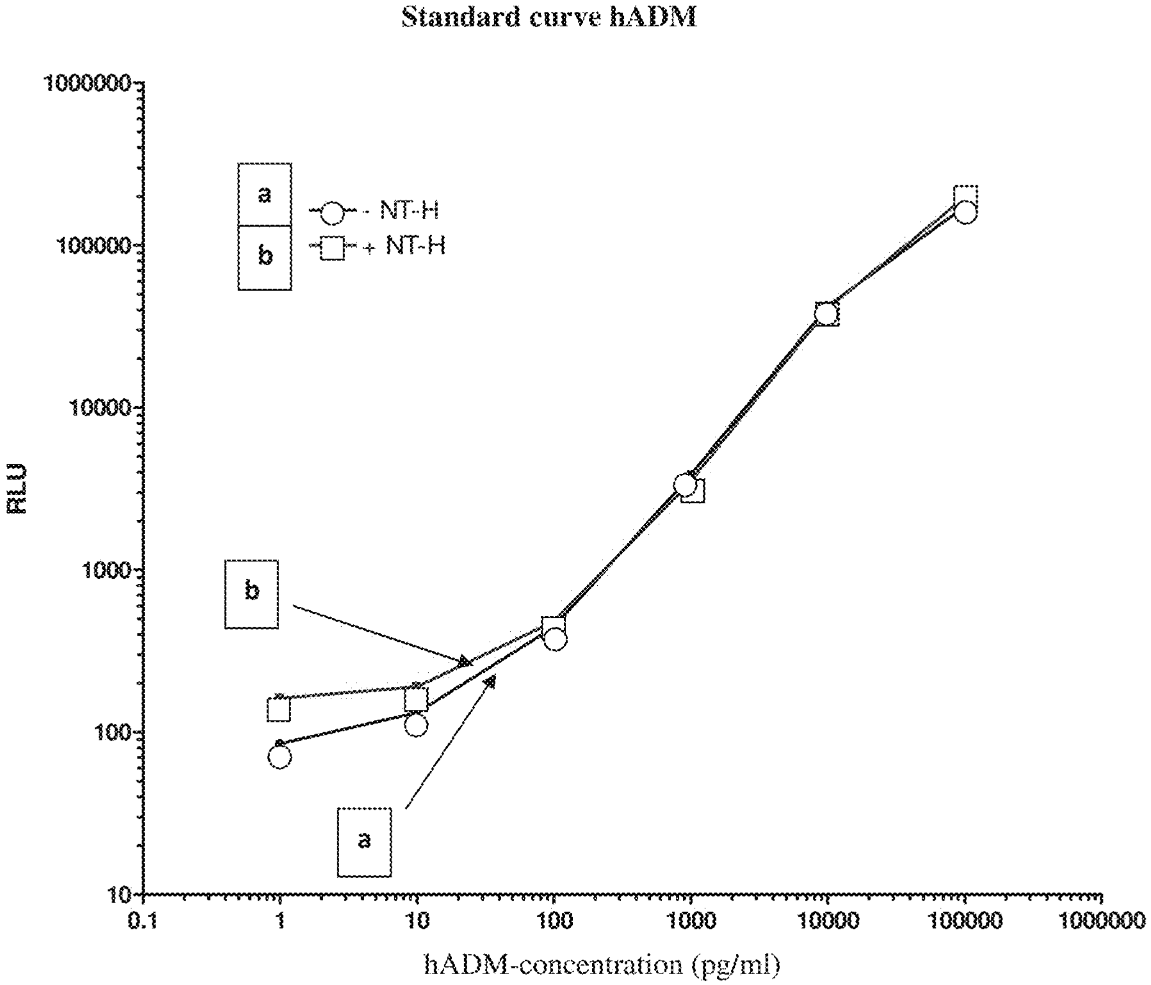

Tube-Bound Chemiluminescence was Measured by Using the LB 953:

FIG. 3 shows a typical hADM dose/signal curve. And an hADM dose signal curve in the presence of 100 μg/mL antibody NT-H. NT-H did not affect the described hADM immunoassay.

Stability of Human Adrenomedullin:

Human ADM was diluted in human Citrate plasma (final concentration 10 nM) and incubated at 24° C. At selected time points, the degradation of hADM was stopped by freezing at −20° C. The incubation was performed in absence and presence of NT-H (100 μg/ml). The remaining hADM was quantified by using the hADM immunoassay described above.

Figure 4:
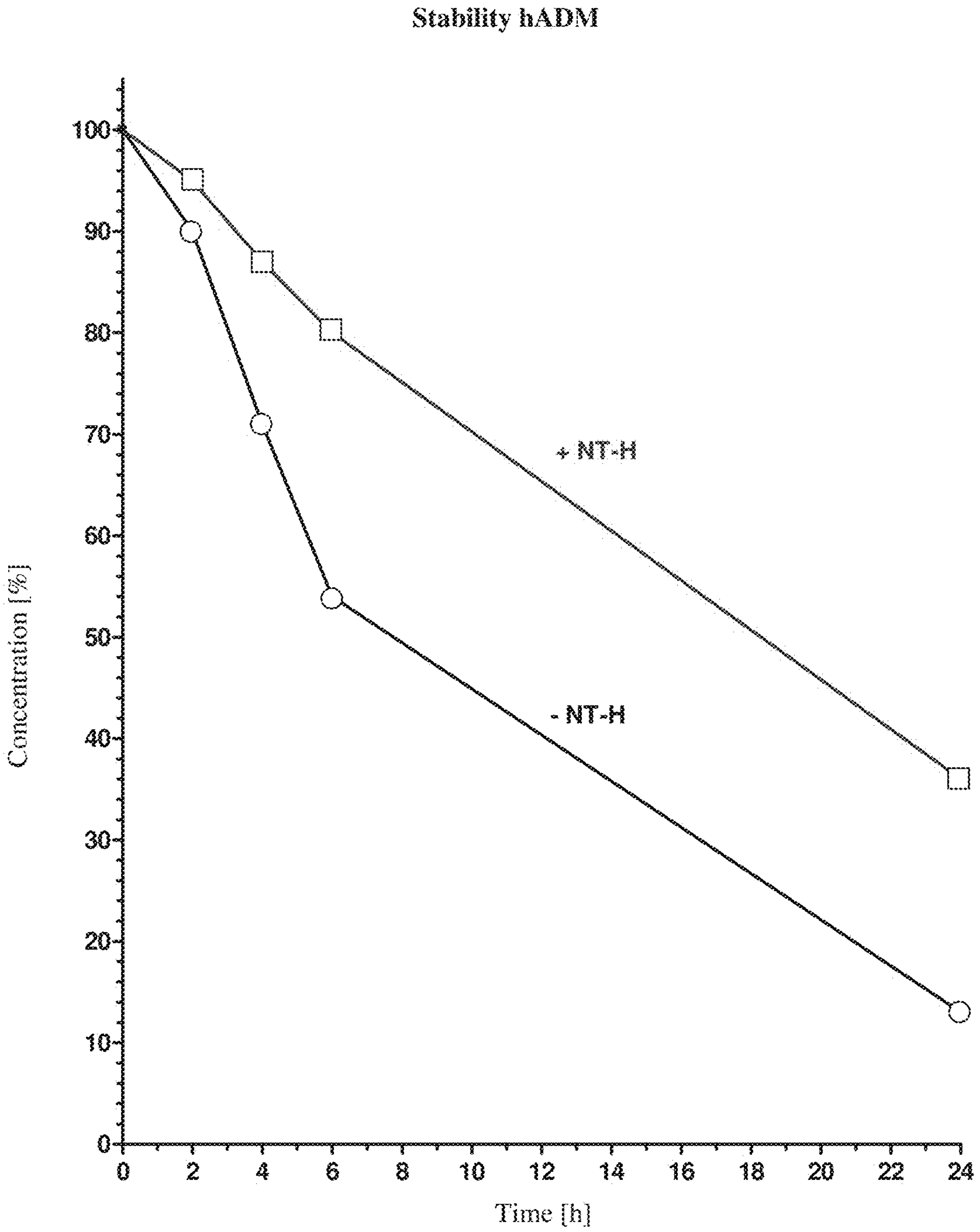

FIG. 4 shows the stability of hADM in human plasma (citrate) in absence and in the presence of NT-H antibody. The half-life of hADM alone was 7.8 h and in the presence of NT-H, the half-life was 18.3 h. (2.3 times higher stability).

Example 4

In Vivo Side Effect Determination of Antibody NT-M 12-15 week old male C57BU/6 mice (Charles River Laboratories, Germany) were used for the study. 6 mice were treated with (10 μl/g bodyweight) dose of NT-M, 0.2 mg/ml. As control, 6 mice were treated with (10 μl/g body weight) PBS. Survival and physical condition was monitored for 14 days. The mortality was 0 in both groups, there were no differences in physical condition between NT-M and control group.

Example 5

Dose Dependency of Efficacy of NT-H

The dose dependency of efficacy of NT-H in a mouse CLP model on the basis of kidney barrier dysfunction determined by immunhistochemical staining of the kidney was examined. 12-15 week old male C57Bl/6 mice (Charles River Laboratories, Germany; n=6/group, 4 groups) were used for the study. Peritonitis was surgically induced under light isofluran anesthesia (and Rimadyl 0.5 mg/kg s.c. with surgery). Incisions were made into the left upper quadrant of the peritoneal cavity (normal location of the cecum). The cecum was exposed and a tight ligature was placed around the cecum with sutures distal to the insertion of the small bowel. One puncture wound was made with a 24-gauge needle into the cecum and small amounts of cecal contents were expressed through the wound. The cecum was replaced into the peritoneal cavity and the laparotomy site was closed. Finally, animals were returned to their cages with free access to food and water. 500 μl saline was given s.c. as fluid replacement. 18 hours after CLP and application of test article the animals are sacrificed and kidneys removed.

Mice were treated with vehicle and compound at different concentrations. Vehicle and compounds were supplied by the sponsor as A, B, C and D labelled tubes as "ready-to-use" solutions. A single intravenous injection was performed 5 minutes prior to CLP in the dose 0.1/2/20 mg/kg body weight at a volume 5 μl/g body weight by tail vein injection. Vehicle was 20 mM His/HCl, pH 6.0.

Terminal bleeding was performed from the survivors after 18 hours. 500 μl blood drawing at 6 h after CLP were obtained from 3 additional individuals per group by terminal bleeding. EDTA-plasma samples were deep frozen latest 1 h after sampling.

Kidney Processing for Immunohistochemistry:

Mice were sacrificed by exsanguination, thus the kidney was not full of blood, and kidney was immediately removed thereafter. After dissection the kidney was cut in a sagittal section yielding two complete halves. The two kidney halves were placed in a minimum of 10× volume of 10% Formalin (4% formaldehyde neutral buffered: Fischer 639 3113). The two halves, severally (not attached), were placed in a 5 ml cup filled with 10% Formalin and (samples could be mailed to us during fixation) fixed for 6 days at room temperature (Dehydration and paraffin embedding overnight: dH20 wash 2 hrs, 40% ethanol 1 hr, 70% ethanol 1 hr 2×, 80% ethanol 1 hr, 90% ethanol 1 hr, 100% ethanol 1 hr 2×, Xylene 40° C. 1.5 hrs, Xylene 45° C. 1.5 hrs, Paraffin 60° C. 1 hr 3×, embedded in cassette). The left kidney was immediately dissected upon receipt, formalin-fixed for 6 days and embedded in paraffin. 5 μm sections were deparaffinised, exposed to HIER, 10% goat or donkey serum, 1° antibodies (VEGF, Alb, Ang1) 2° ab anti-rabbit or anti-goat IgG AP followed by Dako REAL chromogen and counterstained with hematoxlin. Slides were analyzed using the Axio Vision (rel. 4.8) software (Zeiss, Jena Germany) and are represented as mean densitometric sum red.

Figure 6:
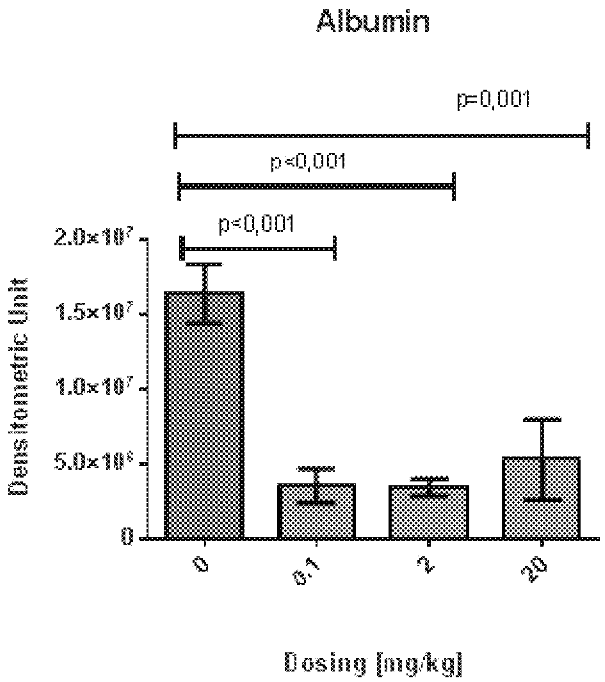

The densitometric evaluation of the stained kidneys regarding albumin showed a significant lower extravascular albumin accumulation of all three doses tested with a slightly lower effect on the 20 mg/kg dose (FIG. 6).

Figure 7:
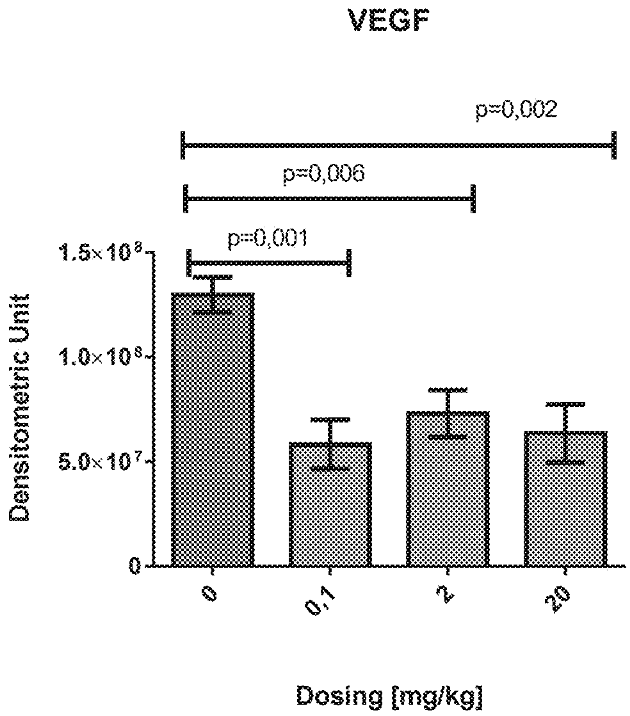

VEGF is known to increase endothelial vascular permeability and therefore acts as a supporting biomarker for the status of the kidney barrier function. As depicted in FIG. 7 there is a significant lower VEGF expression in all tested doses without any dose dependency.

Figure 8:
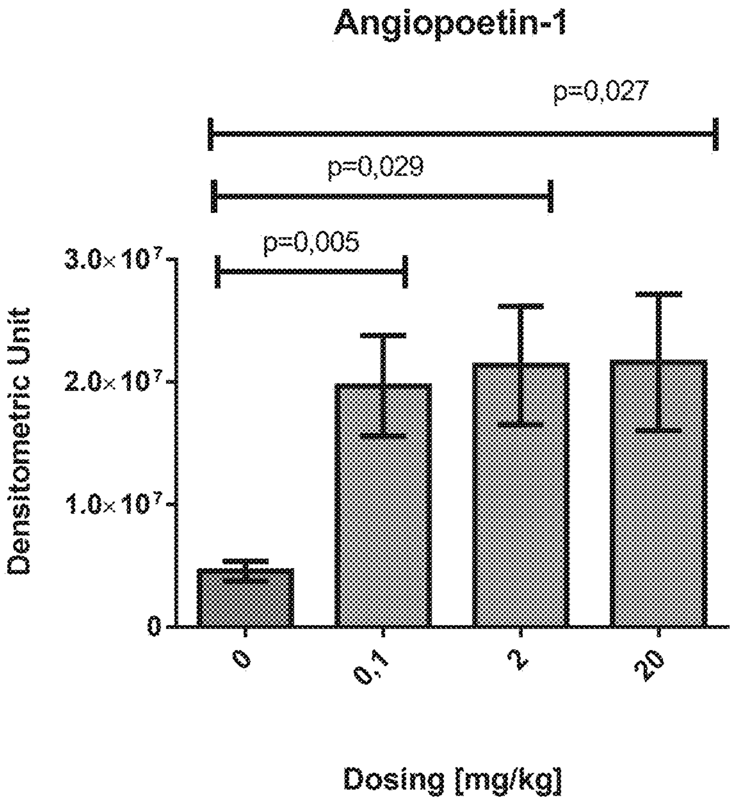

Angiopoietin1 is known to protect against this VEGF-induced plasma leakage and therefore should be in reciprocal relation to the VEGF expression level. This is shown in FIG. 8 with significance for all tested doses.

In this study the efficacy of three different doses of NT-H given i.v. 5 min prior to surgery was evaluated in the model of CLP induced peritonitis in mice. NT-H significantly improves vascular integrity of the kidney of septic mice compared to the placebo group over all doses tested. NT-H exploits a beneficial effect over a wide range of dosing with a slight trend of less effect at 20 mg/kg.

Moreover, the results of this study indicate the application of the NT-H antibody has a positive effect by decreasing the endothelial vascular permeability and therefore preventing or protecting from vascular fluid extravasation and finally from congestion and/or edema.

Example 6

PROTECT Study

Study Population and Measurements

The details of this study have been published (Massie et al. 2010. *N Engl J Med.* 363:1419-1428.: Weatherleyfunctioned al. 2010. *J Card Fail.* 16:25-35.: Voors et al. 2011. *J Am Coll Cardiol.* 57:1899-1907). In brief, 2,033 acute heart failure patients with renal function impairment (estimated creatinine clearance between 20 to 80 mL/min with Cockcroft-Gault formula) were included and randomized to rolofylline or placebo. The protocol of the PROTECT study was approved by the ethics committee at each participating center, and written informed consent was obtained from all participants.

Bio-ADM was measured from plasma collected during baseline evaluation in 1572 hospitalized AHF patients included in the PROTECT trial (all available baseline samples). PROTECT (stands for "Placebo-controlled Randomized Study of the Selective A1 Adenosine Receptor Antagonist Rolofylline for Patients Hospitalized with Acute Decompensated Heart Failure and Volume Overload to Assess Treatment Effect on Congestion and Renal Function") was a multicenter, randomized, double-blind trial that compared rolofylline against placebo in 2033 patients hospitalized for AHF.

Study Outcomes

As highlighted previously, clinical surrogates have less than optimal predictive value for the detection of congestion. In this analysis, we combined three of the strongest clinical surrogates of congestion (i.e. JVP, peripheral edema and orthopnea) to enhance accuracy and developed a composite clinical congestion score (CCS) using the scheme presented below:

| Parameter | 0 | 1 | 2 | 3 |
|---|---|---|---|---|
| Peripheral edema | 0 | Ankle | Below knee | Above knee |
| Orthopnea | 0 pillow | 1 pillow | 2 pillows | 3 pillows |
| JVP | <6 cm | 6-10 cm | >10 cm | — |

The score on each of these three parameters were then added to obtain a composite congestion score which ranged from 0 to 8. A similar scheme was previously utilized by Ambrosy et al. (Ambrosy et al. 2013. *European Heart Journal* 34 (11): 835-843).

The following algorithm was then utilized to grade severity of congestion:

CCS=0, No clinical congestion

CCS 1-3, Mild clinical congestion

CCS 4-5, Moderate clinical congestion

CCS≥6, Severe clinical congestion

Diuretic response was defined as weight loss by day 4 per 40 mg of diuretic dose.

Hemoconcentration was coded as 0 (if there is a decline or no change in hemoglobin levels by day 4 compared to baseline) or 1 (if there is an increase in hemoglobin levels by day 4 compared to baseline).

Significant residual congestion was defined as a CCS≥2 based on JVP, orthopnea and edema assessments by day 7.

Statistical Analysis

Baseline clinical characteristics and biomarkers including bio-ADM were summarized by severity of clinical congestion at baseline (scheme presented above). Baseline factors independently associated with severity of clinical congestion at baseline were determined using a multivariable logistic regression model (the CCS variable was recoded as a binary outcome with two levels; 0=mild/moderate (CCS<6) and 1=severe (CCS≥6)).

Association between baseline bio-ADM levels and diuretic response (a continuous variable) was evaluated using linear regression analysis. For the hemoconcentration and significant residual congestion outcomes, binary logistic regression analysis was performed. Multivariable models were utilized to evaluate adjusted associations between bio-ADM levels and these outcomes.

Results

In Table 4 it is demonstrated that bio-ADM concentrations increase with the severity of congestion.

TABLE 4

Baseline clinical variables and biomarkers by severity of clinical congestion at baseline

| | Mild clinical congestion N = 212 | Moderate clinical congestion N = 528 | Severe clinical congestion N = 667 | P-trend |
|---|---|---|---|---|
| Male sex, % (N) | 65.6 (139) | 68.4 (361) | 65.4 (436) | 0.656 |
| Age (yrs) | 71.5 ± 11.7 | 71.1 ± 11.3 | 70.8 ± 10.7 | 0.427 |
| BMI (Kg/m2) | 26.5 ± 4.4 | 27.8 ± 5.3 | 29.9 ± 6.4 | <0.001 |
| LVEF (%) | 32.1 ± 13.4 | 33.2 ± 13.4 | 32.2 ± 13.4 | 0.808 |
| SBP (mmHg) | 124.2 ± 17.9 | 125.2 ± 17.4 | 124.3 ± 17.3 | 0.773 |
| DBP (mmHg) | 72.9 ± 12.2 | 73.3 ± 11.4 | 74.1 ± 11.6 | 0.118 |
| Heart Rate (bpm) | 77.6 ± 13.6 | 79.1 ± 15.4 | 81 ± 15.9 | 0.002 |
| Respiratory rate (per min) | 20 [18-22] | 20 [18-24] | 21 [18-24] | 0.001 |
| Orthopnea, % (N) | | | | |
| None | 17.9 (38) | 4 (21) | 0 (0) | ref. |
| One pillow (10 cm) | 36.8 (78) | 14.8 (78) | 2.5 (17) | <0.001 |
| Two pillows (20 cm) | 33.0 (70) | 56.6 (299) | 31.8 (212) | <0.001 |
| >30 degrees | 12.3 (26) | 24.6 (130) | 65.7 (438) | <0.001 |

TABLE 4-continued

Baseline clinical variables and biomarkers by severity of clinical congestion at baseline

| | Mild clinical congestion N = 212 | Moderate clinical congestion N = 528 | Severe clinical congestion N = 667 | P-trend |
|---|---|---|---|---|
| Pulmonary rales, % (N) | | | | |
| <1/3 | 25.5 (54) | 33.5 (177) | 28.9 (193) | ref. |
| 1/3-2/3 | 57.1 (121) | 51.5 (272) | 48.9 (326) | 0.333 |
| >2/3 | 17.5 (37) | 15 (79) | 22.2 (148) | 0.101 |
| Edema, % (N) | | | | |
| 0 | 56.6 (120) | 15.3 (81) | 0 (0) | ref. |
| 1+ | 29.2 (62) | 33.1 (175) | 5.7 (38) | <0.001 |
| 2+ | 13.2 (28) | 43.2 (228) | 47.2 (315) | <0.001 |
| 3+ | 0.9 (2) | 8.3 (44) | 47.1 (314) | <0.001 |
| JVP, % (N) | | | | |
| <6 cm | 42.5 (90) | 12.3 (65) | 2.4 (16) | ref. |
| 6-10 cm | 52.4 (111) | 62.3 (329) | 34.9 (233) | <0.001 |
| >10 cm | 5.2 (11) | 25.4 (134) | 62.7 (418) | <0.001 |
| NYHA, % (N) | | | | |
| I | 0.9 (2) | 1.5 (8) | 0.7 (5) | 0.784 |
| II | 24.1 (51) | 15 (79) | 14.4 (96) | 0.779 |
| III | 50.5 (107) | 50.4 (266) | 47.4 (316) | 0.668 |
| IV | 14.6 (31) | 28.6 (151) | 34.6 (231) | 0.494 |
| Medical history | | | | |
| COPD, % (N) | 15.1 (32) | 20.1 (106) | 22 (146) | 0.039 |
| Stroke, % (N) | 8 (17) | 8.3 (44) | 10.9 (73) | 0.111 |
| Peripheral vascular disease, % (N) | 12.3 (26) | 11.6 (61) | 9.3 (62) | 0.145 |
| Hypertension, % (N) | 78.8 (167) | 77.7 (410) | 82.6 (551) | 0.075 |
| Diabetes mellitus, % (N) | 38.7 (82) | 44.1 (233) | 48.1 (321) | 0.013 |
| Hypercholesterolemia, % (N) | 58 (123) | 50 (264) | 51.1 (340) | 0.189 |
| Myocardial infarction, % (N) | 52.8 (112) | 50.1 (264) | 49.4 (328) | 0.424 |
| Angina, % (N) | 20.8 (44) | 20.7 (109) | 24 (160) | 0.187 |
| Ischaemic heart disease, % (N) | 68.9 (146) | 70.4 (371) | 71.4 (475) | 0.468 |
| Atrial fibrillation, % (N) | 44.3 (94) | 53.0 (279) | 59.8 (396) | <0.001 |
| Past HF hospitalization, % (N) | 41.5 (88) | 47.2 (249) | 53.4 (356) | 0.001 |
| PCI, % (N) | 34.0 (71) | 26.5 (139) | 23.3 (154) | 0.003 |
| CABG, % (N) | 26.3 (55) | 20.6 (108) | 22.5 (149) | 0.514 |
| Pacemaker, % (N) | 9.9 (21) | 11 (58) | 11.4 (76) | 0.556 |
| Medication during hospital admission | | | | |
| ACEI/ARB, % (N) | 78.3 (166) | 75.7 (399) | 75.6 (504) | 0.492 |
| Beta-blocker, % (N) | 82.1 (174) | 75.1 (396) | 75.1 (501) | 0.089 |
| MRA, % (N) | 41.5 (88) | 44.8 (236) | 47.5 (317) | 0.110 |
| Digoxin, % (N) | 20.3 (43) | 30.6 (161) | 31.3 (209) | 0.009 |
| Biomarkers | | | | |
| Albumin (g/dL) | 4.0 [3.7-4.3] | 3.9 [3.6-4.2] | 3.8 [3.5-4.1] | <0.001 |
| ALT (U/L) | 20 [14-32] | 21 [15-32] | 21 [15-30] | 0.299 |
| AST (U/L) | 23 [17-31] | 24 [19-33] | 25 [20-33] | 0.210 |
| Bicarbonate (mEq/L) | 23.6 ± 3.4 | 24.2 ± 3.6 | 24 ± 3.9 | 0.485 |
| BUN (mg/dL) | 29 [22-42] | 28 [21-40] | 31 [22-42] | 0.057 |
| Chloride (mEq/L) | 102 [99-105] | 101 [98-104] | 101 [98-104] | 0.085 |
| Creatinine (mg/dL) | 1.4 [1.1-1.8] | 1.4 [1.1-1.8] | 1.4 [1.1-1.8] | 0.59 |
| Total cholesterol (mg/dL) | 154.5 [122-183.5] | 146.5 [123-173.8] | 134 [110-164] | <0.001 |
| Glucose (mg/dL) | 126 [104.5-155] | 126 [101-168] | 128 [103-162] | 0.663 |
| Hemogblobin (g/dL) | 12.6 ± 1.8 | 12.5 ± 1.8 | 12.5 ± 1.9 | 0.716 |
| Platelet count (*10^9/1) | 221 [180-278] | 218 [170-268] | 211 [168-260] | 0.020 |
| Pottasium (mmol/L | 4.3 ± 0.6 | 4.3 ± 0.6 | 4.3 ± 0.6 | 0.723 |
| RBC count (*10^9/1) | 4.2 ± 0.6 | 4.2 ± 0.6 | 4.2 ± 0.6 | 0.200 |
| Sodium (mmol/L) | 140 [137-142] | 140 [138-142] | 140 [137-142] | 0.139 |

TABLE 4-continued

Baseline clinical variables and biomarkers by severity of clinical congestion at baseline

| | Mild clinical congestion N = 212 | Moderate clinical congestion N = 528 | Severe clinical congestion N = 667 | P-trend |
|---|---|---|---|---|
| Triglycerides (mmol/L) | 96 [66-132.5] | 89 [65-130] | 83 [64-112] | 0.003 |
| Uric acid (mg/dL) | 8.5 ± 2.5 | 8.8 ± 2.6 | 9.1 ± 2.5 | 0.003 |
| WBC (*10^9/1 | 7.9 [6.5-10] | 7.3 [6.2-9.1] | 7.3 [5.9-9] | 0.003 |
| Hematocrite (%) | 39.5 ± 5.4 | 39.4 ± 5.6 | 40.1 ± 5.9 | 0.09 |
| BNP (pg/ml) | 406.8 [255.8-648.2] | 437.4 [247.9-797.1] | 487.9 [274.8-874] | 0.002 |
| cTnI (pg/mL) | 12.0 [5.8-38.2] | 9.8 [5.2-20.1] | 10.8 [5.8-22.7] | 0.046 |
| bio-ADM (pg/mL) | 30.0 [20.2-46.1] | 37.4 [22.5-66.8] | 55.4 [31.4-102.6] | <0.001 |

Furthermore, it was demonstrated by multivariable logistic regression that bio-ADM is an independent predictor of the severity of congestion and the strongest among all other available variables (table 5).

TABLE 5

Baseline factors independently associated with severity of baseline clinical congestion in a multivariable logistic regression model (severe versus mild/moderate)

| Variable | Odds ratio [95% CI] | P-value |
|---|---|---|
| Past HF hospitalization | 1.40 [1.11-1.75] | 0.004 |
| BMI | 1.06 [1.04-1.08] | <0.001 |
| Serum albumin | 0.56 [0.43-0.74] | <0.001 |
| bio-ADM, log | 1.58 [1.38-1.82] | <0.001 |

The area under the curve (AUC) of the whole model was 0.69, individual AUCs: bio-ADM=0.66, BMI=0.61, semm albumin=0.58, past HF hospitalization=0.54.

There are very few baseline clinical variables or biomarkers associated with severity of clinical congestion at baseline and bio-ADM appears to be, by far, the strongest.

Furthermore, it was analyzed whether bio-ADM would predict decongestion. In table 6 it is demonstrated that bio-ADM is an independent predictor of significant residual congestion by day 7.

TABLE 6

Association between baseline bio-ADM levels and markers of decongestion

| | Unadjusted | | Adjusted | |
|---|---|---|---|---|
| Marker of decongestion | Estimate [95% CI] | P-value | Estimate [95% CI] | P-value |
| Significant residual congestion by day 7* | 1.98 [1.70-2.32] | <0.001 | 1.30 [1.10-1.60]** | 0.009 |
| Diuretic response by day 4 | 0.02 [−0.02-0.06] | 0.350 | — | — |
| Hemoconcentration by day 4 | 0.82 [0.71-0.94] | 0.004 | 0.90 [0.78-1.04]# | 0.160 |

*defined as composite congestion score >2 by day 7

**adjusted for baseline variables including orthopnea, JVP, peripheral edema, history of PCI, pacemaker, ACEI/ARB use, BMI, DBP, BUN, hematocrit and BNP

#adjusted for baseline clinical congestion score (NB: there is ~30% missingness in hemoconcentration data)

Baseline levels of bio-ADM independently predict significant residual congestion by day 7.

As to be expected for a marker of congestion, bio-ADM concentrations were higher the more diuretics were used for therapy (tables 7 and 8).

TABLE 7

Total IV diuretic dose through day 7 or discharge (if earlier) in tertiles of baseline bio-ADM levels; PROTECT

| | Tertile 1 | Tertile 2 | Tertile 3 | P-trend |
|---|---|---|---|---|
| Total IV diuretic dose through day 7 or discharge (if earlier), mg | 200.0 [92.6-352.8] | 280.0 [135.5-494.4] | 400.0 [200-882] | <0.001 |

| | Unadjusted | | Adjusted* | |
|---|---|---|---|---|
| | β (se) | p-value | β (se) | p-value |
| bio-ADM | 3.4 (0.3) | <0.001 | 2.2 (0.3) | <0.001 |

Table 8: Unadjusted and adjusted association between baseline bio-ADM levels and total IV diuretic dose through day 7 or discharge if earlier, linear regression analysis; PROTECT

* adjusted for age, systolic blood pressure, creatinine, blood urea nitrogen (BUN), albumin, sodium, previous HF hospitalization, baseline composite congestion score (CCS) and BNP; it must be noted that association was most robust for bio-ADM, baseline CCS and renal function in this model In the same sample set also MR-proADM was determined. Baseline characteristics by tertiles of MR-proADM are shown in table 9: Similar to bio-ADM, increasing levels of MR-proADM were associated with increasing extent of edema.

TABLE 9

| Baseline characteristics by tertiles of MR-proADM | | | | |
|---|---|---|---|---|
| Variable | Tertile 1 N = 516 | Tertile 2 N = 515 | Tertile 3 N = 516 | P-trend |
| MR-proADM (nmol/l) | 0.24 [0.14-0.29] | 0.55 [0.47-0.67] | 1.25 [0.94-1.88] | |
| Sex | 65.9 (340) | 64.3 (331) | 69.4 (358) | 0.235 |
| Age (yrs) | 70.1 ± 11.1 | 71.3 ± 10.9 | 71.3 ± 11.4 | 0.073 |
| BMI (Kg/m2) | 28 ± 5.5 | 28.9 ± 5.9 | 29.5 ± 6.5 | <0.001 |
| LVEF (%) | 32.9 ± 13.4 | 33.5 ± 12.3 | 31.3 ± 13.8 | 0.178 |
| SBP (mmHg) | 126.3 ± 17.5 | 125.9 ± 17.1 | 122.2 ± 17.4 | <0.001 |
| DBP (mmHg) | 74.1 ± 12.1 | 74.3 ± 11.6 | 72.6 ± 11.7 | 0.033 |
| Heart Rate (bpm) | 78.7 ± 14.4 | 79.8 ± 15.4 | 81.2 ± 16.5 | 0.008 |
| Respiratory rate (per min) | 20 [18-24] | 20 [18-24] | 22 [18.8-24] | 0.698 |
| Orthopnea | | | | |
| None | 3.5 (18) | 4.3 (22) | 3.3 (17) | ref. |
| One pillow | 12.8 (66) | 10.5 (54) | 13.2 (68) | 0.819 |
| Two pillows | 43.4 (224) | 43.3 (223) | 34.5 (178) | 0.619 |
| >30 degrees | 39.1 (202) | 41.2 (212) | 48.1 (248) | 0.439 |
| Rales | | | | |
| None | 8.3 (43) | 7.6 (39) | 11.2 (58) | ref. |
| <1/3 | 24.6 (127) | 29.1 (150) | 32.6 (168) | 0.849 |
| 1/3-2/3 | 58.3 (301) | 53 (273) | 45.7 (236) | 0.012 |
| >2/3 | 8.5 (44) | 10.3 (53) | 10.3 (53) | 0.622 |
| Edema | | | | |
| 0 | 16.3 (84) | 14.8 (76) | 12.2 (63) | ref. |
| 1+ | 24.8 (128) | 17.5 (90) | 15.3 (79) | 0.324 |
| 2+ | 39.7 (205) | 40 (206) | 40.5 (209) | 0.112 |
| 3+ | 19.2 (99) | 27.8 (143) | 31.8 (164) | <0.001 |
| JVP | | | | |
| <6 cm | 11 (57) | 9.3 (48) | 12.6 (65) | ref. |
| 6-10 cm | 45.3 (234) | 42.3 (218) | 40.3 (208) | 0.22 |
| >10 cm | 34.7 (179) | 37.7 (194) | 37.4 (193) | 0.755 |
| NYHA | | | | |
| I | 1.7 (9) | 0.8 (4) | 0.6 (3) | 0.024 |
| II | 17.4 (90) | 17.5 (90) | 13.8 (71) | 0.062 |
| III | 50.6 (261) | 49.3 (254) | 44.8 (231) | 0.07 |
| IV | 25.6 (132) | 29.1 (150) | 33.7 (174) | 0.114 |
| COPD | 18.6 (96) | 19.2 (99) | 21.9 (113) | 0.185 |
| Stroke | 8.7 (45) | 8 (41) | 11.2 (58) | 0.164 |
| Peripheral vascular disease | 10.1 (52) | 11.9 (61) | 11.9 (61) | 0.37 |
| Hypertension | 79.1 (408) | 83.3 (429) | 78.7 (406) | 0.876 |
| Diabetes mellitus | 44.6 (230) | 46 (237) | 47.5 (245) | 0.349 |
| Hypercholestrolemia | 53.8 (277) | 52.6 (271) | 46.9 (242) | 0.027 |
| Myocardial infarction | 49.2 (252) | 50.5 (260) | 50.4 (260) | 0.708 |
| Angina | 22.5 (116) | 21.2 (109) | 23.9 (123) | 0.59 |
| Ischaemic heart disease | 69.2 (355) | 72.8 (375) | 69.6 (359) | 0.898 |
| Atrial fibrillation | 48 (246) | 56.5 (290) | 58.8 (302) | 0.001 |
| Past HF hospitalization | 44.8 (231) | 48.9 (252) | 53.3 (275) | 0.006 |
| PCI | 27.5 (140) | 25.6 (131) | 24.9 (127) | 0.344 |
| CABG | 21.4 (109) | 21.9 (112) | 23.2 (119) | 0.472 |
| Pacemaker | 8 (41) | 13.4 (69) | 13 (67) | 0.012 |
| ACEI/ARB | 77.7 (401) | 78.6 (404) | 71.5 (369) | 0.02 |
| Beta-blocker | 79.1 (408) | 74.5 (383) | 72.5 (374) | 0.014 |
| MRA | 44.6 (230) | 45.9 (236) | 45 (232) | 0.901 |
| Digoxin | 28.7 (148) | 30.7 (158) | 27.3 (141) | 0.631 |
| Standard lab parameters | | | | |
| Albumin (g/dL) | 3.9 [3.6-4.2] | 3.9 [3.6-4.2] | 3.8 [3.5-4] | <0.001 |
| ALT (U/L) | 21 [15-30] | 20 [15-31] | 21 [15-34] | 0.003 |
| AST (U/L) | 24 [18-31] | 25 [19-32.8] | 26 [19-37] | 0.003 |
| Bicarbonate (mEq/L) | 24.5 ± 3.6 | 24.4 ± 3.7 | 23.3 ± 3.8 | <0.001 |
| BUN (mg/dL) | 25 [19-33] | 29 [22-38.2] | 38 [28-51] | <0.001 |
| Chloride (mEq/L) | 101 [99-104] | 101 [99-104] | 101 [97-104] | 0.023 |
| Creatinine (mg/dL) | 1.2 [1-1.5] | 1.4 [1.1-1.7] | 1.6 [1.3-2.1] | <0.001 |
| Total cholesterol (mg/dL) | 151 [126-181.2] | 146 [119-174] | 129 [107.5-159.5] | <0.001 |
| Glucose (mg/dL) | 129.5 [104-171.5] | 126 [103-164] | 128 [101-155] | 0.013 |
| Hemogblobin (g/dL) | 12.8 ± 1.9 | 12.6 ± 1.7 | 12.2 ± 1.9 | <0.001 |
| Platelet count (*10^9/l) | 227 [180-277] | 214.5 [172-266.5] | 207 [161.5-263] | 0.011 |
| Pottasium (mmol/L | 4.3 ± 0.6 | 4.2 ± 0.6 | 4.3 ± 0.6 | 0.22 |
| RBC count (*10^9/l) | 4.3 ± 0.6 | 4.2 ± 0.6 | 4.1 ± 0.6 | <0.001 |
| Sodium (mmol/L) | 140 [138-142] | 140 [138-143] | 139 [136-142] | <0.001 |
| Triglycerides (mmol/L) | 101 [71-138.5] | 83 [63-118] | 81 [61-107] | <0.001 |

TABLE 9-continued

Baseline characteristics by tertiles of MR-proADM

| Variable | Tertile 1 N = 516 | Tertile 2 N = 515 | Tertile 3 N = 516 | P-trend |
|---|---|---|---|---|
| Uric acid (mg/dL) | 8.3 ± 2.4 | 8.9 ± 2.4 | 9.7 ± 2.8 | <0.001 |
| WBC (*10^9/l | 7.7 [6.3-9.2] | 7.3 [6.1-9.1] | 7.2 [5.9-9.3] | 0.591 |
| Hematocrite (%) | 40.4 ± 5.8 | 40 ± 5.5 | 38.9 ± 5.9 | <0.001 |
| Biomarkers | | | | |
| IL-6 (pg/ml) | 9.1 [5.3-16.5] | 10.8 [6.4-19.9] | 14.3 [8.8-26] | 0.037 |
| CRP (ng/ml) | 12566.3 [6334.9-25975.8] | 13306.5 [7168.3-27844.1] | 16044.9 [8412.3-29966.3] | 0.015 |
| D-Dimer (ng/ml) | 134 [90.6-301] | 155.5 [90.6-340.8] | 180.3 [90.6-374.7] | 0.017 |
| PIGR (ng/ml) | 292.2 [197.5-500.4] | 363 [263.5-531.6] | 578.8 [371.4-999] | <0.001 |
| Pentraxin-3 (ng/ml) | 3.4 [2.2-6] | 3.9 [2.8-6] | 5.5 [3.6-8.9] | <0.001 |
| GDF-15 (ng/ml) | 3.6 [2.5-5.8] | 4 [3-6.1] | 6.3 [4.3-6.3] | <0.001 |
| RAGE (ng/ml) | 4.7 [3.4-6.5] | 4.9 [3.6-6.4] | 5.4 [4-7.4] | <0.001 |
| TNF-R1a (ng/ml) | 2.6 [1.7-4] | 2.9 [2.2-3.9] | 4.4 [3.2-5.9] | <0.001 |
| PCT (pg/ml) | 14 [8-31] | 20 [11-41] | 35.5 [18-78] | <0.001 |
| Myeloperoxidase (ng/ml) | 33.9 [17.7-78.5] | 30.9 [18.7-60] | 32.8 [17-66.2] | 0.209 |
| Syndecan-1 (ng/ml) | 7.7 [6.4-9.5] | 8.1 [6.9-9.4] | 9.6 [8.1-11.6] | <0.001 |
| Periostin (ng/ml) | 4 [2.3-6.8] | 5.8 [3.5-8.8] | 7.3 [4.3-11.2] | <0.001 |
| Galectin-3 (ng/ml) | 32 [25.2-43.1] | 34 [26.5-44.1] | 42.7 [32.5-55.9] | <0.001 |
| Osteopontin (ng/ml) | 98.3 [66.3-149.9] | 106.4 [74.2-150.3] | 133.8 [100.7-190.8] | <0.001 |
| ET1 (pg/ml) | 5.7 [4.2-7.6] | 6.7 [5.1-9] | 7.9 [6.1-11] | <0.001 |
| BNP (pg/ml) | 310.8 [189.8-548.6] | 477.2 [262.6-783.3] | 630.1 [341.3-1063] | <0.001 |
| NT-proCNP (pg/ml) | 34 [22-48] | 42 [31-58] | 53 [38-74.2] | <0.001 |
| ST-2 (ng/ml) | 1.8 [0.9-5.6] | 2.8 [1-5.7] | 6.1 [2.7-10.9] | <0.001 |
| VEGFR (ng/ml) | 0.3 [0.2-0.4] | 0.4 [0.2-0.5] | 0.5 [0.3-0.8] | <0.001 |
| Angiogenin (ng/ml) | 1940 [1229.1-2950.6] | 1979.3 [1388.1-3093.5] | 1675.8 [1178.7-2552.6] | 0.007 |
| Mesothelin (ng/ml) | 81.6 [65.6-97] | 83.6 [73.6-94.2] | 94.5 [83.7-108.1] | <0.001 |
| Neuropilin SAND (ng/ml) | 10.6 [6.6-15.8] | 11.6 [8.1-16.8] | 14.8 [10.8-20.4] | <0.001 |
| Troy (pg/ml) | 72 [49-110] | 84 [64-115] | 114 [83-153] | <0.001 |
| bio-ADM | 28 [17.2-53.5] | 42.9 [27.1-74.2] | 70.9 [40.3-120.3] | <0.001 |
| LTBR (ng/ml) | 0.3 [0.2-0.5] | 0.4 [0.3-0.5] | 0.5 [0.4-0.7] | <0.001 |
| ESAM (ng/ml) | 59.2 [53.4-68] | 60.2 [55.6-65.8] | 66.3 [60.5-71.7] | <0.001 |
| KIM-1 (pg/ml) | 273.4 [169.1-484.6] | 296 [181.3-480.4] | 316.8 [199.3-492.9] | 0.485 |
| NGAL (ng/ml) | 64.8 [44.2-98.6] | 81.8 [54.2-123] | 107.2 [70.4-175.2] | <0.001 |
| PSAP-B (ng/ml) | 34 [25.3-49.7] | 36.9 [27.9-47.8] | 45.4 [34.1-61.1] | <0.001 |
| WAP4C (ng/ml) | 18.2 [8.7-38.8] | 22.6 [13.9-38.5] | 45.8 [26.9-67.8] | <0.001 |
| cTnI (pg/ml) | 9.3 [5.1-19.5] | 10.9 [5.6-21.2] | 12.5 [6.3-27.2] | 0.078 |

Example 7

BIOSTAT Study

Additional analyses were performed in the BIOSTAT Study (BIOlogy Study to TAilored Treatment in Chronic Heart Failure). The study has been described in detail (WWW.BIOSTAT-CHF.EU; Voors et al. 2016. *Eur J Heart Fail*, Jun;18(6):716-26). The BIOlogy Study to TAilored Treatment in Chronic Heart Failure (BIOSTAT-CHF) included 2516 patients with worsening signs and/or symptoms of heart failure from 11 European countries, who were considered to be on suboptimal medical treatment. Another 1738 patients from Scotland were included in a validation cohort. Overall, both patient cohorts were well matched. The majority of patients were hospitalized for acute heart failure, and the remainder presented with worsening signs and/or symptoms of heart failure at outpatient clinics. Approximately half of the patients were in New York Heart Association class III, and 7% vs 34% of patients of the index vs validation cohort had heart failure with preserved ejection fraction. According to study design, all patients used diuretics, but owing to the inclusion criteria of both cohorts, patients were not on optimal, evidence-based medical therapy. In the follow-up phase, up-titration to guideline-recommended doses was encouraged.

Study Population

Patients fulfilled the following inclusion criteria:

- aged≥18 years with symptoms of new-onset or worsening heart failure,
- have objective evidence of cardiac dysfunction documented either by,
- left ventricular ejection fraction of ≤40% OR,
- plasma concentrations of BNP and/or N-terminal pro-brain natriuretic peptide (NT-proBNP)>400 pg/mL or >2000 pg/ml, respectively,
- be treated with either oral or intravenous furosemide 240 mg/day or equivalent at the time of inclusion,
- not previously treated with evidence-based therapies [angiotensin-converting enzyme (ACE) inhibitors/angiotensin receptor antagonists (ARBs) and beta-blockers] or receiving≤50% of target doses of these drugs at the time of inclusion,
- be anticipated to be initiated or up-titrated with ACE inhibitors/ARBs and/or beta-blockers by the treating physician.

Patients were enrolled as inpatients or from outpatient clinics. Approximately ⅔ was hospitalized and ⅓ were seen in the outpatient setting.

A subset of patients comprising all types of patients included in the trial (n=1806), for which biomarker measurements at baseline were available, was analyzed in the present invention. Similar to the PROTECT study (example 6) also in the BIOSTAT study increasing levels of bio-ADM were correlated with increasing severity of edema (table 10).

TABLE 10

Baseline clinical variables and standard biomarkers by severity of peripheral edema; BIOSTAT

| | None N = 734 | Ankle N = 532 | Below knee N = 408 | Above knee N = 132 | P-trend |
|---|---|---|---|---|---|
| Age (yrs) | 68 [59.7-76.2] | 70.7 [62.6-78.6] | 72.4 [64.2-78.8] | 74.3 [64.6-80.4] | <0.001 |
| BMI (Kg/m2) | 26.5 [23.9-29.4] | 27.1 [23.9-30.4] | 28.7 [24.8-33.8] | 30.5 [26.2-34.9] | <0.001 |
| LVEF (%) | 30 [25-35] | 30 [25-37] | 30 [23-38] | 35 [25-43.8] | 0.002 |
| DBP (mmHg) | 75.8 ± 12.9 | 74.2 ± 12.8 | 74.3 ± 14.6 | 72.5 ± 13 | 0.004 |
| Heart Rate (bpm) | 75 [65-85] | 78.5 [68.2-90] | 80 [70-92] | 80 [70-92.2] | <0.001 |
| Orthopnea | 21.5 (158) | 40.4 (215) | 50.7 (207) | 61.4 (81) | <0.001 |
| Rales >1/3 lung fields | 5.6 (41) | 10.7 (57) | 16.4 (67) | 28.8 (38) | <0.001 |
| Elevated JVP | 11.2 (82) | 29.7 (158) | 38 (155) | 47 (62) | <0.001 |
| NYHA | | | | | |
| I | 2.7 (20) | 0.8 (4) | 1 (4) | 15.2 (20) | ref. |
| II | 48.2 (354) | 31 (165) | 14.7 (60) | 57.6 (76) | 0.402 |
| III | 39.2 (288) | 53.2 (283) | 62.7 (256) | 21.2 (28) | <0.001 |
| IV | 8.2 (60) | 13.5 (72) | 18.1 (74) | 6.1 (NA) | <0.001 |
| Hepatomegally | 8 (59) | 16.2 (86) | 22.3 (91) | 27.3 (36) | <0.001 |
| Medical history | | | | | |
| Diabetes mellitus | 27.1 (199) | 32.7 (174) | 43.6 (178) | 36.4 (48) | <0.001 |
| Atrial fibrillation | 38.6 (283) | 49.1 (261) | 56.4 (230) | 55.3 (73) | <0.001 |
| ACEI/ARB | 73.8 (542) | 74.6 (397) | 66.7 (272) | 57.6 (76) | <0.001 |
| Beta-blocker | 86.8 (637) | 83.1 (442) | 78.2 (319) | 75 (99) | <0.001 |
| Biomarkers | | | | | |
| ALBUMIN1 (g/L) | 33 [28-39] | 32 [27-37.5] | 31 [26-35] | 30 [24.2-33.8] | <0.001 |
| AST (U/L) | 24 [19-32] | 26 [19-36] | 28 [21-37] | 29 [24-40.8] | 0.003 |
| Gamma-GT (U/L) | 39.7 [24-79.5] | 61 [30-107.8] | 69 [40-142.3] | 98.5 [55-174.5] | <0.001 |
| BUN (mmol/L) | 10.1 [7.1-16.5] | 12.0 [7.8-19.3] | 11.9 [8.3-19.9] | 11.3 [7.4-18.4] | 0.001 |
| Total cholesterol (mmol/L) | 4.4 [3.7-5.2] | 4 [3.3-4.9] | 3.8 [3.1-4.5] | 3.1 [2.8-3.7] | <0.001 |
| Hemogblobin (g/dL) | 13.5 ± 1.8 | 13 ± 1.9 | 13.1 ± 1.9 | 12.4 ± 2.1 | <0.001 |
| Triglycerides (mmol/L) | 1.3 [1-1.8] | 1.2 [0.9-1.5] | 1.1 [0.9-1.5] | 0.9 [0.8-1.2] | <0.001 |
| Hematocrit (%) | 40.6 ± 5.1 | 39.7 ± 5.4 | 39.8 ± 5.6 | 38.3 ± 5.8 | <0.001 |
| BNP (pg/ml) | 489.1 [225-812] | 663.8 [322-1192] | 792.5 [487-1471] | 759.0 [557-2023] | 0.02 |
| bio-ADM (pg/mL) | 26.1 [19.2-37.8] | 36.7 [24.6-54.4] | 52.8 [34.4-86.7] | 82.8 [49.4-141.2] | <0.001 |

In the same sample set also MR-proADM was determined. Baseline characteristics by tertiles of MR-proADM are shown in table 11: Similar to bio-ADM, increasing levels of MR-proADM were associated with increasing extent of edema.

TABLE 11

Baseline characteristics by tertiles of MR-proADM

| Variable N = | Tertile 1 704 | Tertile 2 703 | Tertile 3 703 | P-trend |
|---|---|---|---|---|
| MR-proADM (nmol/L) | 0.3 [0.2-0.3] | 0.5 [0.4-0.6] | 1 [0.8-1.5] | <0.001 |
| Male sex | 74.6 (525) | 72.1 (507) | 73 (513) | 0.498 |
| Age (yrs) | 65.3 [57-73.8] | 71.2 [62.9-78.4] | 74.3 [65.2-80.4] | <0.001 |
| BMI (Kg/m2) | 26.8 [23.9-30.4] | 27.3 [24.2-30.9] | 27.1 [24.1-30.7] | 0.051 |
| LVEF (%) | 30 [25-35] | 30 [25-37.2] | 30 [25-38] | 0.297 |
| SBP (mmHg) | 126.3 ± 20.8 | 125.8 ± 23.4 | 121.2 ± 21.1 | <0.001 |
| DBP (mmHg) | 76.4 ± 13.3 | 75.2 ± 13.3 | 72.3 ± 13 | <0.001 |
| Heart Rate (bpm) | 75 [65-86] | 77 [68-90] | 77 [67-90] | 0.015 |
| Orthopnea present | 23 (162) | 35.8 (252) | 45.1 (317) | <0.001 |
| Rales >1/3 lung fields | 6.4 (45) | 11.9 (84) | 12.9 (91) | 0.074 |

TABLE 11-continued

| Baseline characteristics by tertiles of MR-proADM | | | | |
|---|---|---|---|---|
| Variable<br>N = | Tertile 1<br>704 | Tertile 2<br>703 | Tertile 3<br>703 | P-<br>trend |
| Edema | | | | |
| 0 | 45 (317) | 32.9 (231) | 23.2 (163) | ref. |
| 1+ | 20.5 (144) | 26.3 (185) | 26.5 (186) | <0.001 |
| 2+ | 11.9 (84) | 17.2 (121) | 27.0 (190) | <0.001 |
| 3+ | 2.1 (15) | 4.8 (34) | 11.0 (77) | <0.001 |
| Elevated JVP | 14.9 (105) | 20.9 (147) | 32.4 (228) | <0.001 |
| NYHA | | | | |
| I | 2.7 (19) | 2.6 (18) | 1 (7) | ref. |
| II | 46 (324) | 37.7 (265) | 21.5 (151) | 0.751 |
| III | 40.1 (282) | 48.1 (338) | 55.3 (389) | 0.002 |
| IV | 7.8 (55) | 9.7 (68) | 18.8 (132) | <0.001 |
| Hepatomegally | 9.7 (68) | 12.8 (90) | 19.8 (139) | <0.001 |
| S3 | 9.7 (68) | 9.7 (68) | 9.5 (67) | 0.935 |
| Medical history | | | | |
| COPD | 15.1 (106) | 17.4 (122) | 18.9 (133) | 0.054 |
| Stroke | 7.1 (50) | 10 (70) | 11.5 (81) | 0.005 |
| Peripheral vascular disease | 8.5 (60) | 12.5 (88) | 12.5 (88) | 0.017 |
| Hypertension | 60.8 (428) | 64.3 (452) | 61.3 (431) | 0.842 |
| Diabetes mellitus | 25.6 (180) | 35.3 (248) | 36.7 (258) | <0.001 |
| Myocardial infarction | 29.7 (209) | 39.5 (278) | 42.1 (296) | <0.001 |
| Atrial fibrillation | 37.1 (261) | 46.4 (326) | 53.5 (376) | <0.001 |
| Past HF hospitalization | 27.8 (196) | 30.4 (214) | 34.3 (241) | 0.009 |
| PCI | 17 (120) | 21.2 (149) | 23.6 (166) | 0.002 |
| CABG | 12.2 (86) | 17.8 (125) | 21.8 (153) | <0.001 |
| ACEI/ARB | 75.7 (533) | 73.1 (514) | 66.4 (467) | <0.001 |
| Beta-blocker | 84.9 (598) | 83.5 (587) | 80.1 (563) | 0.016 |
| Standard lab parametrs | | | | |
| Albumin (g/L) | 34 [29-39] | 33 [27-37] | 30 [24-36] | <0.001 |
| ALT (U/L) | 27 [18-40] | 25 [17-39] | 23 [15-35] | 0.452 |
| AST (U/L) | 24 [20-33] | 25.9 [18-35] | 27 [20-36] | 0.087 |
| Gamma-GT (U/L) | 40.8 [25-84] | 52 [28-99] | 76 [32.5-132.4] | <0.001 |
| Alkaline phosphatase (ug/L) | 80 [63-114.8] | 83 [65-111] | 91 [69-123.5] | 0.087 |
| BUN (mmol/L) | 8.9 [6.4-13.3] | 11 [7.4-16.2] | 15 [9.5-25] | <0.001 |
| Creatinine (mg/dL) | 89.3 [75.8-106.1] | 100 [84.6-123.4] | 124.6 [98-167] | 0.61 |
| Total cholesterol (mmol/L) | 4.5 [3.8-5.5] | 4.2 [3.4-4.9] | 3.6 [3-4.5] | <0.001 |
| Glucose (mg/dL) | 6 [5.3-7.5] | 6.4 [5.4-8.5] | 6.5 [5.4-7.9] | 0.22 |
| Hemogblobin (g/dL) | 13.7 ± 1.7 | 13.3 ± 1.8 | 12.5 ± 1.9 | <0.001 |
| Platelet count (*10^9/l) | 221 [183-264] | 220 [173-263] | 208 [161-258] | 0.001 |
| Pottasium (mmol/L | 4.3 [4-4.6] | 4.2 [3.9-4.5] | 4.2 [3.8-4.6] | 0.003 |
| RBC count (*10^12/1) | 4.6 [4.2-5] | 4.5 [4.1-4.9] | 4.2 [3.8-4.7] | <0.001 |
| Sodium (mmol/L) | 140 [138-142] | 140 [137-142] | 139 [136-141] | <0.001 |
| Triglycerides (mmol/L) | 1.3 [1-1.7] | 1.3 [0.9-1.8] | 1.1 [0.9-1.5] | <0.001 |
| WBC (*10^9/l | 7.7 [6.6-9.2] | 8 [6.5-9.8] | 7.7 [6.3-9.7] | 0.529 |
| Hematocrit (%) | 41.3 ± 4.9 | 40.2 ± 5.2 | 38.2 ± 5.4 | <0.001 |
| Biomarkers | | | | |
| IL-6 (pg/ml) | 3.7 [2-6.8] | 5.1 [2.8-8.9] | 8.2 [4.5-16.5] | <0.001 |
| CRP (ng/ml) | 11872.9 [4810.7-25356.7] | 12266.6 [5506.4-25955.3] | 16350.1 [7718.9-29386.1] | 0.004 |
| D-Dimer (ng/ml) | 101.9 [101.9-101.9] | 101.9 [101.9-146.5] | 101.9 [101.9-194.3] | 0.032 |
| PIGR (ng/ml) | 71.5 [44-106.5] | 123.6 [89.8-177.3] | 216.3 [153.8-311.2] | <0.001 |
| Pentraxin-3 (ng/ml) | 1.3 [0.8-2.1] | 2 [1.4-3.1] | 3.3 [2.1-5.2] | <0.001 |
| GDF-15 (ng/ml) | 2.6 [2.2-3.1] | 3.4 [3-4] | 4.4 [3.8-5.3] | <0.001 |
| RAGE (ng/ml) | 2 [1.4-2.7] | 2.9 [2.1-4] | 3.8 [2.8-5] | <0.001 |
| TNF-R1a (ng/ml) | 0.6 [0.3-0.8] | 1 [0.8-1.4] | 1.9 [1.3-2.7] | <0.001 |
| PCT (pg/ml) | 6.2 [3.7-16.1] | 16 [8.2-31.6] | 36.6 [18.9-82.2] | <0.001 |
| Myeloperoxidase (ng/ml) | 24.3 [20.6-30.2] | 28.4 [24.1-34.8] | 31.1 [26.6-38.9] | <0.001 |
| Syndecan-1 (ng/ml) | 1.2 [0.6-2.1] | 2.2 [1.4-3.5] | 3.9 [2.5-6.1] | <0.001 |
| Periostin (ng/ml) | 3.9 [2.3-6.5] | 6.2 [4-9.5] | 9.2 [5.9-14.9] | <0.001 |
| Galectin-3 (ng/ml) | 17.6 [13.2-24.7] | 20.3 [15.4-27] | 26.8 [19.1-37.7] | <0.001 |
| Osteopontin (ng/ml) | 176.3 [147.2-206.4] | 215.4 [187.2-247] | 260.2 [227.7-298.8] | <0.001 |

TABLE 11-continued

| Baseline characteristics by tertiles of MR-proADM | | | | |
|---|---|---|---|---|
| Variable<br>N = | Tertile 1<br>704 | Tertile 2<br>703 | Tertile 3<br>703 | P-<br>trend |
| ET1 (pg/ml) | 4.4 [3.5-5.9] | 5.3 [4-6.7] | 6.6 [5.1-9.1] | <0.001 |
| BNP (pg/ml) | 515 [219.9-957.5] | 598.3 [260.7-1162] | 1032 [639-1641.5] | 0.004 |
| NT-proCNP (pg/ml) | 5.2 [5.2-5.2] | 5.3 [5.2-11.2] | 14.7 [6.2-27.4] | <0.001 |
| ST-2 (ng/ml) | 4.2 [2.3-9.1] | 8.3 [4.5-15.6] | 20.4 [10.1-36.1] | <0.001 |
| VEGFR (ng/ml) | 0.1 [0.1-0.1] | 0.1 [0.1-0.2] | 0.2 [0.1-0.4] | <0.001 |
| Angiogenin (ng/mL) | 6202.1 [4115.9-9654.5] | 4484.4 [3193-6378.8] | 3672 [2629-5151.6] | <0.001 |
| Mesothelin (ng/ml) | 47.7 [42.4-53.1] | 53.7 [48.7-59.5] | 60.4 [54.2-68.8] | <0.001 |
| Neuropilin SAND (ng/ml) | 17 [13.5-20.8] | 21.3 [17.5-25.5] | 26.6 [21.4-31.6] | <0.001 |
| Troy (pg/ml) | 0.1 [0.1-0.2] | 0.3 [0.2-0.4] | 0.4 [0.3-0.7] | <0.001 |
| LTBR (ng/ml) | 0.1 [0.1-0.1] | 0.2 [0.1-0.2] | 0.2 [0.2-0.3] | <0.001 |
| ESAM (ng/ml) | 57.1 [51.6-62.2] | 64.2 [59.2-69.1] | 71 [65.8-78] | <0.001 |
| NGAL (ng/ml) | 45.6 [30.7-72.4] | 59 [37.5-87.6] | 82.7 [51-135.4] | <0.001 |
| PSAP-B (ng/ml) | 25.5 [17.2-33] | 31.6 [24.4-37.4] | 37 [29.4-43.1] | <0.001 |
| WAP4C (ng/ml) | 0.7 [0.5-1.2] | 1.4 [0.9-2.3] | 3.5 [2-6.2] | <0.001 |
| cTnI (pg/ml) | 9.6 [5-23.5] | 12.6 [7.2-27] | 16.5 [9.5-35.9] | 0.098 |

Example 8

Administration of NT-H in Healthy Humans

The study was conducted in healthy male subjects as a randomized, double-blind, placebo-controlled, study with single escalating doses of NT-H antibody administered as intravenous (i.v.) infusion in 3 sequential groups of 8 healthy male subjects each (1st group 0.5 mg/kg, 2nd group 2 mg/kg, 3rd group 8 mg/kg) of healthy male subjects (n=6 active, n=2 placebo for each group).

The main inclusion criteria were written informed consent, age 18-35 years, agreement to use a reliable way of contraception and a BMI between 18 and 30 kg/$m^2$.

Subjects received a single i.v. dose of NT-H antibody (0.5 mg/kg; 2 mg/kg; 8 mg/kg) or placebo by slow infusion over a 1-hour period in a research unit.

The baseline ADM-values in the 4 groups did not differ. Median ADM values were 7.1 µg/mL in the placebo group, 6.8 µg/mL in the first treatment group (0.5 mg/kg), 5.5 µg/mL in second treatment group (2 mg/kg) and 7.1 µg/mL in the third treatment group (8 mg/mL).

Figure 9:
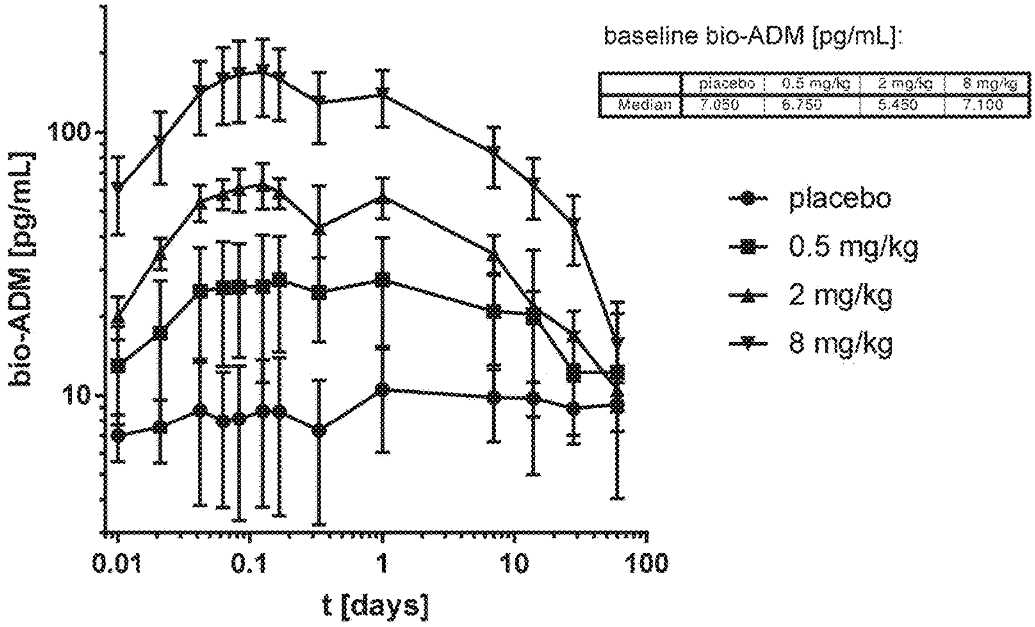

The results show, that ADM-values rapidly increased within the first 1.5 hours after administration of NT-H antibody in healthy human individuals, then reached a plateau and slowly declined (FIG. 9).

Example 9

Administration of NT-H Antibodies in Septic Pigs Two-Hit Model

An established two-hit septic shock model in pigs (Simon T P et al. *Crit Care.* 2012 Jan 25:16(1):R16) was used to induce heart failure and to study the influence of the antibody NT-H on hemodynamic and clinical parameters including heart function.

16 female German Landrace pigs were anaesthetised and ventilated (n=16; mean t standard deviation (SD) 33±1.5 kg body weight (BW)) and followed the standard procedures for laboratory animal care. This study was approved by the institutional and local committee on the care and use of animals (Landesamt für Natur, Umwelt und Verbraucherschutz Nordrhein-Westfalen, Germany, 84-02.04.2015.A037).

Animals were pre-medicated with azaperone (1-2 mg/kg BW) and ketamine (10 mg/kg BW), and general anesthesia was induced by intravenous injection of propofol (1-2 mg/kg BW). The animals were orally intubated and placed in the supine position. General anaesthesia was maintained with infusions of propofol and fentanyl. Controlled pressure mode ventilation was chosen to ventilate the animals with an inspiratory oxygen fraction of 0.5, an inspiratory/expiratory ratio of 1:1.5, PEEP set to 5 cm $H_2O$ and a tidal volume of 8-10 ml/kg BW. The respiratory rate was set to maintain a $PaCO_2$ of 3.5-4.5 kPa. The body core temperature was maintained above 37.5° C. with a warming blanket. Two central venous catheter were inserted into the external jugular vein and the femoral vein and an arterial PICCO catheter was inserted into the femoral artery by transcutaneous puncture.

At the end of the study the animals were euthanised in the presence of a veterinarian with a lethal dose of Narcoren® (Merial, Hallbergmoos, Germany) while they were still under deep narcosis.

In this model, we used an *E. coli*-laden clot with 7-9×$10^{11}$ colony-forming units (CFUs) per kg/BW to induce septic shock.

Haemodynamic Measurements:

All intravascular pressure measurements were referenced to the mid-chest level, and values were obtained at end-expiration. Heart rate, mean arterial pressure (MAP), central venous pressure (CVP) and stroke volume variation (SVV) were recorded continuously. Cardiac output (CO) was measured using transpulmonary thermodilution (PICCO, Pulsion medical systems, Feldkirchen, Germany). Extravascular lung water (EVLW), intrathoracic blood volume (ITBV) and global end-diastolic volume (GEDV) were calculated using standard formula.

Figure 10:
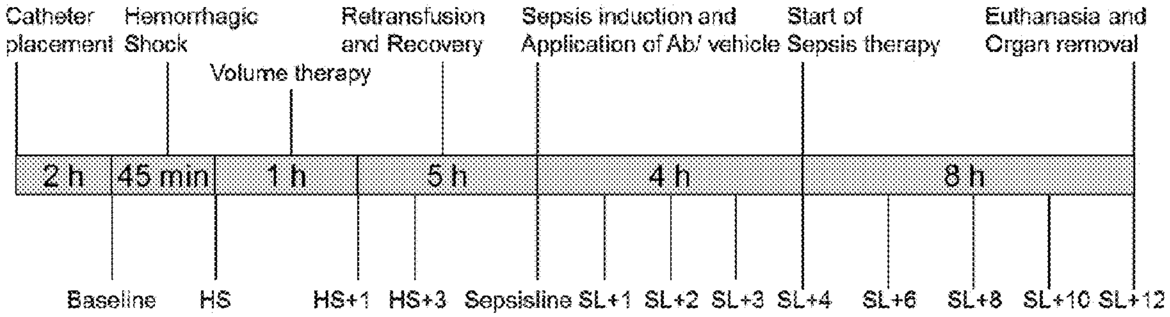

Experimental Protocol:

During catheterisation animals received 10 ml/kg BW/hr of a balanced crystalloid solution. Haemorrhagic shock was induced by bleeding the animals via the femoral vein catheter. The animals were bled until half of the baseline MAP was reached. Haemorriagic shock was maintained for 45 minutes, followed by fluid resuscitation with a balanced crystalloid solution in order to restore baseline mean arterial pressure. 2 hours after haemorrhagic shock the blood collected during haemorrhagic shock was re-transfused. As second hit, sepsis was induced using an *E. coli*-laden clot placed into the abdominal cavity 6 hours after haemorrhagic shock. Animals were randomly allocated to receive either the adrenomedullin antibody or the vehicle solution. The therapy with the antibody or vehicle solution started immediately after the induction of sepsis. 2 mg/kg BW of the antibody/vehicle solution were infused over a period of 30 minutes. 4 hours after sepsis had been induced the therapy of the septic shock started using balanced crystalloids and noradrenalin on demand. Volume replacement and vasopressor were titrated to maintain a central venous pressure of 8-12 mmHg, a mean arterial pressure above 65 mmHg and a central venous oxygen saturation of 70%, as recommended by the Surviving Sepsis Campaign. Sepsis therapy continued for another 8 hours. EDTA-Plasma and serum samples for several measurements were gained before haemorrhagic shock, before sepsis induction and 1, 2, 3, 4, 6, 8, 10 and 12 hours after sepsis induction, and stored at −80° C. until measurement. Haemorrhagic and septic shock were not performed on the animals of the SHAM-groups, but apart from that, they received the same treatment including all intravascular catheter, the median laparotomy and the blinded application of the antibody/vehicle solution, and blood samples were drawn as in septic animals. The time schedule for treatment and drawing of blood samples is shown in FIG. 10.

Figure 11:
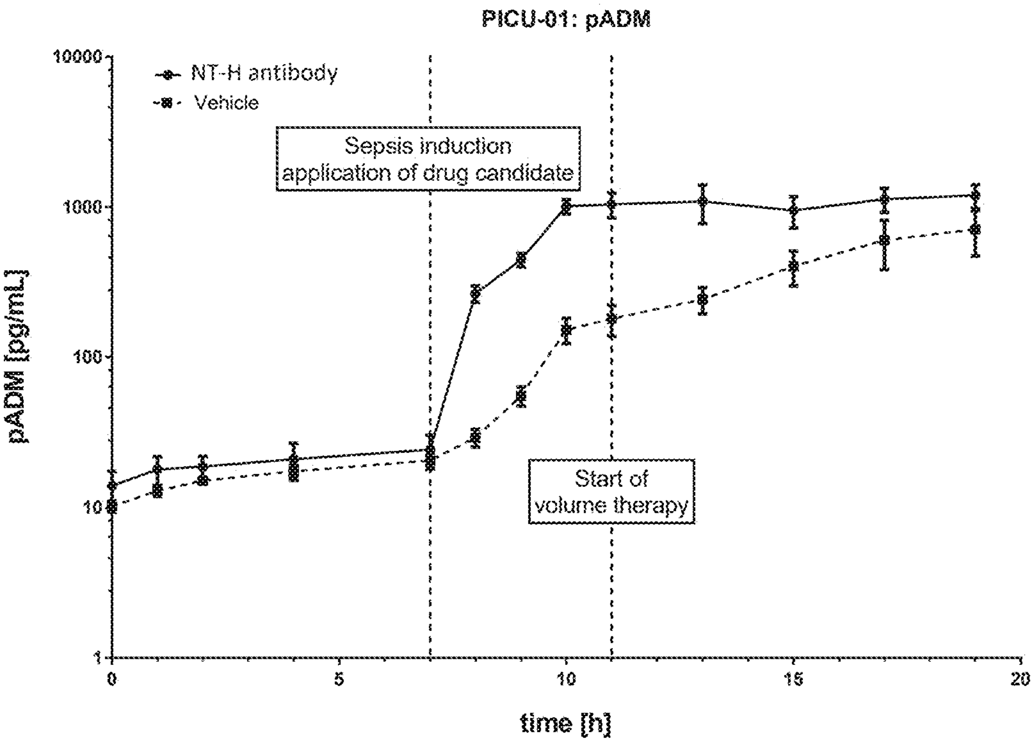

As expected, the ADM plasma concentration started to increase after sepsis induction in both groups. This increase was accelerated by the administration of NT-H antibody together with the sepsis induction. While the vehicle group showed an increase to approximately 30 pg/mL at one hour after sepsis induction, the treatment group showed 265 pg/mL at the same time point. The treatment reached a steady state of approximately 1,100 pg/mL 3 hours after application of NT-H antibody, while the vehicle group showed a constant increase of ADM concentration up to 700 pg/mL at the end of the experiment (FIG. 11). Application of NT-H antibodies also induced an increase of plasma ADM in sham control animals. This is analogous to results seen in healthy humans (Example 8).

Figure 12:
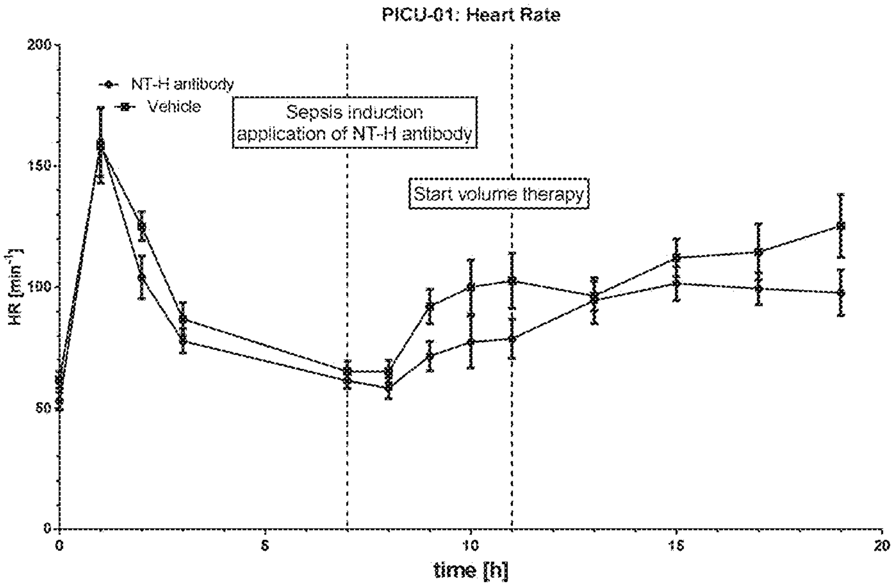

The heart rate (HR) increased at the point of blood removal for hemorrhagic shock in order to compensate the loss of volume and returned to initial values after volume replacement with crystalloid solution and blood. After sepsis induction the heart rate remained constant at 60-65 $min^{-1}$ for the first hour and started afterwards to increase, where the rate of increase was higher in the vehicle group compared to the antibody treatment group with end values of 125 $min^{-1}$ (vehicle) compared to 98 $min^{-1}$ (treatment) (FIG. 12).

Figure 13:
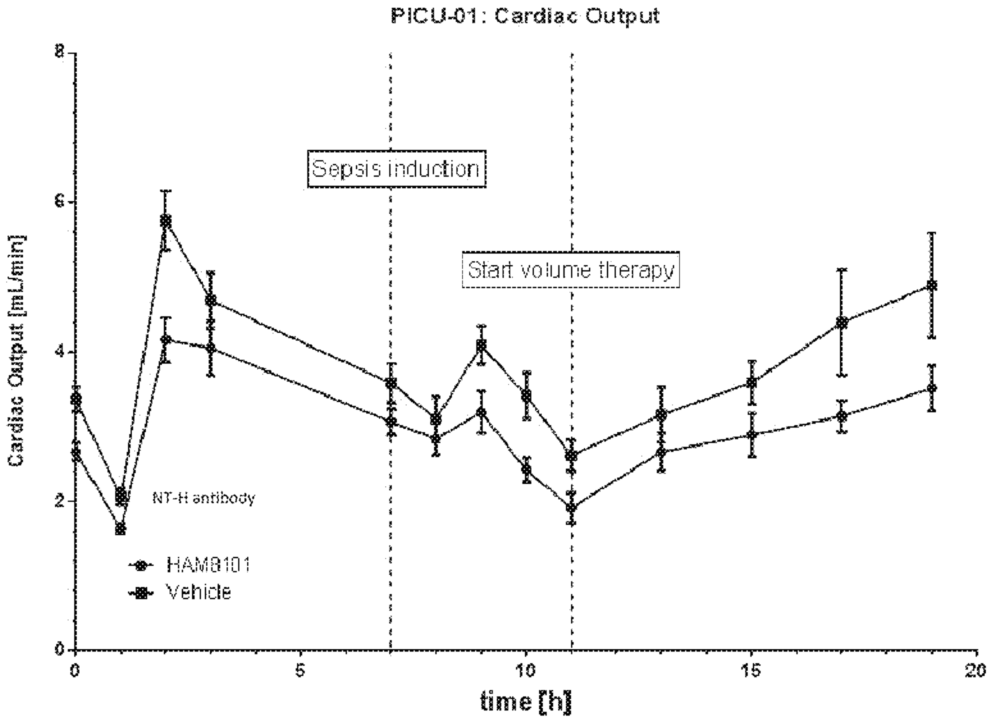

Cardiac output (CO) describes the volume of blood being pumped by the heart, in particular by a left or right ventricle, per unit time. CO values can be represented using many physical units, such as L/min. The cardiac output in this study was significantly lower in the NT-H antibody treated group compared to the vehicle group (FIG. 13).

Figure 14:
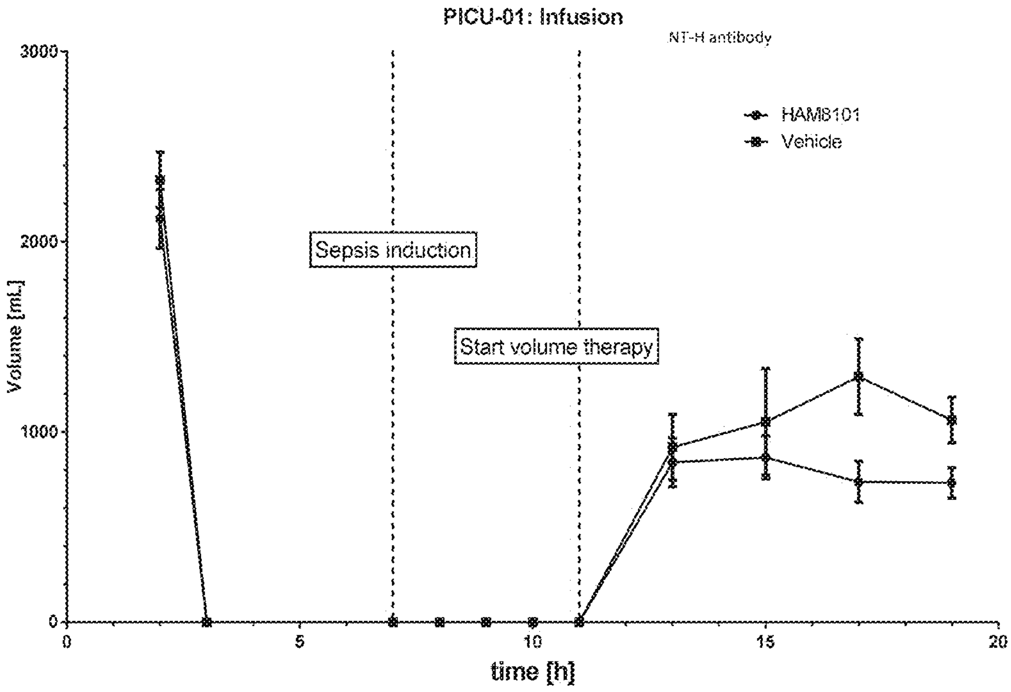
Figure 15:
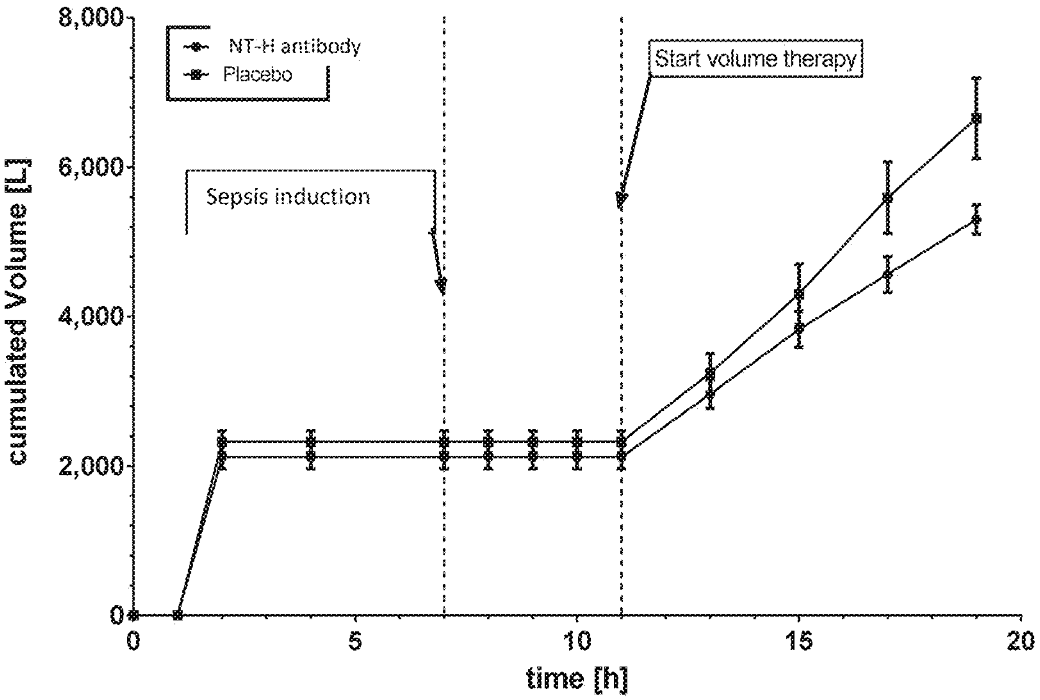
Figure 16:
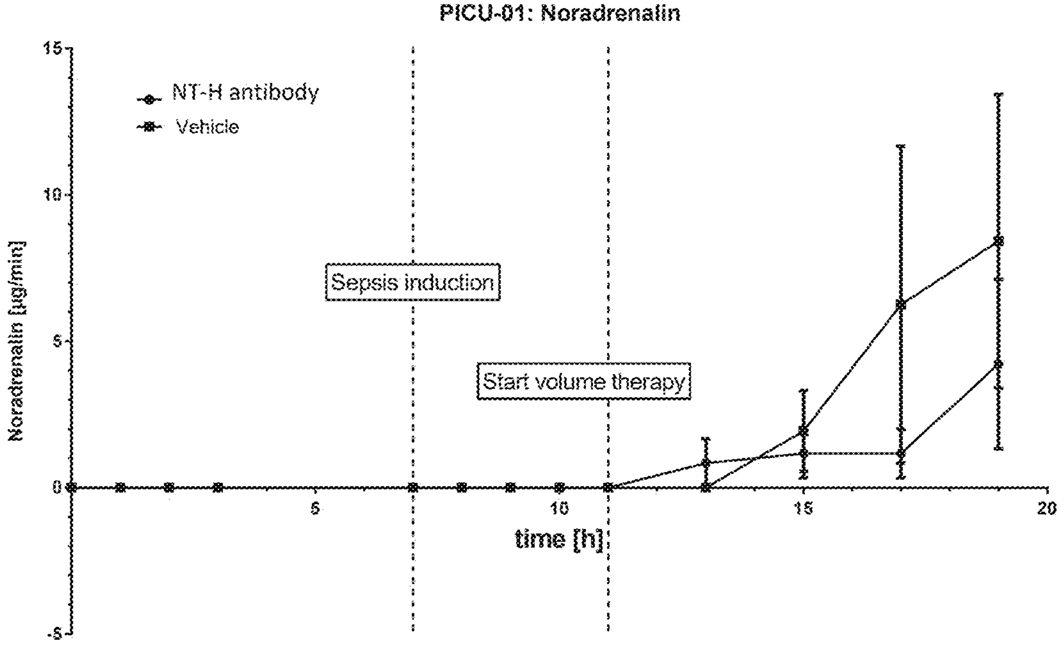
Figure 17:
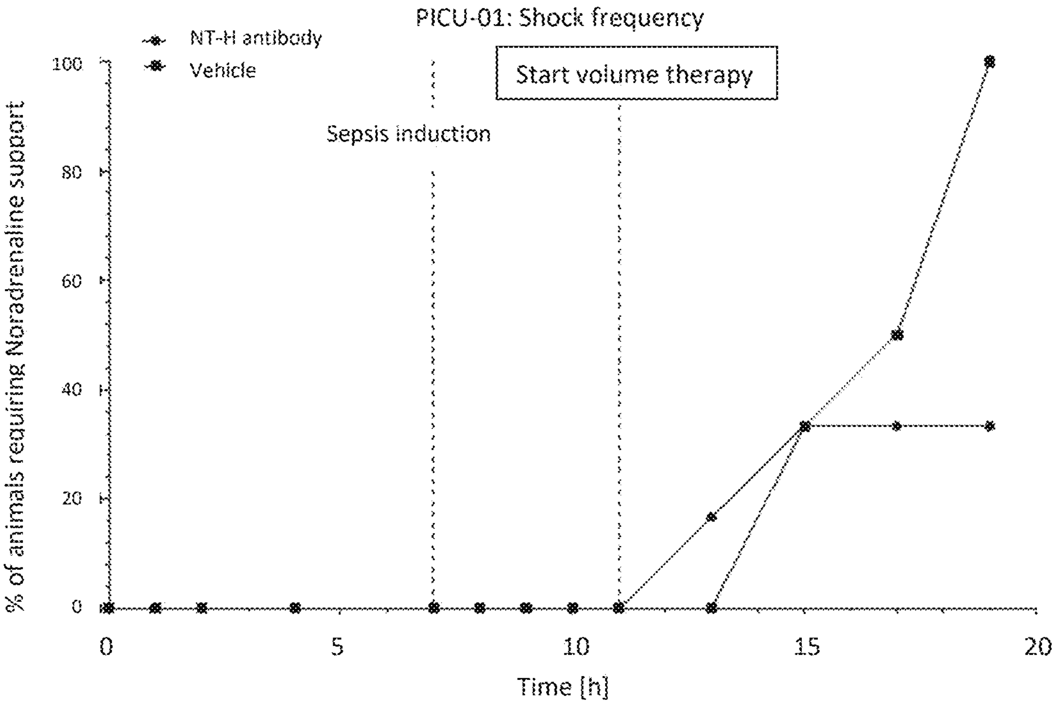

The demand of fluid (FIGS. 14 and 15) and Noradrenalin (FIG. 16) for maintaining a constant mean arterial pressure was considerably less for the NT-H antibody treatment group compared to the vehicle group. Importantly, only one third of the NT-H-treated animals went into shock (e.g. required vasopressor support to maintain the target MAP), whereas all vehicle controls required vasopressor (FIG. 17). Urine output did not differ between the NT-H antibody treatment group and the vehicle group. The reduced requirement for fluids upon application of NT-H antibodies, especially also under consideration of the reduced requirement for Noradrenalin, demonstrates that less fluid had evaded from the blood circulation and thus less congestion had occurred in the NT-H antibody treatment group.

Figure 18:
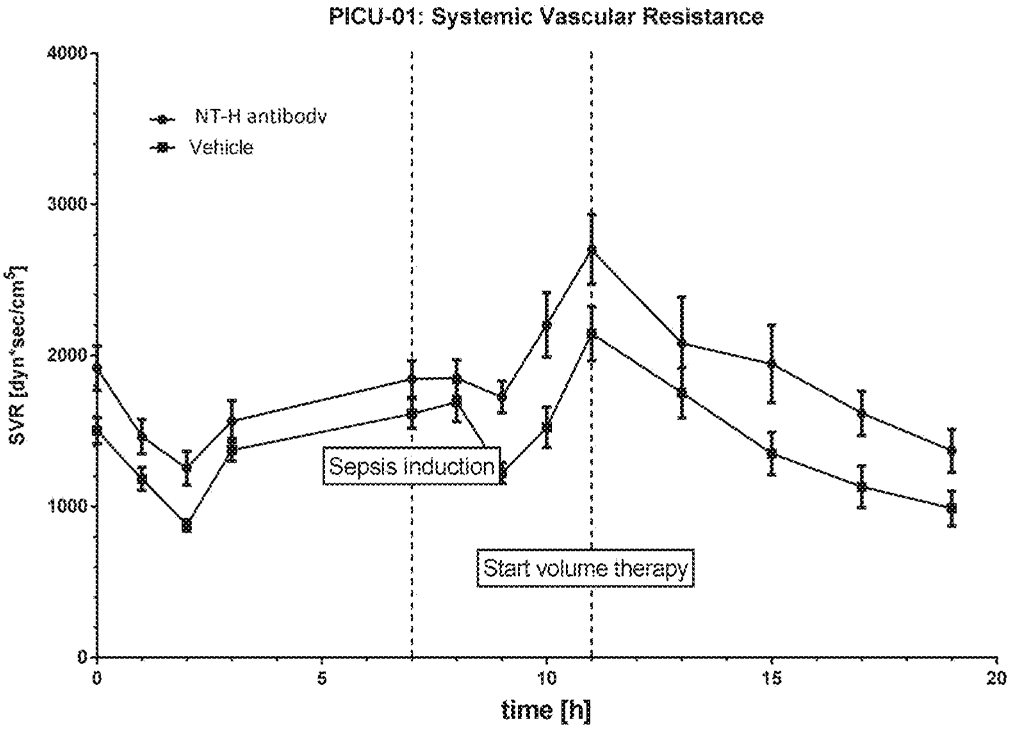

Vascular resistance refers to the resistance to blood flow offered by all of the systemic vasculature, excluding the pulmonary vasculature. Systemic vascular resistance (SVR) is used in calculations of blood pressure, blood flow, and cardiac function. SVR, in units of dyn·s·$cm^5$, was calculated from other measurements using the following formula:

SVR=80×(MAP−CVP)/CO. SVR increases to tighten the arterial vascular circuit in an attempt to maintain blood pressure. As shown in FIG. 18, the systemic vascular resistance in this animal model was higher in the NT-H treated group compared to the vehicle group.

Example 10

Administration of NT-H in LPS-Induced Rat Endotoxemia

The aim of this study was to examine the effect of HAM8101, an antibody binding to the N-terminus of ADM (NT-H), on vascular permeability in liver and kidney following LPS-induced endotoxemia in rats.

Doses of 0.02, 0.1, 0.5, and 2.5 mg HAM8101/kg b.w. or PBS were i.v. applied (single bolus injection) to male Wistar rats (n=8/group) (see Table 12). Five minutes later, 2.5 or 5 mg LPS/kg b.w. were applied to induce endotoxemia (the 2.5 mg LPS/kg group was only used to test suitable LPS dose and was not further evaluated). Blood samples were taken 3, 6 and 24 hours after application of LPS and HAM8101.

24 hours after application of LPS-solution Evans Blue was slowly applied via tail vein injection and animals were killed 15 minutes later and perfused with heparinized saline (50 IU/mL). Kidney and liver were removed, weighed and chopped and after further manipulation concentration of Evans Blue were determined in tissue (spectroscopic absorbance at 620 nm) being indicative for vascular permeability. Additionally, urine was collected from the bladder prior perfusion.

TABLE 12

Experimental Groups and Doses

| Group | HAM8101 Dose [mg/kg] | LPS Dose [mg/kg] | N |
|---|---|---|---|
| A (Control) | NaCl | NaCl | 8 |
| B (Placebo; only test for suitable LPS dose, not further evaluated) | NaCl | 2.5 | 6 |
| C (Placebo) | NaCl | 5 | 8 |
| D | 2.5 | 5 | 8 |
| E | 0.5 | 5 | 8 |
| F | 0.1 | 5 | 8 |
| G | 0.02 | 5 | 8 |

The time course of the rADM plasma concentrations for the placebo (NaCl+LPS) group showed an increase over the first 6 hours after LPS application to a peak plasma concentration of 140 pg/mL with a subsequent decrease to 64 pg/mL at 24 hours.

Levels of total rADM were further increased upon HAM8101 treatment in a dose-dependent way with peak rADM concentrations of 550 pg/mL for 2.5 and 270 pg/mL for 0.5 mg/kg reached at 3 hours after LPS and HAM8101 application. The lower doses of 0.1 and 0.02 mg/kg did not show any further increase compared to the LPS-induced increase of rADM (19A). When normalizing the total rADM levels to those achieved in the placebo group at the respective time points the levels at the maximum peak increased by a factor of 5.3 and 2.7 in the 2.5 and 0.5 mg/kg group, respectively. This increase in total plasma ADM concentration compared to baseline is higher than in healthy animals (factor 3 for 2.5 mg/kg) and septic mice (factor 2). The lower doses of 0.1 and 0.02 mg/kg did not show any increase in total rADM levels exceeding the levels achieved by LPS alone (19B).

Rats were treated with NaCl (healthy, green) or LPS at 5 mg/kg b.w (placebo, red); rats were further treated either with NaCl (placebo, red) or HAM8101 (blue) at different doses with a single i.v. bolus injection 5 minutes prior to LPS application. Levels of rADM were determined 3, 6, and 24 hours after LPS application and are presented as (A) mean values±SEM or (B) as x-fold induction compared to placebo group at respective time-point Vascular permeability was significantly increased after LPS challenge. There was a clear and significant reduction of vascular permeability upon treatment with HAM8101 at doses of 0.1 to 2.5 mg/kg HAM8101 in kidneys (see FIG. 20A). At a dose of 0.1 mg/kg the restoration of permeability back to a normal healthy state was significantly more efficacious compared to the doses of 0.5 and even 2.5 mg/kg ($p<0.05$). Whether this effect is reliable needs to be validated in additional studies. In contrast nearly no beneficial effect on vascular permeability was noted at 0.02 mg/kg. The data for vascular permeability in liver showed a comparable trend, but without being statistically significant (see FIG. 20B).

Rats were treated with NaCl (control, green) or LPS at 5 mg/kg b.w (placebo, red); rats were further treated either with NaCl (placebo, red) or HAM8101 (blue) at different doses with a single i.v. bolus injection 5 minutes prior to LPS application. Vascular permeability was measured by determination of Evans Blue concentration in (A) kidney and (B) liver tissue 24 hours after LPS challenge and treatment. Values are given as mean±SEM; p-values of <0.05 were considered statistically significant.

In conclusion, in this rat endotoxemia model treatment with HAM8101 at doses starting from 0.1 mg/kg led to a significant restoration of vascular integrity in the kidney. For the liver a comparable effect was observed, which, however, was not statistically significant. It is unclear whether this is a real effect or due to the applied detection method. A significant increase in total plasma rADM levels at HAM8101 doses above 0.1 mg/kg was noted.

SEQUENCE LISTING

```
<160> NUMBER OF SEQ ID NOS: 36

<210> SEQ ID NO 1
<211> LENGTH: 8
<212> TYPE: PRT
<213> ORGANISM: human

<400> SEQUENCE: 1

Gly Tyr Thr Phe Ser Arg Tyr Trp
1               5


<210> SEQ ID NO 2
<211> LENGTH: 8
<212> TYPE: PRT
<213> ORGANISM: human

<400> SEQUENCE: 2

Ile Leu Pro Gly Ser Gly Ser Thr
1               5


<210> SEQ ID NO 3
<211> LENGTH: 11
<212> TYPE: PRT
<213> ORGANISM: human

<400> SEQUENCE: 3

Thr Glu Gly Tyr Glu Tyr Asp Gly Phe Asp Tyr
1               5                   10


<210> SEQ ID NO 4
<211> LENGTH: 11
<212> TYPE: PRT
<213> ORGANISM: human

<400> SEQUENCE: 4

Gln Ser Ile Val Tyr Ser Asn Gly Asn Thr Tyr
1               5                   10


<210> SEQ ID NO 5
<211> LENGTH: 9
<212> TYPE: PRT
```

<213> ORGANISM: human

<400> SEQUENCE: 5

```
Phe Gln Gly Ser His Ile Pro Tyr Thr
1               5
```

<210> SEQ ID NO 6
<211> LENGTH: 225
<212> TYPE: PRT
<213> ORGANISM: human

<400> SEQUENCE: 6

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225
```

<210> SEQ ID NO 7
<211> LENGTH: 225
<212> TYPE: PRT
<213> ORGANISM: human

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Arg Tyr
            20                  25                  30

Trp Ile Ser Trp Val Arg Gln Ala Pro Gly Gln Gly Leu Glu Trp Met
        35                  40                  45

Gly Arg Ile Leu Pro Gly Ser Gly Ser Thr Asn Tyr Ala Gln Lys Phe
    50                  55                  60
```

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Thr Glu Gly Tyr Glu Tyr Asp Gly Phe Asp Tyr Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys His His His His His
210 215 220

His
225

<210> SEQ ID NO 8
<211> LENGTH: 225
<212> TYPE: PRT
<213> ORGANISM: human

<400> SEQUENCE: 8

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Arg Tyr
20 25 30

Trp Ile Glu Trp Val Arg Gln Ala Pro Gly Gln Gly Leu Glu Trp Met
35 40 45

Gly Arg Ile Leu Pro Gly Ser Gly Ser Thr Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Thr Glu Gly Tyr Glu Tyr Asp Gly Phe Asp Tyr Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser

-continued

```
        195                 200                 205

Asn Thr Lys Val Asp Lys Arg Val Glu Pro Lys His His His His His
    210                 215                 220

His
225


<210> SEQ ID NO 9
<211> LENGTH: 225
<212> TYPE: PRT
<213> ORGANISM: human

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Ser Arg Tyr
            20                  25                  30

Trp Ile Ser Trp Val Arg Gln Ala Pro Gly Gln Gly Leu Glu Trp Met
        35                  40                  45

Gly Glu Ile Leu Pro Gly Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225


<210> SEQ ID NO 10
<211> LENGTH: 225
<212> TYPE: PRT
<213> ORGANISM: human

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Thr Gly Tyr Thr Phe Ser Arg Tyr
            20                  25                  30

Trp Ile Glu Trp Val Arg Gln Ala Pro Gly Gln Gly Leu Glu Trp Met
        35                  40                  45

Gly Glu Ile Leu Pro Gly Ser Gly Ser Thr Asn Tyr Ala Gln Lys Phe
```

```
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Glu Gly Tyr Glu Tyr Asp Gly Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys His His His His His
    210                 215                 220

His
225


<210> SEQ ID NO 11
<211> LENGTH: 219
<212> TYPE: PRT
<213> ORGANISM: human

<400> SEQUENCE: 11

Asp Val Leu Leu Ser Gln Thr Pro Leu Ser Leu Pro Val Ser Leu Gly
1               5                   10                  15

Asp Gln Ala Thr Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 12
<211> LENGTH: 219
<212> TYPE: PRT
<213> ORGANISM: human

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Arg Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 13
<211> LENGTH: 219
<212> TYPE: PRT
<213> ORGANISM: human

<400> SEQUENCE: 13

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Arg Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 14
<211> LENGTH: 21
<212> TYPE: PRT
<213> ORGANISM: human

<400> SEQUENCE: 14

Tyr Arg Gln Ser Met Asn Asn Phe Gln Gly Leu Arg Ser Phe Gly Cys
1               5                   10                  15

Arg Phe Gly Thr Cys
            20


<210> SEQ ID NO 15
<211> LENGTH: 12
<212> TYPE: PRT
<213> ORGANISM: human

<400> SEQUENCE: 15

Cys Thr Val Gln Lys Leu Ala His Gln Ile Tyr Gln
1               5                   10


<210> SEQ ID NO 16
<211> LENGTH: 12
<212> TYPE: PRT
<213> ORGANISM: human

<400> SEQUENCE: 16

Cys Ala Pro Arg Ser Lys Ile Ser Pro Gln Gly Tyr
1               5                   10


<210> SEQ ID NO 17
<211> LENGTH: 19
<212> TYPE: PRT
<213> ORGANISM: murine

<400> SEQUENCE: 17

Tyr Arg Gln Ser Met Asn Gln Gly Ser Arg Ser Asn Gly Cys Arg Phe
1               5                   10                  15

Gly Thr Cys


<210> SEQ ID NO 18
<211> LENGTH: 12
```

-continued

<212> TYPE: PRT
<213> ORGANISM: murine

<400> SEQUENCE: 18

Cys Thr Phe Gln Lys Leu Ala His Gln Ile Tyr Gln
1 5 10

<210> SEQ ID NO 19
<211> LENGTH: 12
<212> TYPE: PRT
<213> ORGANISM: murine

<400> SEQUENCE: 19

Cys Ala Pro Arg Asn Lys Ile Ser Pro Gln Gly Tyr
1 5 10

<210> SEQ ID NO 20
<211> LENGTH: 52
<212> TYPE: PRT
<213> ORGANISM: human

<400> SEQUENCE: 20

Tyr Arg Gln Ser Met Asn Asn Phe Gln Gly Leu Arg Ser Phe Gly Cys
1 5 10 15

Arg Phe Gly Thr Cys Thr Val Gln Lys Leu Ala His Gln Ile Tyr Gln
20 25 30

Phe Thr Asp Lys Asp Lys Asp Asn Val Ala Pro Arg Ser Lys Ile Ser
35 40 45

Pro Gln Gly Tyr
50

<210> SEQ ID NO 21
<211> LENGTH: 50
<212> TYPE: PRT
<213> ORGANISM: murine

<400> SEQUENCE: 21

Tyr Arg Gln Ser Met Asn Gln Gly Ser Arg Ser Asn Gly Cys Arg Phe
1 5 10 15

Gly Thr Cys Thr Phe Gln Lys Leu Ala His Gln Ile Tyr Gln Leu Thr
20 25 30

Asp Lys Asp Lys Asp Gly Met Ala Pro Arg Asn Lys Ile Ser Pro Gln
35 40 45

Gly Tyr
50

<210> SEQ ID NO 22
<211> LENGTH: 21
<212> TYPE: PRT
<213> ORGANISM: human

<400> SEQUENCE: 22

Tyr Arg Gln Ser Met Asn Asn Phe Gln Gly Leu Arg Ser Phe Gly Cys
1 5 10 15

Arg Phe Gly Thr Cys
20

<210> SEQ ID NO 23
<211> LENGTH: 42
<212> TYPE: PRT
<213> ORGANISM: human

<400> SEQUENCE: 23

Tyr Arg Gln Ser Met Asn Asn Phe Gln Gly Leu Arg Ser Phe Gly Cys
1 5 10 15

Arg Phe Gly Thr Cys Thr Val Gln Lys Leu Ala His Gln Ile Tyr Gln
20 25 30

Phe Thr Asp Lys Asp Lys Asp Asn Val Ala
35 40

<210> SEQ ID NO 24
<211> LENGTH: 10
<212> TYPE: PRT
<213> ORGANISM: human

<400> SEQUENCE: 24

Pro Arg Ser Lys Ile Ser Pro Gln Gly Tyr
1 5 10

<210> SEQ ID NO 25
<211> LENGTH: 14
<212> TYPE: PRT
<213> ORGANISM: human

<400> SEQUENCE: 25

Tyr Arg Gln Ser Met Asn Asn Phe Gln Gly Leu Arg Ser Phe
1 5 10

<210> SEQ ID NO 26
<211> LENGTH: 10
<212> TYPE: PRT
<213> ORGANISM: human

<400> SEQUENCE: 26

Tyr Arg Gln Ser Met Asn Asn Phe Gln Gly
1 5 10

<210> SEQ ID NO 27
<211> LENGTH: 6
<212> TYPE: PRT
<213> ORGANISM: human

<400> SEQUENCE: 27

Tyr Arg Gln Ser Met Asn
1 5

<210> SEQ ID NO 28
<211> LENGTH: 32
<212> TYPE: PRT
<213> ORGANISM: human

<400> SEQUENCE: 28

Tyr Arg Gln Ser Met Asn Asn Phe Gln Gly Leu Arg Ser Phe Gly Cys
1 5 10 15

Arg Phe Gly Thr Cys Thr Val Gln Lys Leu Ala His Gln Ile Tyr Gln
20 25 30

<210> SEQ ID NO 29
<211> LENGTH: 40
<212> TYPE: PRT
<213> ORGANISM: murine

<400> SEQUENCE: 29

Tyr Arg Gln Ser Met Asn Gln Gly Ser Arg Ser Asn Gly Cys Arg Phe
1 5 10 15

```
Gly Thr Cys Thr Phe Gln Lys Leu Ala His Gln Ile Tyr Gln Leu Thr
            20                  25                  30

Asp Lys Asp Lys Asp Gly Met Ala
        35                  40


<210> SEQ ID NO 30
<211> LENGTH: 31
<212> TYPE: PRT
<213> ORGANISM: murine

<400> SEQUENCE: 30

Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu
            20                  25                  30


<210> SEQ ID NO 31
<211> LENGTH: 164
<212> TYPE: PRT
<213> ORGANISM: human

<400> SEQUENCE: 31

Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
            20                  25                  30

Thr Gly Leu Ala Asp Val Lys Ala Gly Pro Ala Gln Thr Leu Ile Arg
        35                  40                  45

Pro Gln Asp Met Lys Gly Ala Ser Arg Ser Pro Glu Asp Ser Ser Pro
    50                  55                  60

Asp Ala Ala Arg Ile Arg Val Lys Arg Tyr Arg Gln Ser Met Asn Asn
65                  70                  75                  80

Phe Gln Gly Leu Arg Ser Phe Gly Cys Arg Phe Gly Thr Cys Thr Val
                85                  90                  95

Gln Lys Leu Ala His Gln Ile Tyr Gln Phe Thr Asp Lys Asp Lys Asp
            100                 105                 110

Asn Val Ala Pro Arg Ser Lys Ile Ser Pro Gln Gly Tyr Gly Arg Arg
        115                 120                 125

Arg Arg Arg Ser Leu Pro Glu Ala Gly Pro Gly Arg Thr Leu Val Ser
    130                 135                 140

Ser Lys Pro Gln Ala His Gly Ala Pro Ala Pro Pro Ser Gly Ser Ala
145                 150                 155                 160

Pro His Phe Leu


<210> SEQ ID NO 32
<211> LENGTH: 20
<212> TYPE: PRT
<213> ORGANISM: human

<400> SEQUENCE: 32

Ala Arg Leu Asp Val Ala Ser Glu Phe Arg Lys Lys Trp Asn Lys Trp
1               5                   10                  15

Ala Leu Ser Arg
            20


<210> SEQ ID NO 33
<211> LENGTH: 48
<212> TYPE: PRT
```

<213> ORGANISM: human

<400> SEQUENCE: 33

```
Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45
```

<210> SEQ ID NO 34
<211> LENGTH: 53
<212> TYPE: PRT
<213> ORGANISM: human

<400> SEQUENCE: 34

```
Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr Gly
    50
```

<210> SEQ ID NO 35
<211> LENGTH: 76
<212> TYPE: PRT
<213> ORGANISM: human

<400> SEQUENCE: 35

```
Arg Arg Arg Arg Arg Ser Leu Pro Glu Ala Gly Pro Gly Arg Thr Leu
1               5                   10                  15

Val Ser Ser Lys Pro Gln Ala His Gly Ala Pro Ala Pro Pro Ser Gly
            20                  25                  30

Ser Ala Pro His Phe Leu Arg Arg Arg Arg Arg Ser Leu Pro Glu Ala
        35                  40                  45

Gly Pro Gly Arg Thr Leu Val Ser Ser Lys Pro Gln Ala His Gly Ala
    50                  55                  60

Pro Ala Pro Pro Ser Gly Ser Ala Pro His Phe Leu
65                  70                  75
```

<210> SEQ ID NO 36
<211> LENGTH: 118
<212> TYPE: PRT
<213> ORGANISM: human

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

-continued

```
Met Glu Leu Ser Ser Leu Arg Ser Glu Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser
        115
```

The invention claimed is:

1. A method for the treatment of residual congestion in a patient with heart failure who has been treated with diuretics, wherein residual congestion is defined as the presence of congestion after the treatment with diuretics the method comprising:

administering to a patient in the need thereof, an effective amount of Anti-adrenomedullin (ADM) antibody or an anti-ADM-antibody fragment, wherein said anti-ADM antibody or anti-ADM-antibody fragment binds to the N-terminal part (aa 1-21) of adrenomedullin:

(SEQ ID NO: 22)
YRQSMNNFQGLRSFGCRFGTC;

wherein the anti-adrenomedullin (ADM) antibody or an anti-ADM-antibody fragment comprises a heavy chain and a light chain, wherein the heavy chain comprises the sequences:

SEQ ID NO: 1
GYTFSRYW,

SEQ ID NO: 2
ILPGSGST,
and

SEQ ID NO: 3
TEGYEYDGFDY and wherein the light chain comprises the sequences:

SEQ ID NO: 4
QSIVYSNGNTY,

SEQUENCE: RVS,
and

SEQ ID NO: 5
FQGSHIPYT.

2. The method according to claim 1, wherein said antibody or fragment thereof is humanized.

3. A method according to claim 1, wherein said humanized monoclonal antibody or fragment blocks the bioactivity of ADM not more than 80%, preferably not more than 50%.

4. A method according to claim 1, wherein said patient is an ICU patient.

5. A method according to claim 1, wherein said antibody or fragment comprises a sequence selected from the group consisting of:

(AM-VH-C)
SEQ ID NO: 6
QVQLQQSGAELMKPGASVKISCKATGYTFSRYWIEWVKQRPGHGLEWIGE
ILPGSGSTNYNEKFKGKATITADTSSNTAYMQLSSLTSEDSAVYYCTEGY

-continued

EYDGFDYWGQGTTLTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNT KVDKRVEPKHHHHHH, (AM-VH1)
SEQ ID NO: 7
QVQLVQSGAEVKKPGSSVKVSCKASGYTFSRYWISWVRQAPGQGLEWMGR
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH, (AM-VH2-E40)
SEQ ID NO: 8
QVQLVQSGAEVKKPGSSVKVSCKASGYTFSRYWIEWVRQAPGQGLEWMGR
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH, (AM-VH3-T26-E55)
SEQ ID NO: 9
QVQLVQSGAEVKKPGSSVKVSCKATGYTFSRYWISWVRQAPGQGLEWMGE
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH, (AM-VH4-T26-E40-E55)
SEQ ID NO: 10
QVQLVQSGAEVKKPGSSVKVSCKATGYTFSRYWIEWVRQAPGQGLEWMGE
ILPGSGSTNYAQKFQGRVTITADESTSTAYMELSSLRSEDTAVYYCTEGY
EYDGFDYWGQGTTVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKHHHHHH, (AM-VL-C)
SEQ ID NO: 11
DVLLSQTPLSLPVSLGDQATISCRSSQSIVYSNGNTYLEWYLQKPGQSPK
LLIYRVSNRFSGVPDRFSGSGSGTDFTLKISRVEAEDLGVYYCFQGSHIP
YTFGGGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSF NRGEC,

-continued (AM-VL1)

SEQ ID NO: 12

DVVMTQSPLSLPVTLGQPASISCRSSQSIVYSNGNTYLNWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKS FNRGEC, and (AM-VL2-E40)

SEQ ID NO: 13

DVVMTQSPLSLPVTLGQPASISCRSSQSIVYSNGNTYLEWFQQRPGQSPR

RLIYRVSNRDSGVPDRFSGSGSGTDFTLKISRVEAEDVGVYYCFQGSHIP

YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKS FNRGEC.

6. A method for the treatment of residual congestion in a patient with heart failure who has been treated with diuretics, wherein residual congestion is defined as the presence of congestion after the treatment with diuretics, the method comprising:

administering to a patient in the need thereof an effective amount of a humanized monoclonal antibody or fragment thereof which comprises a heavy and light chain, wherein the heavy chain comprises the sequences:

SEQ ID NO: 1

GYTFSRYW,

SEQ ID NO: 2

ILPGSGST, and

SEQ ID NO: 3

TEGYEYDGFDY and a light chain that comprises the sequences:

SEQ ID NO: 4

QSIVYSNGNTY,

SEQUENCE: RVS, and

SEQ ID NO: 5

FQGSHIPYT;

and wherein the humanized monoclonal antibody or fragment thereof comprises a sequence selected from the group consisting of:

(AM-VH-C)

SEQ ID NO: 6

QVQLQQSGAELMKPGASVKISCKATGYTFSRYWIEWVKQRPGHGLEWIGEI

LPGSGSTNYNEKFKGKATITADTSSNTAYMQLSSLTSEDSAVYYCTEGYEY

DGFDYWGQGTTLTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRVEP KHHHHHH,

-continued (AM-VH1)

SEQ ID NO: 7

QVQLVQSGAEVKKPGSSVKVSCKASGYTFSRYWISWVRQAPGQGLEWMGRI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRV EPKHHHHHH, (AM-VH2-E40)

SEQ ID NO: 8

QVQLVQSGAEVKKPGSSVKVSCKASGYTFSRYWIEWVRQAPGQGLEWMGRI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRV EPKHHHHHH, (AM-VH3-T26-E55)

SEQ ID NO: 9

QVQLVQSGAEVKKPGSSVKVSCKATGYTFSRYWISWVRQAPGQGLEWMGEI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRV EPKHHHHHH, (AM-VH4-T26-E40-E55)

SEQ ID NO: 10

QVQLVQSGAEVKKPGSSVKVSCKATGYTFSRYWIEWVRQAPGQGLEWMGEI

LPGSGSTNYAQKFQGRVTITADESTSTAYMELSSLRSEDTAVYYCTEGYEY

DGFDYWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVN

HKPSNTKVDKRV EPKHHHHHH, (AM-VL-C)

SEQ ID NO: 11

DVLLSQTPLSLPVSLGDQATISCRSSQSIVYSNGNTYLEWYLQKPGQSPKL

LIYRVSNRFSGVPDRFSGSGSGTDFTLKISRVEAEDLGVYYCFQGSHIPYT

FGGGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC, (AM-VL1)

SEQ ID NO: 12

DVVMTQSPLSLPVTLGQPASISCRSSQSIVYSNGNTYLNWFQQRPGQSPRR

LIYRVSNRDSGVPDRFSGSGSGTDFTLKISRVEAEDVGVYYCFQGSHIPYT

FGQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC, and (AM-VL2-E40)

SEQ ID NO: 13

DVVMTQSPLSLPVTLGQPASISCRSSQSIVYSNGNTYLEWFQQRPGQSPRR

LIYRVSNRDSGVPDRFSGSGSGTDFTLKISRVEAEDVGVYYCFQGSHIPYT

-continued

FGQGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQ

GLSSPVTKSFNRGEC.

* * * * *